(12) United States Patent
Herr et al.

(10) Patent No.: US 11,491,032 B2
(45) Date of Patent: *Nov. 8, 2022

(54) ARTIFICIAL JOINTS USING AGONIST-ANTAGONIST ACTUATORS

(71) Applicant: Massachusetts Institute of Technology, Cambridge, MA (US)

(72) Inventors: Hugh M. Herr, Somerville, MA (US); Lee Harris Magnusson, San Francisco, CA (US); Ken Endo, Cambridge, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 385 days.

This patent is subject to a terminal disclaimer.

(21) Appl. No.: 16/427,646

(22) Filed: May 31, 2019

(65) Prior Publication Data

US 2020/0022823 A1    Jan. 23, 2020

Related U.S. Application Data

(60) Continuation of application No. 15/342,661, filed on Nov. 3, 2016, now Pat. No. 10,307,272, which is a
(Continued)

(51) Int. Cl.
*A61F 2/68* (2006.01)
*A61F 5/01* (2006.01)
(Continued)

(52) U.S. Cl.
CPC .................. *A61F 2/68* (2013.01); *A61F 2/64* (2013.01); *A61F 2/66* (2013.01); *A61F 2/6607* (2013.01);
(Continued)

(58) Field of Classification Search
CPC .. A61F 2/66; A61F 2/6607; A61F 2005/0197; A61F 2002/5072–5075; A61F 5/0127; B25J 9/0006
See application file for complete search history.

(56) References Cited

U.S. PATENT DOCUMENTS 2,489,291 A   11/1949   Henschke et al.
2,529,968 A   11/1950   Sartin
(Continued)

FOREIGN PATENT DOCUMENTS

CN    101061984 A    10/2007
CN    101111211 A     1/2008
(Continued)

OTHER PUBLICATIONS

Abbas, J. J. et al., "Neural Network Control of Functional Neuromuscular Stimulation Systems: Computer Simulation Studies," *IEEE Transactions on Biomedical Engineering*, vol. 42, No. 11, pp. 1117-1127, Nov. 1995.
(Continued)

*Primary Examiner* — Marcia L Watkins
(74) *Attorney, Agent, or Firm* — Hamilton, Brook, Smith & Reynolds, P.C.

(57) ABSTRACT

Artificial limbs and joints that behave like biological limbs and joints employ a synthetic actuator which consumes negligible power when exerting zero force, consumes negligible power when outputting force at constant length (isometric) and while performing dissipative, nonconservative work, is capable of independently engaging flexion and extension tendon-like, series springs, is capable of independently varying joint position and stiffness, and exploits series elasticity for mechanical power amplification.

3 Claims, 34 Drawing Sheets

Related U.S. Application Data continuation of application No. 14/520,091, filed on Oct. 21, 2014, now Pat. No. 9,539,117, which is a division of application No. 12/698,128, filed on Feb. 1, 2010, now Pat. No. 8,864,846, which is a continuation-in-part of application No. 12/608,627, filed on Oct. 29, 2009, now Pat. No. 8,870,967, and a continuation-in-part of application No. 12/157,727, filed on Jun. 12, 2008, now Pat. No. 8,512,415, said application No. 12/608,627 is a continuation of application No. 11/642,993, filed on Dec. 19, 2006, now abandoned, said application No. 12/157,727 is a continuation-in-part of application No. 11/642,993, filed on Dec. 19, 2006, now abandoned, which is a continuation-in-part of application No. 11/600,291, filed on Nov. 15, 2006, now abandoned, which is a continuation-in-part of application No. 11/499,853, filed on Aug. 4, 2006, now Pat. No. 7,313,463, and a continuation-in-part of application No. 11/395,448, filed on Mar. 31, 2006, now abandoned, said application No. 11/499,853 is a continuation-in-part of application No. 11/395,448, filed on Mar. 31, 2006, now abandoned.

(60) Provisional application No. 61/148,545, filed on Jan. 30, 2009, provisional application No. 60/934,223, filed on Jun. 12, 2007, provisional application No. 60/751,680, filed on Dec. 19, 2005, provisional application No. 60/736,929, filed on Nov. 15, 2005, provisional application No. 60/705,651, filed on Aug. 4, 2005, provisional application No. 60/704,517, filed on Aug. 1, 2005, provisional application No. 60/666,876, filed on Mar. 31, 2005.

(51) Int. Cl.

| | | |
|---|---|---|
| *B25J 9/16* | (2006.01) | |
| *A61F 2/76* | (2006.01) | |
| *A61F 2/72* | (2006.01) | |
| *A61F 2/66* | (2006.01) | |
| *B25J 9/10* | (2006.01) | |
| *A61F 2/64* | (2006.01) | |
| *B25J 9/00* | (2006.01) | |
| *G16H 50/50* | (2018.01) | |
| *G16H 40/63* | (2018.01) | |
| *A61F 2/60* | (2006.01) | |
| *A61F 2/70* | (2006.01) | |
| *A61F 2/50* | (2006.01) | |
| *A61F 2/74* | (2006.01) | |

(52) U.S. Cl.
CPC ............. *A61F 2/76* (2013.01); *A61F 5/0123* (2013.01); *A61F 5/0127* (2013.01); *B25J 9/0006* (2013.01); *B25J 9/1075* (2013.01); *B25J 9/1633* (2013.01); *G16H 40/63* (2018.01); *G16H 50/50* (2018.01); *A61F 2/605* (2013.01); *A61F 2/72* (2013.01); *A61F 2/74* (2021.08); *A61F 2/741* (2021.08); *A61F 2002/5003* (2013.01); *A61F 2002/503* (2013.01); *A61F 2002/5004* (2013.01); *A61F 2002/5006* (2013.01); *A61F 2002/5018* (2013.01); *A61F 2002/5033* (2013.01); *A61F 2002/5066* (2013.01); *A61F 2002/5072* (2013.01); *A61F 2002/5075* (2013.01); *A61F 2002/5079* (2013.01); *A61F 2002/5093* (2013.01); *A61F 2002/6818* (2013.01); *A61F 2002/6845* (2013.01); *A61F 2002/6854* (2013.01); *A61F 2002/6872* (2013.01); *A61F 2002/701* (2013.01); *A61F 2002/704* (2013.01); *A61F 2002/705* (2013.01); *A61F 2002/762* (2013.01); *A61F 2002/763* (2013.01); *A61F 2002/764* (2013.01); *A61F 2002/7625* (2013.01); *A61F 2002/7635* (2013.01); *A61F 2002/7645* (2013.01); *A61F 2005/0137* (2013.01); *A61F 2005/0141* (2013.01); *A61F 2005/0144* (2013.01); *A61F 2005/0155* (2013.01); *A61F 2005/0179* (2013.01)

(56) References Cited

U.S. PATENT DOCUMENTS

| | | |
|---|---|---|
| 3,016,760 A | 1/1962 | Wrighton et al. |
| 3,098,645 A | 7/1963 | Owens |
| 3,207,497 A | 9/1965 | Schoonover |
| 3,449,769 A | 6/1969 | Mizen |
| 3,844,279 A | 10/1974 | Konvalin |
| 3,871,032 A | 3/1975 | Karas |
| 3,916,450 A | 11/1975 | Minor |
| 4,442,390 A | 4/1984 | Davis |
| 4,463,291 A | 7/1984 | Usry |
| 4,518,307 A | 5/1985 | Bloch |
| 4,532,462 A | 7/1985 | Washbourn et al. |
| 4,546,295 A | 10/1985 | Wickham et al. |
| 4,546,296 A | 10/1985 | Washbourn et al. |
| 4,546,297 A | 10/1985 | Washbourn et al. |
| 4,546,298 A | 10/1985 | Wickham et al. |
| 4,569,352 A | 2/1986 | Petrofsky et al. |
| 4,600,357 A | 7/1986 | Coules |
| 4,657,470 A | 4/1987 | Clarke et al. |
| 4,672,955 A | 6/1987 | Cooper |
| 4,843,921 A | 7/1989 | Kremer |
| 4,865,376 A | 9/1989 | Leaver et al. |
| 4,872,665 A | 10/1989 | Chareire |
| 4,872,803 A | 10/1989 | Asakawa |
| 4,909,535 A | 3/1990 | Clark et al. |
| 4,921,293 A | 5/1990 | Ruoff et al. |
| 4,921,393 A | 5/1990 | Andeen et al. |
| 4,923,474 A | 5/1990 | Klasson et al. |
| 4,923,475 A | 5/1990 | Gosthnian et al. |
| 4,936,295 A | 6/1990 | Crane |
| 4,964,402 A | 10/1990 | Grim et al. |
| 4,989,161 A | 1/1991 | Oaki |
| 5,012,591 A | 5/1991 | Asakawa |
| 5,049,797 A | 9/1991 | Phillips |
| 5,062,673 A | 11/1991 | Mimura |
| 5,088,478 A | 2/1992 | Grim |
| 5,092,902 A | 3/1992 | Adams et al. |
| 5,112,296 A | 5/1992 | Beard et al. |
| 5,174,168 A | 12/1992 | Takagi et al. |
| 5,181,933 A | 1/1993 | Phillips |
| 5,252,102 A | 10/1993 | Singer et al. |
| 5,294,873 A | 3/1994 | Seraji |
| RE34,661 E | 7/1994 | Grim |
| 5,327,790 A | 7/1994 | Levin et al. |
| 5,367,790 A | 11/1994 | Gamow et al. |
| 5,383,939 A | 1/1995 | James |
| 5,405,409 A | 4/1995 | Knoth |
| 5,442,270 A | 8/1995 | Tetsuaki |
| 5,443,521 A | 8/1995 | Knoth et al. |
| 5,456,341 A | 10/1995 | Garnjost et al. |
| 5,458,143 A | 10/1995 | Herr |
| 5,476,441 A | 12/1995 | Durfee et al. |
| 5,502,363 A | 3/1996 | Tasch et al. |
| 5,514,185 A | 5/1996 | Phillips |
| 5,556,422 A | 9/1996 | Powell, III et al. |
| 5,571,205 A | 11/1996 | James |
| 5,643,332 A | 7/1997 | Stein |
| 5,650,704 A | 7/1997 | Pratt et al. |
| 5,662,693 A | 9/1997 | Johnson et al. |
| 5,701,686 A | 12/1997 | Herr et al. |
| 5,718,925 A | 2/1998 | Kristinsson et al. |
| 5,748,845 A | 5/1998 | Labun et al. |

(56) References Cited

U.S. PATENT DOCUMENTS

| | | |
|---|---|---|
| 5,776,205 A | 7/1998 | Phillips |
| 5,865,770 A | 2/1999 | Schectman |
| 5,885,809 A | 3/1999 | Effenberger et al. |
| 5,888,212 A | 3/1999 | Petrofsky et al. |
| 5,888,213 A | 3/1999 | Sears et al. |
| 5,898,948 A | 5/1999 | Kelly et al. |
| 5,910,720 A | 6/1999 | Williamson et al. |
| 5,932,230 A | 8/1999 | DeGrate |
| 5,944,760 A | 8/1999 | Christensen |
| 5,971,729 A | 10/1999 | Kristinsson et al. |
| 5,972,036 A | 10/1999 | Kristinsson et al. |
| 5,980,435 A | 11/1999 | Joutras et al. |
| 6,029,374 A | 2/2000 | Herr et al. |
| 6,056,712 A | 5/2000 | Grim |
| 6,067,892 A | 5/2000 | Erickson |
| 6,071,313 A | 6/2000 | Phillips |
| 6,076,011 A | 6/2000 | Hoover |
| 6,136,039 A | 10/2000 | Kristinsson et al. |
| 6,144,385 A | 11/2000 | Girard |
| 6,202,806 B1 | 3/2001 | Sandrin et al. |
| 6,223,648 B1 | 5/2001 | Erickson |
| 6,240,797 B1 | 6/2001 | Morishima et al. |
| 6,267,742 B1 | 7/2001 | Krivosha et al. |
| 6,416,703 B1 | 7/2002 | Kristinsson et al. |
| 6,443,993 B1 | 9/2002 | Koniuk |
| 6,456,884 B1 | 9/2002 | Kenney |
| 6,478,826 B1 | 11/2002 | Phillips et al. |
| 6,485,776 B2 | 11/2002 | Janusson et al. |
| 6,507,757 B1 | 1/2003 | Swain et al. |
| 6,511,512 B2 | 1/2003 | Phillips et al. |
| 6,517,503 B1 | 2/2003 | Naft et al. |
| 6,532,400 B1 | 3/2003 | Jacobs |
| 6,585,774 B2 | 7/2003 | Dean, Jr. et al. |
| 6,589,289 B2 | 7/2003 | Ingimarsson |
| 6,592,539 B1 | 7/2003 | Einarsson et al. |
| 6,610,101 B2 | 8/2003 | Herr et al. |
| 6,626,952 B2 | 9/2003 | Janusson et al. |
| 6,660,042 B1 | 12/2003 | Curcie et al. |
| 6,666,796 B1 | 12/2003 | MacCready, Jr. |
| 6,706,364 B2 | 3/2004 | Janusson et al. |
| 6,752,774 B2 | 6/2004 | Townsend et al. |
| 6,764,520 B2 | 7/2004 | Deffenbaugh et al. |
| 6,811,571 B1 | 11/2004 | Phillips |
| D503,480 S | 3/2005 | Ingimundarson et al. |
| D503,802 S | 4/2005 | Bjarnason |
| 6,887,279 B2 | 5/2005 | Phillips et al. |
| 6,923,834 B2 | 8/2005 | Karason |
| 6,936,073 B2 | 8/2005 | Karason |
| 6,942,629 B2 | 9/2005 | Hepburn et al. |
| 6,945,947 B2 | 9/2005 | Ingimundarson et al. |
| 6,966,882 B2 | 11/2005 | Horst |
| 6,969,408 B2 | 11/2005 | Lecomte et al. |
| 7,001,563 B2 | 2/2006 | Janusson et al. |
| 7,025,793 B2 | 4/2006 | Egilsson |
| 7,029,500 B2 | 4/2006 | Martin |
| 7,037,283 B2 | 5/2006 | Karason et al. |
| D523,149 S | 6/2006 | Bjarnason |
| 7,063,727 B2 | 6/2006 | Phillips et al. |
| 7,077,818 B2 | 7/2006 | Ingimundarson et al. |
| 7,094,058 B2 | 8/2006 | Einarsson |
| 7,094,212 B2 | 8/2006 | Karason et al. |
| D527,825 S | 9/2006 | Ingimundarson et al. |
| D529,180 S | 9/2006 | Ingimundarson et al. |
| 7,101,487 B2 | 9/2006 | Hsu et al. |
| 7,105,122 B2 | 9/2006 | Karason |
| 7,107,180 B2 | 9/2006 | Karason |
| 7,118,601 B2 | 10/2006 | Yasui et al. |
| 7,118,602 B2 | 10/2006 | Bjarnason |
| 7,136,722 B2 | 11/2006 | Nakamura et al. |
| D533,280 S | 12/2006 | Wyatt et al. |
| 7,144,429 B2 | 12/2006 | Carstens |
| 7,145,305 B2 | 12/2006 | Takenaka et al. |
| 7,154,017 B2 | 12/2006 | Sigurjonsson et al. |
| 7,161,056 B2 | 1/2007 | Gudnason et al. |
| 7,169,188 B2 | 1/2007 | Carstens |
| 7,169,189 B2 | 1/2007 | Bjarnason et al. |
| 7,169,190 B2 | 1/2007 | Phillips et al. |
| 7,198,071 B2 | 4/2007 | Bisbee, III et al. |
| 7,198,610 B2 | 4/2007 | Ingimundarson et al. |
| 7,217,060 B2 | 5/2007 | Ingimarsson |
| 7,220,889 B2 | 5/2007 | Sigurjonsson et al. |
| 7,223,899 B2 | 5/2007 | Sigurjonsson |
| 7,227,050 B2 | 6/2007 | Sigurjonsson et al. |
| 7,230,154 B2 | 6/2007 | Sigurjonsson |
| 7,235,108 B2 | 6/2007 | Carstens |
| 7,240,876 B2 | 7/2007 | Doubleday et al. |
| 7,266,910 B2 | 9/2007 | Ingimundarson |
| 7,270,644 B2 | 9/2007 | Ingimundarson |
| 7,279,009 B2 | 10/2007 | Herr et al. |
| 7,288,076 B2 | 10/2007 | Grim et al. |
| 7,295,892 B2 | 11/2007 | Herr et al. |
| RE39,961 E | 12/2007 | Petrofsky et al. |
| 7,303,538 B2 | 12/2007 | Grim et al. |
| 7,304,202 B2 | 12/2007 | Sigurjonsson et al. |
| 7,311,686 B1 | 12/2007 | Iglesias et al. |
| 7,313,463 B2 | 12/2007 | Herr et al. |
| D558,884 S | 1/2008 | Ingimundarson et al. |
| 7,314,490 B2 | 1/2008 | Bédard et al. |
| 7,335,233 B2 | 2/2008 | Hsu et al. |
| 7,347,877 B2 | 3/2008 | Clausen et al. |
| D567,072 S | 4/2008 | Ingimundarson et al. |
| 7,371,262 B2 | 5/2008 | Lecomte et al. |
| 7,377,944 B2 | 5/2008 | Janusson et al. |
| RE40,363 E | 6/2008 | Grim et al. |
| 7,381,860 B2 | 6/2008 | Gudnason et al. |
| 7,393,364 B2 | 7/2008 | Martin |
| 7,396,975 B2 | 7/2008 | Sigurjonsson et al. |
| 7,402,721 B2 | 7/2008 | Sigurjonsson et al. |
| 7,411,109 B2 | 8/2008 | Sigurjonsson et al. |
| D576,781 S | 9/2008 | Chang et al. |
| D577,828 S | 9/2008 | Ingimundarson et al. |
| 7,423,193 B2 | 9/2008 | Sigurjonsson et al. |
| 7,427,297 B2 | 9/2008 | Patterson et al. |
| 7,429,253 B2 | 9/2008 | Shimada et al. |
| 7,431,708 B2 | 10/2008 | Sreeramagiri |
| 7,431,737 B2 | 10/2008 | Ragnarsdottir et al. |
| 7,438,843 B2 | 10/2008 | Asgeirsson |
| 7,449,005 B2 | 11/2008 | Pickering et al. |
| 7,455,696 B2 | 11/2008 | Bisbee, III et al. |
| D583,956 S | 12/2008 | Chang et al. |
| 7,459,598 B2 | 12/2008 | Sigurjonsson et al. |
| 7,465,281 B2 | 12/2008 | Grim et al. |
| 7,465,283 B2 | 12/2008 | Grim et al. |
| 7,468,471 B2 | 12/2008 | Sigurjonsson et al. |
| 7,470,830 B2 | 12/2008 | Sigurjonsson et al. |
| 7,485,152 B2 | 2/2009 | Haynes et al. |
| 7,488,349 B2 | 2/2009 | Einarsson |
| 7,488,864 B2 | 2/2009 | Sigurjonsson et al. |
| D588,753 S | 3/2009 | Ingimundarson et al. |
| 7,503,937 B2 | 3/2009 | Asgeirsson et al. |
| 7,513,880 B2 | 4/2009 | Ingimundarson et al. |
| 7,513,881 B1 | 4/2009 | Grim et al. |
| D592,755 S | 5/2009 | Chang et al. |
| D592,756 S | 5/2009 | Chang et al. |
| 7,527,253 B2 | 5/2009 | Sugar et al. |
| 7,531,006 B2 | 5/2009 | Clausen et al. |
| 7,531,711 B2 | 5/2009 | Sigurjonsson et al. |
| 7,534,220 B2 | 5/2009 | Cormier et al. |
| 7,544,214 B2 | 6/2009 | Gramnas |
| 7,549,970 B2 | 6/2009 | Tweardy |
| D596,301 S | 7/2009 | Campos et al. |
| 7,578,799 B2 | 8/2009 | Thorsteinsson et al. |
| 7,581,454 B2 | 9/2009 | Clausen et al. |
| 7,597,672 B2 | 10/2009 | Kruijsen et al. |
| 7,597,674 B2 | 10/2009 | Hu et al. |
| 7,597,675 B2 | 10/2009 | Ingimundarson et al. |
| 7,618,463 B2 | 11/2009 | Oddsson et al. |
| 7,632,315 B2 | 12/2009 | Egilsson |
| 7,637,957 B2 | 12/2009 | Ragnarsdottir et al. |
| 7,637,959 B2 | 12/2009 | Clausen et al. |
| 7,641,700 B2 | 1/2010 | Yasui |
| 7,650,204 B2 | 1/2010 | Dariush |
| 7,662,191 B2 | 2/2010 | Asgeirsson |
| D611,322 S | 3/2010 | Robertson |

(56) References Cited

U.S. PATENT DOCUMENTS

| | | |
|---|---|---|
| 7,674,212 B2 | 3/2010 | Kruijsen et al. |
| 7,691,154 B2 | 4/2010 | Asgeirsson et al. |
| 7,696,400 B2 | 4/2010 | Sigurjonsson et al. |
| 7,704,218 B2 | 4/2010 | Einarsson et al. |
| D616,555 S | 5/2010 | Thorgilsdottir et al. |
| D616,556 S | 5/2010 | Hu |
| 7,713,225 B2 | 5/2010 | Ingimundarson et al. |
| D616,996 S | 6/2010 | Thorgilsdottir et al. |
| D616,997 S | 6/2010 | Thorgilsdottir et al. |
| D618,359 S | 6/2010 | Einarsson |
| 7,727,174 B2 | 6/2010 | Chang et al. |
| 7,736,394 B2 | 6/2010 | Bedard et al. |
| 7,745,682 B2 | 6/2010 | Sigurjonsson et al. |
| D620,124 S | 7/2010 | Einarsson |
| 7,749,183 B2 | 7/2010 | Ingimundarson et al. |
| 7,749,281 B2 | 7/2010 | Egilsson |
| 7,762,973 B2 | 7/2010 | Einarsson et al. |
| 7,771,488 B2 | 8/2010 | Asgeirsson et al. |
| 7,780,741 B2 | 8/2010 | Janusson et al. |
| 7,794,418 B2 | 9/2010 | Ingimundarson et al. |
| 7,794,505 B2 | 9/2010 | Clausen et al. |
| 7,811,333 B2 | 10/2010 | Jonsson et al. |
| 7,811,334 B2 | 10/2010 | Ragnarsdottir et al. |
| D627,079 S | 11/2010 | Robertson |
| 7,833,181 B2 | 11/2010 | Cormier et al. |
| 7,842,848 B2 | 11/2010 | Janusson et al. |
| D628,696 S | 12/2010 | Robertson |
| D629,115 S | 12/2010 | Robertson |
| 7,846,213 B2 | 12/2010 | Lecomte et al. |
| 7,862,620 B2 | 1/2011 | Clausen et al. |
| 7,863,797 B2 | 1/2011 | Calley |
| 7,867,182 B2 | 1/2011 | Iglesias et al. |
| 7,867,284 B2 | 1/2011 | Bedard |
| 7,867,285 B2 | 1/2011 | Clausen et al. |
| 7,867,286 B2 | 1/2011 | Einarsson |
| 7,868,511 B2 | 1/2011 | Calley |
| 7,879,110 B2 | 2/2011 | Phillips |
| 7,891,258 B2 | 2/2011 | Clausen et al. |
| 7,892,195 B2 | 2/2011 | Grim et al. |
| D634,438 S | 3/2011 | Hu |
| D634,852 S | 3/2011 | Hu |
| 7,896,826 B2 | 3/2011 | Hu et al. |
| 7,896,827 B2 | 3/2011 | Ingimundarson et al. |
| 7,896,927 B2 | 3/2011 | Clausen et al. |
| 7,909,884 B2 | 3/2011 | Egilsson et al. |
| 7,910,793 B2 | 3/2011 | Sigurjonsson et al. |
| 7,914,475 B2 | 3/2011 | Wyatt et al. |
| 7,918,765 B2 | 4/2011 | Kruijsen et al. |
| D637,942 S | 5/2011 | Lee et al. |
| 7,935,068 B2 | 5/2011 | Einarsson |
| D640,380 S | 6/2011 | Tweardy et al. |
| D640,381 S | 6/2011 | Tweardy et al. |
| 7,955,398 B2 | 6/2011 | Bedard et al. |
| 7,959,589 B2 | 6/2011 | Sreeramagiri et al. |
| D641,482 S | 7/2011 | Robertson et al. |
| D641,483 S | 7/2011 | Robertson et al. |
| 7,981,068 B2 | 7/2011 | Thorgilsdottir et al. |
| 7,985,193 B2 | 7/2011 | Thorsteinsson et al. |
| D643,537 S | 8/2011 | Lee |
| 7,992,849 B2 | 8/2011 | Sugar et al. |
| 7,998,221 B2 | 8/2011 | Lecomte et al. |
| 8,002,724 B2 | 8/2011 | Hu et al. |
| 8,007,544 B2 | 8/2011 | Jonsson et al. |
| 8,016,781 B2 | 9/2011 | Ingimundarson et al. |
| 8,021,317 B2 | 9/2011 | Arnold et al. |
| 8,025,632 B2 | 9/2011 | Einarsson |
| 8,025,699 B2 | 9/2011 | Lecomte et al. |
| 8,026,406 B2 | 9/2011 | Janusson et al. |
| D646,394 S | 10/2011 | Tweardy et al. |
| D647,622 S | 10/2011 | Lee et al. |
| D647,623 S | 10/2011 | Thorgilsdottir et al. |
| D647,624 S | 10/2011 | Thorgilsdottir et al. |
| 8,034,120 B2 | 10/2011 | Egilsson et al. |
| 8,038,636 B2 | 10/2011 | Thorgilsdottir et al. |
| 8,043,244 B2 | 10/2011 | Einarsson et al. |
| 8,043,245 B2 | 10/2011 | Campos et al. |
| RE42,903 E | 11/2011 | Deffenbaugh et al. |
| 8,048,007 B2 | 11/2011 | Roy |
| 8,048,013 B2 | 11/2011 | Ingimundarson et al. |
| 8,048,172 B2 | 11/2011 | Jonsson et al. |
| 8,052,760 B2 | 11/2011 | Egilsson et al. |
| 8,057,550 B2 | 11/2011 | Clausen et al. |
| 8,075,633 B2 | 12/2011 | Herr et al. |
| 8,202,325 B2 | 6/2012 | Albrecht-Laatsch et al. |
| 8,287,477 B1 | 10/2012 | Herr et al. |
| 8,376,971 B1 | 2/2013 | Herr et al. |
| 8,419,804 B2 | 4/2013 | Herr et al. |
| 8,500,823 B2 | 8/2013 | Herr et al. |
| 8,512,415 B2 | 8/2013 | Herr et al. |
| 8,555,415 B2 | 10/2013 | Bradstreet et al. |
| 8,734,528 B2 | 5/2014 | Herr et al. |
| 8,864,846 B2 | 10/2014 | Herr et al. |
| 8,870,967 B2 | 10/2014 | Herr et al. |
| 9,149,370 B2 | 10/2015 | Herr et al. |
| 9,221,177 B2 | 12/2015 | Herr et al. |
| 9,333,097 B2 | 5/2016 | Herr et al. |
| 9,339,397 B2 | 5/2016 | Herr et al. |
| 9,539,117 B2 | 1/2017 | Herr et al. |
| 9,975,249 B2 | 5/2018 | Herr et al. |
| 10,137,011 B2 | 11/2018 | Herr et al. |
| 10,307,272 B2 | 6/2019 | Herr et al. |
| 10,342,681 B2 | 7/2019 | Herr et al. |
| 2001/0029400 A1 | 10/2001 | Deffenbaugh et al. |
| 2002/0052663 A1 | 5/2002 | Herr et al. |
| 2002/0092724 A1 | 7/2002 | Koleda |
| 2002/0138153 A1 | 9/2002 | Koniuk |
| 2003/0093021 A1 | 5/2003 | Goffer |
| 2003/0125814 A1 | 7/2003 | Paasivaara et al. |
| 2003/0139783 A1 | 7/2003 | Kilgore et al. |
| 2003/0163206 A1 | 8/2003 | Yasui et al. |
| 2003/0195439 A1 | 10/2003 | Caselnova |
| 2004/0039454 A1 | 2/2004 | Herr et al. |
| 2004/0049290 A1 | 3/2004 | Bedard |
| 2004/0054423 A1 | 3/2004 | Martin |
| 2004/0064195 A1 | 4/2004 | Herr |
| 2004/0088025 A1 | 5/2004 | Gesotti |
| 2004/0106881 A1* | 6/2004 | McBean ............... A61B 5/389 601/5 |
| 2004/0181118 A1 | 9/2004 | Kochamba |
| 2004/0181289 A1 | 9/2004 | Bedard et al. |
| 2005/0007834 A1 | 1/2005 | Hidaka |
| 2005/0038525 A1 | 2/2005 | Doddroe et al. |
| 2005/0043614 A1 | 2/2005 | Huizenga et al. |
| 2005/0049652 A1 | 3/2005 | Tong |
| 2005/0059908 A1 | 3/2005 | Bogert |
| 2005/0085948 A1 | 4/2005 | Herr et al. |
| 2005/0155444 A1 | 7/2005 | Otaki et al. |
| 2005/0192677 A1 | 9/2005 | Ragnarsdottir et al. |
| 2005/0209707 A1 | 9/2005 | Phillips et al. |
| 2005/0228515 A1 | 10/2005 | Musallam et al. |
| 2006/0004307 A1 | 1/2006 | Horst |
| 2006/0064047 A1 | 3/2006 | Shimada et al. |
| 2006/0069448 A1 | 3/2006 | Yasui |
| 2006/0094989 A1 | 5/2006 | Scott et al. |
| 2006/0122711 A1 | 6/2006 | Bedard et al. |
| 2006/0135883 A1 | 6/2006 | Jonsson et al. |
| 2006/0211956 A1 | 9/2006 | Sankai |
| 2006/0213305 A1 | 9/2006 | Sugar et al. |
| 2006/0224246 A1 | 10/2006 | Clausen et al. |
| 2006/0249315 A1 | 11/2006 | Herr et al. |
| 2006/0258967 A1 | 11/2006 | Fujil et al. |
| 2006/0264790 A1 | 11/2006 | Kruijsen et al. |
| 2006/0276728 A1 | 12/2006 | Ashihara et al. |
| 2007/0016329 A1 | 1/2007 | Herr et al. |
| 2007/0032951 A1 | 2/2007 | Tanenhaus et al. |
| 2007/0043449 A1 | 2/2007 | Herr et al. |
| 2007/0050044 A1 | 3/2007 | Haynes et al. |
| 2007/0123997 A1 | 5/2007 | Herr et al. |
| 2007/0129653 A1 | 6/2007 | Sugar et al. |
| 2007/0145930 A1 | 6/2007 | Zaier |
| 2007/0162152 A1 | 7/2007 | Herr et al. |
| 2007/0267791 A1 | 11/2007 | Hollander et al. |
| 2008/114272 A1 | 5/2008 | Herr et al. |
| 2008/0155444 A1 | 6/2008 | Pannese et al. |

(56) References Cited

U.S. PATENT DOCUMENTS

| | | |
|---|---|---|
| 2008/0169729 A1 | 7/2008 | Asai |
| 2009/0030530 A1 | 1/2009 | Martin |
| 2009/0204230 A1 | 8/2009 | Kaltenborn et al. |
| 2009/0222105 A1 | 9/2009 | Clausen |
| 2009/0265018 A1 | 10/2009 | Goldfarb et al. |
| 2010/0113988 A1 | 5/2010 | Matsuoka |
| 2010/0185301 A1 | 7/2010 | Hansen et al. |
| 2010/0241242 A1 | 9/2010 | Herr et al. |
| 2010/0256537 A1 | 10/2010 | Menga |
| 2010/0280629 A1 | 11/2010 | Jung et al. |
| 2010/0324699 A1 | 12/2010 | Herr et al. |
| 2011/0040216 A1 | 2/2011 | Herr et al. |
| 2011/0224804 A1 | 9/2011 | Clausen et al. |
| 2011/0245931 A1 | 10/2011 | Clausen et al. |
| 2011/0260380 A1 | 10/2011 | Hollander et al. |
| 2011/0264230 A1 | 10/2011 | Herr et al. |
| 2011/0278857 A1 | 11/2011 | Sugar et al. |
| 2011/0307079 A1 | 12/2011 | Oweiss et al. |
| 2012/0136459 A1 | 5/2012 | Herr et al. |
| 2012/0209405 A1 | 8/2012 | Herr et al. |
| 2012/0271433 A1 | 10/2012 | Galea et al. |
| 2013/0110256 A1 | 5/2013 | Herr et al. |
| 2013/0158444 A1 | 6/2013 | Herr et al. |
| 2013/0197318 A1 | 8/2013 | Herr et al. |
| 2013/0310979 A1 | 11/2013 | Herr et al. |
| 2014/0046455 A1 | 2/2014 | Herr et al. |
| 2014/0088729 A1 | 3/2014 | Herr et al. |
| 2014/0257519 A1 | 9/2014 | Herr et al. |
| 2015/0051710 A1 | 2/2015 | Herr et al. |
| 2016/0207201 A1 | 7/2016 | Herr et al. |
| 2016/0228265 A1 | 8/2016 | Herr et al. |
| 2016/0338857 A1 | 11/2016 | Herr et al. |
| 2017/0049587 A1 | 2/2017 | Herr et al. |
| 2019/0175365 A1 | 6/2019 | Herr et al. |

FOREIGN PATENT DOCUMENTS

| | | |
|---|---|---|
| EP | 1169982 | 1/2002 |
| EP | 1393866 | 3/2004 |
| JP | 2008-87143 A | 4/2008 |
| WO | WO 2001/054630 A1 | 8/2001 |
| WO | WO 2003/005934 A2 | 1/2003 |
| WO | WO 03068453 | 8/2003 |
| WO | WO 2004/017872 A1 | 3/2004 |
| WO | WO 2004/019832 A1 | 3/2004 |
| WO | WO 2010/027968 A2 | 3/2010 |
| WO | WO 2010/088616 | 8/2010 |
| WO | WO 2010/088635 A1 | 8/2010 |

OTHER PUBLICATIONS

Abul-Haj, C.J. et al., "Functional Assessment of Control Systems for Cybernetic Elbow Prostheses-Part II: Application of the Technique," *IEEE Transactions on Biomedical Engineering*, vol. 17, No. 11, pp. 1037-1047, Nov. 1990.
Aeyels, B., et al., "An EMG-Based Finite State Approach for a Microcomputer-Controlled Above-Knee Prosthesis," *Engineering in Medicine and Biology Society 1995*, pp. 1315-1316 (1997).
Akazawa, K. et al., "Biomimetic EMG-Prosthesis-Hand, 18$^{th}$ Annual International Conference of the IEEE Engineering in Medicine and Biology Society," Amsterdam pp. 535 and 536, 1996.
Aminian, K. et al., "Estimation of Speed and Incline of Walking Using Neural Network," *IEEE Transactions of Instrumentation and Measurement*, 44(3): 743-746 (1995).
Anderson, F.C. et al., "Dynamic Optimization of Human Walking," *Journal of Biomechanical Engineering*, 123: 381-390 (2001).
Andrews, B.J. et al., "Hybrid FES Orthosis Incorporating Closed Loop Control and Sensory Feedback," *J. Biomed. Eng.*, 10:189-195(1988).
Arakawa, T. et al., "Natural Motion Generation of Biped Locomotion Robot Using Hierarchical Trajectory Generation Method Consisting of GA, EP Layers," Proceedings of the 1997 IEEE International Conference on Robotics and Automation, Albuquerque, NM., pp. 375-379.
Au, et al., "Initial experimental study on dynamic interaction between an amputee and a powered ankle-foot prosthesis," Workshop on Dynamic Walking: Mechanics and Control of Human and Robot Locomotion, May 2006, Ann Arbor, MI, p. 1.
Au, S. et al., "Powered Ankle-Foot Prosthesis to Assist Level-Ground and Stair-Descent Gaits," *Neural Networks*, 21: 654-666 (2008).
Au, et al., "Powered Ankle-Foot Prosthesis: The Importance of Series and Parallel Motor Elasticity," IEEE Robotics & Automation Magazine, pp. 52-59, Sep. 2008.
Au, S.K. et al., "An Ankle-Foot Emulation System for the Study of Human Walking Biomechanics," Proceedings of the 2006 IEEE International Conference on Robotics and Automation, Orlando, FL, May 2006, pp. 2939-2945.
Au, S.K. et al., "An EMG-Position Controlled System for an Active Ankle-Foot Prosthesis: An Initial Experimental Study," Proceedings of the 2005 IEEE 9$^{th}$ International Conference on Rehabilitation Robotics, Chicago, IL., pp. 375-379.
Au, S.K. et al., "Biomechanical Design of a Powered Ankle-Foot Prosthesis," Proceedings of the 2007 IEEE 10$^{th}$ International Conference on Rehabilitation Robotics, Noordwijk, The Netherlands, pp. 298-303, Jun. 12-15, 2007.
Au, S.K. et al., "Powered Ankle-Foot Prosthesis for the Improvement of Amputee Ambulation," paper presented at the Proceedings of the 29$^{th}$ Annual International Conference of the IEEE Eng. Med. Bio. Soc., Cité Internationale, Lyon, France, (Aug. 2007).
Au, S.K. et al., "Powered Ankle-Foot Prosthesis Improves Walking Metabolic Economy," *IEEE Transactions on Robotics*, 25(1): 51-66 (2009).
Au, S. K.-W., et al., "Powered Ankle-Foot Prosthesis for the Improvement of Amputee Walking Economy," Doctoral dissertation, Massachusetts Institute of Technology (2007).
Barth, D.G. et al., "Gait Analysis and Energy Cost of Below-Knee Amputees Wearing Six Different Prosthetic Feet," *JPO*, 4(2): 63 (1992). . . .
Baten, Chris T.M. et al., "Inertial Sensing in Ambulatory Back Load Estimation," paper presented at tire 18$^{th}$ Annual International Conference of the IEEE Engineering in Medicine and Biology Society, Amsterdam, 1996, pp. 497-498.
Bateni, H. et al., "Kinematic and Kinetic Variations of Below-Knee Amputee Gait," *JPO*, 14(1):1-12 (2002).
Blaya, J. et al., "Active Ankle Foot Orthoses (AAFO)," Artificial Intelligence Laboratory, Massachusetts Institute of Technology, Cambridge, MA, pp. 275-277. (no date given).
Blaya, J.A. et al., "Active Ankle Foot Orthoses (AAFO)," Retrieved from: http://www.ai.mit.edu. Artificial Intelligence Laboratory, Massachusetts Institute of Technology, Cambridge, Massachusetts, pp. 251-253 (no date given).
Blaya, J.A. et al., "Adaptive Control of a Variable-Impedance Ankle-Foot Orthosis to Assist Drop Foot Gait," Artificial Intelligence Lab and Harvard-MIT Division Health Sciences and Technology, Boston, MA, 30 pages, no date given.
Blaya, J.A. et al., "Adaptive Control of a Variable-Impedance Ankle-Foot Orthosisto Assist Drop-Foot Gait," IEEE Transactions on Neural Systems and Rehabilitation Engineering, 12(1): 24-31 (2004).
Blaya, J.A., "Force-Controllable Ankle Foot Orthosis (AFO) to Assist Drop Foot Gait," submitted to the Department of Mechanical Engineering, Massachusetts Institute of Technology. Cambridge, Massachusetts (Feb. 2003), 88 pages.
Blickhan, R., "The Spring-Mass Model for Running and Hopping," *J. Biomechanics*, 22(11 /12): 1217-1227 (1989).
Bortz, J.E. "A New Mathematical Formulation for Strapdown Inertial Navigation," *IEEE Transactions on Aerospace and Electronic Systems*, AES-7(1): 61-66 (1971).
Bouten, C.V. et al., "Assessment of Energy Expenditure for Physical Activity Using a Triaxial Accelerometer," *Medicine and Science in Sports and Exercise*, 26(12):1516-1523 (1994).
Brockway, J.M., "Derivation of Formulae Used to Calculate Energy Expenditure in Man," *Human Nutrition: Clinical Nutrition* 41C, pp. 463-471 (1987).

(56) References Cited

OTHER PUBLICATIONS

Brown, T.G., "On the Nature of the Fundamental Activity of the Nervous Centres; Together with an Analysis of the Conditioning of Rhythmic Activity in Progression, and a Theory of the Evolution of Function in the Nervous System," pp. 24-46 (no date given).
Cavagna, G.A., et al., "The Sources of External Work in Level Walking and Running," J. Physiol. 262:639-657 (1976).
Chu, A. et al., "On the Biomimetic Design of the Berkeley Lower Extremity Exoskeleton," paper presented at the Proceedings of the 2005 IEEE International Conference on Robotics and Automation, Barcelona, Spain, (Apr. 2005) pp. 4556-4363.
Clancy, E.A., et al., "Sampling, noise-reduction and amplitude estimation issues in surface electromyography," Journal of Electromyography and Kinesiology:, 12(1):1-16 (Feb. 2002) PMID: 11804807.
Colborne, G.R., et al., "Analysis of mechanical and metabolic factors in the gait of congenital below knee amputees," *Am. J. Phys. Med. Rehabil.*, vol. 92, pp. 272-278, Oct. 1992.
Colgate, J.E., "The Control of Dynamically Interacting Systems," Massachusetts Institute of Technology, pp. 1-15, Aug. 1988.
Collins, S.H. et al., "Controlled Energy Storage and Return Prosthesis Reduces Metabolic Cost of Walking," ISB XXth Congress-ASB $29^{th}$ Annual Meeting, Jul. 31-Aug. 5, Cleveland, Ohio, pp. 804 (no year given).
Collins, S.H., et al., "A Bipedal Walking Robot with Efficient and Human-Like Gait," 2005 IEEE. Int'l Conference on Robotics and Automation, Barcelona, Spain, pp. 1983-1988, (Apr. 2005).
Collins, S.H., et al., Supporting Online Material for "Efficient Bipedal Robots Based on Passive-Dynamic Walkers," Mechanical Engineering, University of Michigan, Feb. 11, 2005, Ann Arbor, MI, pp. 1-8.
Cornell University 2009 Disability Status Report, United States (2009).
Crago, P.E. et al., "New Control Strategies for Neuroprosthetic Systems," *Journal of Rehabilitation Research and Development*, vol. 33, No. 2, Apr. 1996, pp. 158-172.
Cronin, N.J., et al., "Mechanical and Neural Stretch Responses of the Human Soleus Muscle at Different Walking Speed," *J Physiol.*, (2009).
Daley, M.A. et al., "Running Stability is Enhanced by a Proximo-Distal Gradient in Joint Neuromechanical Control," *The Journal of Experimental Biology*, vol. 210, pp. 383-394 (Feb. 2007).
Dapena, J. et al., "A Three-Dimensional Analysis of Angular Momentum in the Hammer Throw," Biomechanics Laboratory, Indiana University, IN, *Medicine and Science in Sports and Exercise*, vol. 21, No. 2, pp. 206-220 (1988).
Davids, J.R., "Book Reviews" *Journal of Pediatric Orthopedics* 12, pp. 815, 1992.
Deb, K., "Multi-Objective Optimization Using Evolutionary Algorithms," *Wiley* (2001).
Deb, K., et al., "A Hybrid Multi-Objective Evolutionary Approach to Engineering Shape Design," *International Conference on Evolutionary Multi-Criterion Optimization*, EMO-2001, pp. 385-399 (2001).
Deb, K., et al., "Controlled Elitist Non-Dominated Sorting Genetic Algorithms for Better Convergence," *International Conference on Evolutionary Multi-Criterion Optimization, EMO 2001;* pp. 67-81 (2001).
Delp, S., "Surgery Simulation: A Computer Graphics System to Analyze and Design Musculoskeletal Reconstructions of the Lower Limb," *PhD Thesis,* Stanford, (1990).
Delp, S., et al., "An Interactive Graphics-based Model of the Lower Extremity Orthopaedic Surgical Procedures," *IEEE Transactions on Biomedical Engineering*, 37(8):757-767 (1990).
Dietz, V. "Proprioception and Locomotor Disorders," *Nature Reviews*, vol. 3, pp. 781-790 (Oct. 2002).
Dietz, V. "Spinal Cord Pattern Generators for Locomotion," *Clinical Neurophysiology*, vol. 114, Issue 8, pp. 1-12 (Aug. 2003).

Doerschuk, P.C. et al., "Upper Extremity Limb Function Discrimination Using EMG Signal Analysis," *IEEE Transactions on Biomedical Engineering*, vol. BME-30, No. 1, Jan. 1983, pp. 18-28.
Doke, J. et al., "Mechanics and Energetics of Swinging the Human Leg," *The Journal of Experimental Biology*, vol. 208, pp. 439-445 (2005).
Dollar, A.M. et al., "Lower Extremity Exoskeletons and Active Orthoses: Challenges and State-of-the-Art," *IEEE Transactions on Robotics*, vol. 24, No. 1, pp. 1-15, Feb. 2008.
Donelan, J.M. et al., "Force Regulation of Ankle Extensor Muscle Activity in Freely Walking Cats," *Journal of Neurophysiology*, vol. 101, pp. 360-371 (2009).
Donelan, J.M. et al., "Mechanical work for Step-to-Step Transitions is a Major Determinant of the Metabolic Cost of Human Walking," *The Journal of Experimental Biology*, vol. 205, pp. 3717-3727 (2002).
Donelan, J.M. et al., "Simultaneous Positive and Negative External Mechanical Work in Human Walking," *Journal of Biomechanics*, vol. 35, 2002, pp. 117-124 (2002).
Drake, C., "Foot & Ankle Splints or Orthoses," HemiHelp Information Sheet, London, United Kingdom, 3 pages, http://www.hemihelp.org.uk/leaflets/hbleaflets90.htm Retrieved on: Jun. 20, 2003.
Drake, C., "Ankle & Foot Splints or Orthoses (AFOs)," HemiHelp Information Sheet, pp. 1-6, last revision Dec. 2011.
Drake, C., "Foot & Ankle Splints or Orthoses," HemiHelp Information Sheet No. 13, pp. 1-5, last updated Jun. 2009.
Eilenberg, et al., Control of a Powered Ankle-Foot Prosthesis Based on a Neuromuscular Model, "*IEEE Transactions on Neural Systems & Rehabilitation Eng.*", vol. 18(2):164-173 (Jul. 20, 2010).
Eilenberg, M.F. "A Neuromuscular-Model Based Control Strategy for Powered Ankle-Foot Prostheses," Massachusetts Institute of Technology, pp. 1-90. Jul. 20, 2010.
Ekeberg, Ö et al., "Computer Simulation of Stepping in the Hind Legs of the Cat: An Examination of Mechanisms Regulating the Stance-to-Swing Transition," *J. Neurophysical*, vol. 94, pp. 4256-4268 (2005).
Ekeberg, Ö et al., "Simulations of Neuromuscular Control in Lamprey Swimming," The Royal Society, *Phil. Trans. R. Soc. Land*, vol. 354, pp. 895-902 (1999).
Endo, K., et al., "A Model of Muscle-Tendon Function in Human Walking," In Proc. of ICRA, pp. 1909-1915 (2009).
Endo, K. et al., "A Quasi-Passive Model of Human Leg Function in Level-Ground Walking," Proceedings of the 2006 IEEE/RSJ International Conference on Intelligent Robots and Systems, Oct. 9-15, 2006, Beijing, China, pp. 4935-4939.
Eppinger, S.D. et al., "Three Dynamic Problems in Robot Force Control," *IEEE Transactions on Robotics and Automation*, vol. 8, No. 6, pp. 772-778 (Dec. 1992).
Esquenazi, M.D., A., et al., "Rehabilitation After Amputation," *J Am Podiatr Med Assoc* vol. 91, No. 1, pp. 13-22 (Jan. 2001).
Farley, C.T. et al., "Energetics of Walking and Running: Insights From Simulated Reduced-Gravity Experiments," *J. Appl. Physiol.* 73(6):2709-2712 (1992).
Farry, K.A. et al., "Myoelectric Teleoperation of a Complex Robotic Hand," *IEEE Transactions on Robotics and Automation*, vol. 12, No. 5, pp. 775-778 (Oct. 1996).
Featherstone, R., "Robot Dynamics Algorithms," Edinburgh University, pp. 1-173, 1987.
Ferris, D.P., et al., "Robotic lower limb exoskeletons using proportional myoelectric control," pp. 2119-2124 (Sep. 2009).
Fite, K. et al., "Design and Control of an Electrically Powered Knee Prosthesis," Proceedings of the 2007 IEEE $10^{th}$ International Conference on Rehabilitation Robotics, Jun. 12-15, 2007, The Netherlands, pp. 902-905.
Flowers, W.C., "A Man-Interactive Simulator System for Above-Knee Prosthetics Studies," Partial fulfillment for Doctor of Philosophy, MIT, pp. 1-94 Aug. 1972.
Fod, A. et al., "Automated Derivation of Primitives for Movement Classification," *Autonomous Robots*, vol. 12, No. 1, pp. 39-54 (Jan. 2002).

(56) References Cited

OTHER PUBLICATIONS

Frigon, A. et al., "Experiments and Models of Sensorimotor Interactions During Locomotion," *Biological Cybernetics*, vol. 95, pp. 606-627 (2006).
Fujita et al., "Joint Angle Control with Command Filter for Human Ankle Movement Using Functional Electrical Stimulation," Proceedings of the Ninth Annual Conference of the IEEE Engineering in Medicine and Biology Society, Boston, MA, Nov. 13-16, 1987.
Fukuda, O. et al., "A Human-Assisting Manipulator Teleoperated by EMG Signals and Arm Motions," *IEEE Transactions on Robotics and Automation*, vol. 19, No. 2, pp. 210-222 (Apr. 2003).
Fukunaga, T., et al., "In Vivo Behavior of Human Muscle Tendon During Walking," *Proc. Biol. Sci.*, 268:229-233 (2001).
Gates, D.H. Thesis: "Characterizing Ankle Function During Stair Ascent, Descent, and Level Walking for Ankle Prosthesis and Orthosis Design," Boston University, pp. 1-84 (2004).
Gates, D.H., et al., "Characterization of ankle function during stair ambulation," *Conference Proceedings: Annual International Conference of the IEEE Engineering in Medicine and Biology Society. IEEE Engineering in Medicine and Biology Society. Conference*, 6:4248-4251, (2004). PMID: 17271242.
Gerritsen, K.G.M. et al., "Direct Dynamics Simulation of the Impact Phase in Heel-Toe Running," *J. Biomechanics*, vol. 28, No. 6, pp. 661-668 (1995).
Geyer, H. et al., "A Muscle-Reflex Model That Encodes Principles of Legged Mechanics Predicts Human Walking Dynamics and Muscle Activities," *IEEE Transactions on Neural Systems and Rehabilitation Engineering*, vol. 18, No. 3, pp. 263-273 (Jun. 2010).
Geyer, H. et al., "A Muscle-Reflex Model that Encodes Principles of Legged Mechanics Produces Human Walking Dynamics and Muscle Activities," IEEE Transactions on Neural Systems and Rehabilitation Engineering, vol. X. No. X. pp. 1-10 (2010).
Geyer, H. et al., "Compliant Leg Behavior Explains Basic Dynamics of Walking and Running," *Proc. R. Soc. B*, vol. 273, pp. 2861-2867 (2006).
Geyer, H. et al., "Positive Force Feedback in Bouncing Gaits?," *Proc. R. Soc. Lond, B*, vol. 270, pp. 2173-2183 (2003).
Ghigliazza, R.M. et al., "A Simply Stabilized Running Model," University of Pennsylvania, *SIAM Journal on Applied Dynamical Systems*, vol. 2, Issue 2, pp. 187-218 (May 8, 2004).
Giszter, S., et al., "Convergent Force Fields Organized in the Frog's Spinal Cord," *Journal of Neuroscience*, 13(2): 467-491 (1993).
Godha, S. et al., "Integrated GPS/INS System for Pedestrian Navigation in a Signal Degraded Environment." ION GNSS, Fort Worth, TX, Sep. 26-29, 2006 pp. 1-14.
Goswami, A. et al., "Rate of Change of Angular Momentum and Balance Maintenance of Biped Robots," Proceedings of the 2004 IEEE International Conference on Robotics and Automation, New Orleans, LA, Apr. 2004, pp. 3785-3790.
Goswami, A., "Postural Stability of Biped Robots and the Foot-Rotation Indicator (FRI) Point," *The International Journal of Robotics Research*, vol. 18, No. 6, pp. 523-533 (Jun. 1999).
Graupe, D. et al., "A Microprocessor System for Multifunctional Control of Upper-Limb Prostheses via Myoelectric Signal Identification." *IEEE Transactions on Automatic Control*, vol. 23, No. 4, pp. 538-544 (Aug. 1978).
Gregoire, L. et al., "Role of Mono- and Biarticular Muscles in Explosive Movements," *International Journal of Sports Medicine*, vol. 5, No. 6, pp. 299-352 (Dec. 1984).
Grey, M.J., et al., "Positive Force Feedback in Human Walking," *J of Physiology*, 581(1):99-105 (2007).
Grieve, D., "Prediction of Gastroenemius Length from Knee and Ankle Joint Posture," *International Series of Biomechanics*, 2A:405-412 (1978).
Grillner, S. and Zangger, P., "On the Central Generation of Locomotion in the Low Spinal Cat," *Experimental Brain Research*, 34: 241-261 (1979).
Grimes, D.L., "An Active Multi-Mode Above-Knee Prosthesis Controller," unpublished doctoral dissertation, Massachusetts Institute of Technology (1979).
Gu, W.J., "The Regulation of Angular Momentum During Human Walking," unpublished doctoral dissertation, Massachusetts Institute of Technology, 42 pages (2003).
Gunther, M. et al., "Human Leg Design: Optimal Axial Alignment Under Constraints," *J. Math. Biol.*, 48: 623-646 (2004).
Günther, M., and Ruder, H., "Synthesis of Two-Dimensional Human Walking: a test of the λ-model," *Biol. Cybern.*, 89: 89-106 (2003).
Haimes, Y.Y., et al., "On a Bicriterion Formulation of THe Problems of Integrated System Identification and System Optimization," *IEEE Transactions on Systems, Man and Cybernetics*, 1(3):296-297 (1971).
Hanafusa, et al., "A Robot Hand with Elastic Fingers and Its Application to Assembly Process," pp. 337-359, Robot Motion, Brady, et al., MIT Press, Cambridge, MA 1982.
Hansen, A.H., et al., "The Human Ankle During Walking: Implications for Design of Biomimetic Ankle Prostheses," *Journal of Biomechanics*, 37: 1467-1474 (2004).
Hargrove, L.J., et al., "Real-Time myoelectric control of knee and ankle motions for transfemoral amputees," *JAMA: The Journal of the American Medical Association*, 305(15):1542-1544 (Apr. 2011).
Hargrove, L.J., et al., "Toward the development of a neural interface for lower limb prosthesis control," *Conference Proceedings: Annual International Conference of the IEEE Engineering in Medicine and Biology Society. IEEE Engineering in Medicine and Biology Society. Conference*, 2009:2111-2114, (2009). PMID: 19964782.
Hase, K., et al., "Computer Simulation Study of Human Locomotion with a Three-Dimensional Entire-Body Neuro-Musculo-Skeletal Model, Acquisition of Normal Walking," *JSME Int. J., Series C*, 45(4):1040-1050 (2002).
Hayes, W.C., et al., "Leg Motion Analysis During Gait by Multiaxial Accelerometry: Theoretical Foundations and Preliminary Validations," *Journal of Biomechanical Engineering*, 105: 283-289 (1983).
Heglund, N. et al., "A Simple Design for a Force-Plate to Measure Ground Reaction Forces," *J. Exp. Biol.*, 93: 333-338 (1981).
Hemihelp, "Ankle & Foot Splints or Orthoses," (AFOs), Jun. 2009.
Herbert, R.D., et al., "Change in Length of Relaxed Muscle Fascicles and Tendons with Knee and Ankle Movement in Human," *J. of Physiology*, 539:637-645 (2002).
Herr, H.M. et al., "A Model of Scale Effects in mammalian Quadrupedal Running," *The Journal of Experimental Biology*, 205: 959-967 (2002).
Herr, H.M., and McMahon, T.A., "A Trotting Horse Model," *The International Journal of Robotics Research*, 19: 566-581 (2000).
Herr, H.M., et al., "Bionic Ankle-Foot Prosthesis Normalizes Walking Gait for Persons with Leg Amputation," *Proceedings of the Royal Society, Series B, Biological Sciences*, (2011).
Herr, H.M., and Popovic, M., "Angular Momentum in Human Walking," *The Journal of Experimental Biology*, 211: 467-481 (2008).
Herr, H.M., and Wilkenfeld, A., "User-adaptive Control of A Magnetorheological Prosthetic Knee," *Industrial Robot: An International Journal*, 30(1): 42-55 (2003).
Herr, Hugh et al. "New Horizons for Orthotic and Prosthetic Technology: Artificial Muscle for Ambulation," The MIT Media Laboratory, pp. 1-9, 2004. SPIE Proceedings vol. 5385.
Heyn, A., et al., "The Kinematics of the Swing Phase Obtained From Accelerometer and Gyroscope Measurements," paper presented at the 18th Annual International Conference of the IEEE Engineering in Medicine and Biology Society, Amsterdam (1996).
Hill, A.V., "The Heat of Shortening and the Dynamic Constants of Muscle," *Proc. R. Soc. Lond.*, 126: 136-195 (1938).
Hirai, K., et al., "The Development of Honda Humanoid Robot," paper presented at the IEEE International Conference on Robotics & Automation, Leuven, Belgium (1998).
Hitt, J.K., et al., "The Sparky (Spring Ankle with Regenerative Kinetics) Project: Design and Analysis of a Robotic Transtibial Prosthesis with Regenerative Kinetics," Proceedings of the ASME International Design Engineering Technical Conferences and Computers and Information in Engineering Conference, vol. 5 Part C, DETC2007-34512, pp. 1587-1596, Las Vegas, Nevada (Sep. 2007).
Hof A.L., et al., "Calf Muscle Moment, Work and Efficiency in Level Walking: Role of Series Elasticity," *J. Biochem.*, 16: 523-537 (1983).

(56) References Cited

OTHER PUBLICATIONS

Hofbaur, M.W., and Williams, B.C., "Mode Estimation of Probabilistic Hybrid Systems," MIT Space Systems and Artificial Intelligence Laboratones and Graz University of Technology, Department of Automatic Control, (No Date given).

Hofbaur, M.W., et al., "Hybrid Diagnosis with Unknown Behavioral Modes," Proceedings of the 13th International Workshop on Principles of Diagnosis (DX02) (2002).

Hofmann, A., et al., "A Sliding Controller for Bipedal Balancing Using Integrated Movement of Contact and Non-Contact Limbs," Proceedings of the 2004 IEEE/RSJ International Conference on Intelligence Robots and Systems, Japan (2004).

Hofmann, A.G., "Robust Execution of Bipedal Walking Tasks From Biomechanical Principles," unpublished doctoral dissertation for Massachusetts Institute of Technology (2006).

Hogan, N., "Impedance Control: An Approach to Manipulation," Dept. of Mechanical Engineering and Labortory of Manufacturing and Productivity, Massachusetts Institute of Technology, Cambridge MA, pp. 304-313 (Jun. 1984).

Hogan, N., "Impedance Control: An Approach to Manipulation: Part II—Implementation," *Journal of Dynamic Systems, Measurement, and Control*, 107: 8-16 (1985).

Hogan, N., "A Review of the Methods of Processing EMG for Use As A Proportional Control Signal," *Biomedical Engineering*, 11(3): 81-86 (1976).

Hogan, N., "Impedance Control: An Approach to Manipulation: Part I—Theory," *Journal of Dynamic Systems, Measurement, and Control*, 107: 1-7 (1985).

Hogan, N., "Impedance Control: An Approach to Manipulation: Part III—Application," *Journal of Dynamics Systems, Measurement and Control*, 107: 17-24 (1985).

Hogan, N. et al., "Myoelectric signal processing: Optimal estimation applied to electromyography—part i: Derivation of the optimal myoprocessor," *Biomedical Engineering, IEEE Transactions on*, BME-27(7):382-395 (Jul. 1980).

Hogan, N., and Buerger, S.P., "Impedance and Interaction Control, Robots and Automation Handbook, Chapter 19, © 2005 by CRC Press LLC, 24 pgs."

Holgate, M.A., et al., "The SPARKy (Spring Ankle with Regenerative Kinetics) Project: Choosing a DC Motor Based Actuation Method," Proceedings of the 2nd Biennial IEEE-EMBS International Conf. on Biomedical Robotics and Biomechatronics, Scottsdale, AZ, pp. 163-168, Oct. 19-22, 2008.

Hollander, K.W. et al., "Adjustable Robotic Tendon using a 'Jack Spring'™," Proceedings of the 2005 IEEE, 9th International Conference on Rehabilitation Robotics, Jun. 28-Jul. 1, 2005, Chicago, IL, USA, pp. 113-118.

Howard, R.D., Thesis: "Joint and Actuator Design for Enhanced Stability in Robotic Force Control," Submitted to the Dep. of Aeronautics and Astronautics on Aug. 8, 1990 in partial fulfillment of the requirements for the degree of Doctor of Philosophy.

Huang, H.-P. et al., "Development of a Myoelectric Discrimination System for a Multi-Degree Prosthetic Hand," Proceedings of the 1999 IEEE, International Conference on Robotics & Automation, Detroit, Michigan, (1999).

Huang, Q. et al., "Planning Walking Patterns for a Biped Robot," *IEEE Transactions on Robotics and Automation*, 17(3): 280-289 (Jun. 2001).

Hultborn, H., "Spinal reflexes, mechanisms and concepts: From Eccles to Lundberg and beyond," *Progress in Neurobiology*, 78: 215-232 (2006).

Ijspeert, A.J. et al., "From swimming to walking with a salamander robot driven by a spinal cord model," *Science* 315(5817):1416-20 (2007).

Ijspeert, A.J., "Central pattern generators for locomotion control in animals and robots: a review," *Preprint of Neural Networks*, vol. 21, No. 4, pp. 642-653 (2008).

International Preliminary Report on Patentability for International Application No. PCT/US2010/047279; "Implementing A Stand-Up Sequence Using A Lower-Extremity Prosthesis Or Orthosis", dated Mar. 15, 2012.

International Search Report and Written Opinion for International Application No. PCT/US2009/055600, "Hybrid Terrain-Adaptive Lower-Extremity Systems", dated Apr. 29, 2010 (23 pages).

International Search Report and Written Opinion for International Application No. PCT/US2010/047279; "Implementing A Stand-Up Sequence Using A Lower-Extremity Prosthesis Or Orthosis", dated Jan. 19, 2011.

International Search Report and Written Opinion for International Application No. PCT/US2011/031105, "Controlling Torque In A Prosthesis Or Orthosis", dated Oct. 11, 2011 (16 pages).

International Search Report and Written Opinion for corresponding International Application No. PCT/US2010/022783, "Model-Based Neuromechanical Controller for a Robotic Leg", dated May 4, 2010.

Ishikawa, M., et al., "Muscle-Tendon Interaction and Elastic Energy Usage in Human Walking," *J. Appl. Physiol.*, 99:603-608 (2005).

Ivashko, D.G et al., "Modeling the spinal cord neural circuitry controlling cat hindlimb movement during locomotion," *Neurocomputing*, 52-54, pp. 621-629 (2003).

Jo, S., "Hierarchical Neural Control of Human Postural Balance and Bipedal Walking and Sagittal Plane," *PhD. Thesis*, MIT, (2007).

Johansson, J.L. et al., "A Clinical Comparison of Variable-Damping and Mechanically Passive Prosthetic Knee Devices," Variable-Damping vs. Mechanically Passive Prosthetic Knees, Am *J Phys Med Rehabil* 84(8): 1-13, (Aug. 2005).

Johnson, C.T. et al., "Experimental Identification of Friction and Its Compensation in Precise, Position Controlled Mechanisms," *IEEE Transactions on Industry Applications*, vol. 28, No. 6, pp. 1392-1398 (Nov./Dec. 1992).

Jonic, S. et al., "Three Machine Learning Techniques for Automatic Determination of Rules to Control Locomotion," *IEEE Transactions on Biomedical Engineering*, vol. 46, No. 3, pp. 300-310 (Mar. 1999).

Kadaba, M.P. et al., "Measurement of Lower Extremity Kinematics During Level Walking," *Journal of Orthopedic Research*, pp. 383-392, 1990.

Kadaba, M.P. et al., "Repeatability of Kinematic, Kinetic, and Electromyographic Data in Normal Adult Gait," *Journal of Orthopedic Research*, pp. 849-860, 1989.

Kajita, S. et al., "A Hop towards Running Humanoid Biped," Proceedings of the 2004 IEEE International Conference on Robotics & Automation, pp. 629-635, 2004.

Kajita, S. et al., "Biped Walking on a Low Friction Floor." Proceedings of the 2004 IEEE/RSJ International Conference on Intelligent Robots & Systems, pp. 3546-3552, Sep. 28-Oct. 2, 2004, Sendai, Japan.

Kajita, S. et al., "Resolved Momentum Control: Humanoid Motion Planning based on the Linear and Angular Momentum," Proceedings of the 2003 IEEE/RSJ International Conference on Intelligent Robots & Systems, pp. 1644-1650 (2003).

Kaneko, K. et al., "Humanoid Robot HRP-2." Proceedings of the 2004 IEEE International Conference on Robotics & Automation, pp. 1083-1090 (Apr. 2004).

Kapti, A.O. et al., "Design and control of an active artificial knee joint," *Mechanism and Machine Theory*, vol. 41, pp. 1477-1485 (2006).

Katic, D. et al., "Survey of Intelligent Control Techniques for Humanoid Robots," *Journal of Intelligent and Robotic Systems*, vol. 37, pp. 117-141 (2003).

Kerrigan, D.C. et al., "A refined view of the determinants of gait: Significance of heel," *Archives of Physical Medicine and Rehabilitation*, vol. 81, Issue 8, pp. 1077-1080 (Aug. 2000).

Kerrigan, D.C. et al., "Quantification of pelvic rotation as a determinant of gait," Archives of Physical Medicine and Rehabilitation, vol. 82, Issue 2, pp. 217-220 (Feb. 2001).

Khatib, O. et al., "Coordination and Decentralized Cooperation of Multiple Mobile Manipulators," *Journal of Robotic Systems*, 13(11): 755-764 (1996).

(56) References Cited

OTHER PUBLICATIONS

Khatib, O. et al., "Whole-Body Dynamic Behavior And Control Of Human-Like Robots," *International Journal of Humanoid Robotics*, vol. 1, No. 1, pp. 29-43 (2004).
Kidder, S.M. et al., "A System for the Analysis of Foot and Ankle Kinematics During Gait," *IEEE Transactions on Rehabilitation Engineering*, vol. 4, No. 1, pp. 25-32 (Mar. 1996).
Kim, J.-H. et al., "Realization of Dynamic Walking for the Humaniod Robot Platform KHR-1," *Advanced Robotics*, 18(7): 749-768, (2004).
Kirkwood, C.A. et al., "Automatic detection of gait events: a case study using inductive learning techniques," *J. Biomed. Eng.*, vol. 11, pp. 511-516 (Nov. 1989).
Kitayama, I. et al., "A Microcomputer Controlled Intelligent A/K Prosthesis—Fundamental Development," Proceedings, Seventh World Congress of ISPO, Jun. 28-Jul. 3, 1992, Chicago, Illinois, USA, 25 pages.
Klute, G.K. et al, "Intelligent transtibial prostheses with muscle-like actuators," 2002 American Physiological Society Intersocicty Meeting: The Power of Comparative Physiology: Evolution, Integration, and Applied, 1 page abstract (No date given).
Klute, G.K. et al., "Artificial Muscles: Actuators for Biorobotic Systems," *The International Journal of Robotics Research*, 21(4): 295-309 (2002).
Klute, G.K. et al., "Artificial Tendons: Biomechanical Design Properties for Prosthetic Lower Limbs," Chicago 2000 World Congress on Medical Physics and Biomedical Engineenng, Chicago on Jul. 24-28, 2000, 4 pages.
Klute, G.K. et al., "Lower Limb Prostheses Powered by Muscle-Like Pneumatic Actuator," Submitted to Oleodinamica e Pneumatica, Publishe Tecniche Nuove, Milamo, Italy, Mar. 15, 2000, 6 pages.
Klute, G.K. et al., "McKibben Artificial Muscles: Pneumatic Actuators with Biomechanical Intelligence," IEEE/ASME 1999 International Conference on Advanced Intelligent Mechatronics, Atlanta, GA, pp. 221-226 (Sep. 1999).
Klute, G.K. et al., "Muscle-Like Pneumatic Actuators for Below-Knee Prostheses," Actuator 2000: 7th International Conference on New Actuators, Bremen, Germany on Jun. 9-21, 2000, pp. 289-292.
Klute, G.K. et al., "Powering Lower Limb Prosthestics with Muscle-Like Actuators," Abstract in: Proceeding of the 1st Annual Meeting of the VA Rehabilitation Research and Development Service. "Enabling Veterans: Meeting the Challenge of Rehabilitation in the Next Millennium," Washington, D.C., p. 52 (Oct. 1998).
Klute, G.K. et al., "Variable Stiffness Prosthesis for Transtibial Amputees," Dept of Veteran Affairs, Seattle, WA USA, 2 pages (2003).
Klute, G.K. et al., "Artificial Muscles: Actuators For Lower Limb Prostheses," Abstract in: Proceedings of the $2^{nd}$ Annual Meeting of the VA Rehabilitation Research and Development Service, Washington, D.C., Feb. 20-22, 2000, p. 107.
Klute, G.K. et al., "Mechanical properties of prosthetic limbs: Adapting to the patient," *Journal of Rehabilitation Research and Development*, vol. 38, No. 3, pp. 299-307 (May/Jun. 2001).
Koganezawa, K. et al., *Biomedical Engineering 1987*, 2.3: Control Aspects of Artificial Leg, pp. 71-85 (1987).
Kondak, K. et al., "Control and Online Computation of Stable Movement for Biped Robots," Proceedings of the 2003 IEEE/RSJ, Int'l Conference on Intelligent Robots and Systems, Las Vegas, Nevada, Oct. 2003, pp. 874-879.
Kostov, A. et al., "Machine Learning in Control of Functional Electrical Stimulation Systems for Locomotion," *IEEE Transactions on Biomedical Engineering*, vol. 42, No. 6, pp. 541-551 (Jun. 1995).
Krishnaswamy, P., "A Computational Framework to Study Neural-Structural Interactions in Human Walking," *Master's Thesis, Massachusetts Institute of Technology*, (2010).
Krishnaswamy, P., et al., "Human Leg Model Predicts Ankle Muscle-Tendon Morphology, State, Roles and Energetics in Walking," *PLoS Comput. Biol.* 7(3)1-16:31001107.doi:10.10371/journal. pcbi.1001107 (Mar. 2011). PMID: 21445231 PMCID: 3060164.

Kuiken, T.A., et al., "Targeted muscle reinnervation for real-time myoelectric control of multifunction artificial arms," *JAMA: The Journal of the American Medical Association*, 301(6):619-628 (Feb. 2009).
Kuo, A.D., "A Simple Model of Bipedal Walking Predicts the Preferred Speed-Step Length Relationship," *Transactions of the ASME*, vol. 123, pp. 264-269 (Jun. 2001).
Kuo, A.D., "Energetics of Actively Powered Locomotion Using the Simplest Walking Model," *Journal of Biomechanical Engineering*, vol. 124, pp. 113-120 (Feb. 2002).
Lafortune, M.A., "Three-Dimensional Acceleration of the Tibia During Walking and Running," *J. Biomechanics*, vol. 24, No. 10, pp. 877-886 (1991).
LeBlanc, M.K. et al., "Generation and Transfer of Angular Momentum in the Javelin Throw," American Society of Biomechanics, Presented at the $20^{th}$ Annual Meeting of the American Society of Biomechanics, Atlanta, Georgia, Oct. 17-19, 1996, 4 pages.
Li, C. et al., "Research and Development of the Intelligently-Controlled Prosthetic Ankle Joint," Proceedings of the 2006 IEEE International Conference on Mechatronics and Automation, Jun. 25-28, 2006, Luoyana, China, pp. 1114-1119.
Lichtwark, G.A., et al., "Interactions between the Human Gastroenemius Muscle and the Achilles Tendon During Incline, Level and Decline Locomotion," *The Journal of Experimental Biology*, 209:4379-4388 (2006).
Light, L.H. et al., "Skeletal Transients on Heel Strike in Normal Walking with Different Footwear," *J. Biomechanics*, vol. 13, pp. 477-480 (1980).
Liu, X. et al., "Development of a Lower Extremity Exoskeleton for Human Performance Enhancement," Proceedings of 2004 IEEE/RSJ International Conference on Intelligent Robots and Systems, Sep. 28-Oct. 2, 2004, Sendai, Japan, 3889-3894.
Lloyd, R. et al., "Kinetic changes associated with load carriage using two rucksack designs," *Ergonomics*, vol. 43, No. 9, pp. 1331-1341 (2000).
Luinge, H.J., *Inertial Sensing of Human Movement*, Twente University Press, Enschede, the Netherlands, 80 pages (Feb. 15, 1973).
Lundberg, A., "Reflex control of stepping," The Norwegian Academy of Science and Letters, The Nansen Memorial Lecture, Oct. 10, 1968, 40 pages.
Ma, S.P., et al., "A Distribution-Moment Model of Energetics in Skeletal Muscle," *J. of Biomechanics*, 24:21-35 (1991).
Macfarlane, P.A. et al., "Gait Compansons for Below-Knee Amputees Using a Flex-Foot(TM) Versus a Conventional Prosthetic Foot," JPO 1991, vol. 3, No. 4, p. 150, htt://www.oandp.org/jpo/library/printArticle.asp?printArticleId=1991_04_150, Retrieved on: Feb. 9, 2012, 10 pages.
MacKinnon, C., et al., "Control of Whole Body Balance in the Frontal Plane During Human Walking," *J. Biomech.*, 26(6):633-644 (1993).
Maganaris, C.N., "Force-length characteristics of in vivo human skeletal muscle," *Acta Physiol Scand*, 172: 279-285 (2001).
Maganaris, C.N., "Force-Length Characteristics of the In Vivo Human Gastroenemius Muscle," *Clinical Anatomy*, 16: 215-223 (2003).
Magnusson, S.P., et al., "Increased Cross-Sectional Area and Reduced Tensile Stress of the Achilles Tendon in Elderly Compared with Young Women," *J. of Gerontology: Biological Sciences*, 58A(2):123-127 (2003).
Markowitz, J., et al., "Speed Adaptation in a Powered Transtibial Prosthesis Controlled with a Neuromuscular Model," Phil. Trans. R. Soc. B, 366:1621-1631 (2011).
Martens, W.L.J., "Exploring the Information Content and Some Applications of Body Mounted Piezo-Resistive Accelerometers," PhyVision b.v., Gemert, The Netherlands, pp. 9-12, (No date given).
Martínez-Villalpando, E. C., "Design and Evaluation of a Biomimetic Agonist-Antagonist Active Knee Prosthesis." Doctoral dissertation, Massachusetts Institute of Technology (2012).
Maufroy, C. et al., "Towards a general neural controller for quadrupedal locomotion," *Neural Networks*, 21: 667-681 (2008).
Mayagoitia, R.E. et al., "Accelerometer and rate gyroscope measurement of kinematics: an inexpensive alternative to optical motion analysis systems," *Journal of Biomechanics*, 35: 537-542 (2002).

(56) References Cited

OTHER PUBLICATIONS

McFadyen, B.J. et al., "An Integrated Biomechanical Analysis of Normal Stair Ascent and Descent," *J Biomechanics*, vol. 21, No. 9, pp. 733-744 (1988).
McGeer, T., "Passive Dynamic Walking," The International Journal of Robotics Research, 9, pp. 62-88 (1990).
McGeer, T., Chapter 4: "Principles of Walking and Running," *Advances in Comparative and Environmental Physiology*, Chapter 4, pp. 113-139 (1992).
McIntosh, A.S. et al., "Gait dynamics on an inclined walkway," *J. Biomechanics*, vol. 39, Issue 13, pp. 2491-2502 (2006).
McMahon, T.A. et al., "Groucho Running," *J. Appl. Physiol.* 62(6) pp. 2326-2337 (1987).
McMahon, T.A. et al., "The Mechanics of Running: How Does Stiffness Couple with Speed?" *J. Biomechanics*, vol. 23, Suppl. 1, pp. 65-78 (1990).
Mergner, T., et al., "A Multisensory Posture Control Model of Human Upright Stance," *Prog. Brain Res.*, 142:189-201 (2003).
Minassian, K. et al., "Human lumbar cord circuitries can be activated by extrinsic tonic input to generate locomotor-like activity," *Human Movement Science*, 26: 275-295 (2007).
Mochon, S et al., "Ballistic Walking," *J. Biomechanics*, vol. 13, pp. 49-57 (1980).
Molen, N.H., "Energy/Speed Relation of Below-Knee Amputees Walking on a Motor-Driven Treadmill," *Physiol*, 31: 173-185 (1973).
Morris, J.R.W. "Accelerometry—A Technique for the Measurement of Human Body Movements," *J. Biomechanics*, vol. 6, pp. 729-736 (1973).
Muraoka, T. et al., "Muscle fiber and tendon length changes in the human vastus lateralis during show pedaling," *J. Appl. Physiol.*, 91: 2035-2040 (2001).
Naito, H., et al., "Development of Hip Disarticulation Prostheses Using a Simulator Based on Neuro-Musculo-Skeletal Human Walking Model," *J. Biomechanics Abstract of the 5th World Congress of Biomechanics*, 39 (2006).
Nakagawa, A., "Intelligent Knee Mechanism and the Possibility to Apply the Principle to the Other Joints," paper presented at the Proceedings of the $20^{th}$ Annual International Conference of the IEEE Engineering in Medicine and Biology Society, 20(5): 2282-2287 (1998).
Neal, R. M. et al., "A View of the EM Algorithm That Justifies Incremental, Sparse, and Other Variants," pp. 1-14, (No date given).
Neptune, R., et al., "Modular Control of Human Walking: A simulation Study," *J. of Biomechanics*, 42:1282-1287 (2009).
Neptune R.R., et al., "Forward Dynamics Simulations Provide Insight into Muscle Mechanical Work During Human Locomotion," *Exercise and Sport Science Reviews*, 37:203-210 (2009).
Neptune, R.R., et al., "The Effect of Walking Speed on Muscle Function and Mechanical Energetics," *Gait and Posture*, 28(1):135-143 (2008).
Ng, S.K. et al., "Fuzzy Model Identification For Classification of Gait Events in Paraplegics," IEEE Transactions on Fuzzy Systems, 5(4) (1997).
Nielsen, D.H. et al., "Comparison of Energy Cost and Gait Efficiency during Ambulation in Below-Knee Ampuees Using Different Prosthetic Feet," JPO, 1:24-31, http://www.oandp.org/jpo/library /1989_01_024.asd, Retrieved on: Feb. 7, 2012.
O'Connor, S.M., et al., "Direction Dependent Control of Balance During Walking and Standing," *J. Neurophysiol*, 102:1411-1419 (2009).
Oda, T. et al. "In Vivo Length-Force Relationships on Muscle Fiber and Muscle Tendon Complex in the Tibialis Anterior Muscle," *International Journal of Sport and Health Sciences*, 3:245-252 (2005).
Ogihara, N., and Yamazaki, N., "Generation of Human Bipedal Locomotion by a Bio-Mimetic Neuro-Musculo-Skeletal Model," *Biol. Cybern.*, 84: 1-11 (2001).

Palmer, M.L., "Sagittal Plane Characterization of Normal Human Ankle Function Across A Range of Walking Gait Speeds," Unpublished master's thesis, Massachusetts Institute of Technology, Massachusetts, 71 pages (2002).
Paluska, D., and Herr H., "The Effect of Series Elasticity on Actuator Power and Work Output: Implications for Robotic and Prosthetic Joint Design," Robotics and Autonomous Systems, 54:667-673 (2006).
Paluska, D., and Herr, H., "Series Elasticity and Actuator Power Output," paper presented at the Proceedings of the 2006 IEEE International Conference on Robotics and Automation, 4 pages (May 2006).
Pang, M.Y.C. and Yang. J.F., "The Initiation of the Swing Phase in Human Infact Stepping: Importance of Hip Position and Leg Loading," *Journal of Physiology*, 528(2):389-404 (2000).
Pasch, K.A., et al., "On the drive systems for high performance machines," *AMSE J. Mechanisms, Transmissions, and Automation in Design* 106(1):102-108 (Mar. 1984) may have been cited as dubowski.
Paul, C., et al., "Development of a Human Neuro-Musculo-Skeletal Model for Investigation of Spinal Cord Injury," *Biol. Cybern.*, 93:153-170 (2005).
Pearson, K., et al., "Assessing Sensory Function in Locomotor Systems Using neurp-mechanical Simulations," *Trends in Neurosciences*, 29(11): 626-631 (2006).
Pearson, K.G., "Generating the Walking Gait: Role of Sensory Feedback," *Progress in Brain Research*, 143:123-129 (2004).
Peeraer, L., et al., "Development of EMG-based mode and intent recognition algorithms for a computer-controlled above-knee prosthesis," *J. Biomed. Eng.*, 12: 178-182 (1990).
Perry, J., et al., "Efficiency of Dynamic Elastic Response Prosthetic Feet," *Journal of Rehabilitation Research*, 30(1):137-143 (1993).
Perry, J., et al., "Gait Analysis: Normal and Pathological Function," *SLACK incorporated* (1992).
Petrofsky, J.S., et al., "Feedback Control System for Walking in Man," *Comput. Biol. Med.* 14(2): 135-149 (1984).
Pfeffer, L.E., et al., "Experiments with a Dual-Armed, Cooperative, Flexible-Drivetrain Robot System," paper presented at the IEEE, Aerospace Robotics Laboratory, Department of Aeronautics and Astronautics, Stanford University (1993).
PID Loop Descriptions, National Instruments, http://zone.ni.com/reference/en-XX/help/371093K-01/melvhowto/pidloopdescriptions/, 4 pages, (Aug. 2011).
Popovic, D. and Sinkjaer, T., "Control of Movement for the Physically Disabled: Control for Rehabilitation Technology," (Springer Publisher) pp. 270-302, No date given.
Popovic, D., et al., "Control Aspects of Active Above-Knee Prosthesis," *Int. J. Man-Machine Studies*, 35:751-767 (1991).
Popovic, M., et al., "Angular Momentum Primitives for Human Walking: Biomechanics and Control," paper presented at the Proceedings IEEE/RSJ International Conference on Intelligent Robots and Systems, Sendai, Japan, pp. 1685-1691 (2004).
Popovic, M., et al., "Angular Momentum Regulation During Human Walking: Biomechanics and Control," paper presented at the Proceedings IEEE International Conference on Robotics and Automation, New Orleans, LA, pp. 2405-2411 (2004).
Popovic, M., et al., "Conservation of Angular Momentum During Human Locomotion," *MIT Artificial Intelligence Laboratory*, pp. 231-232 (2002).
Popovic, M.B. and Herr, H., "Global Motion Control and Support Base Planning," MIT pp. 1-8, (No date given).
Popovic, M.B. and Herr, H., "Ground Reference Points in Legged Locomotion: Definitions, Biological Trajectories and Control Implications," *Mobile Robots Towards New Applications*, ISBN 3-86611-314-5, pp. 79-104 (2006).
Popovic, M.B., et al., "Zero Spin Angular Momentum Control: Definition and Applicability," MIT, pp. 1-16, (No date given).
Popovic, M.R., et al., "Gait Identification and Recognition Sensor," paper presented at the Proceedings of $6^{th}$ Vienna International Workshop on Functional Electrostimulation (Sep. 1998).
Pratt, G.A. and Williamson, M.M., "Series Elastic Actuators." Paper presented at the meeting of the IEEE, pp. 399-406 (1995).

(56) References Cited

OTHER PUBLICATIONS

Pratt, G.A., "Legged Robots at MIT: What's New Since Raibert." Paper presented at the meeting of the IEEE, Robotics and Automation Magazine (Sep. 2000).
Pratt, G.A., "Low Impedance Walking Robots," *Integ. and Comp. Biol.*, 42: 174-181 (2002).
Pratt, J.E., et al., "The RoboKnee: An Exoskeleton for Enhancing Strength and Endurance During Walking." Paper presented at the Proceedings of the 2004 IEEE International Conference on Robotics & Automation, New Orleans, LA (Apr. 2004).
Prilutsky, BI, "Work, Energy Expenditure, and Efficiency of the Stretchshorting Cycle." *J. Appl. Biomech.*, 13(4):466-470 (1997).
Prochazka, A. and Yakovenko. S., "The Neuromechanical Tuning Hypothesis," *Progress in Brain Research*, 165: 257-267 (2007).
Prochazka, A., et al., "Positive Force Feedback Control of Muscles," *The American Physiological Society* 77:3226-3236 (1997).
Prochazka, A., et al., "Sensory Control of Locomotion: Reflexes Versus Higher-Level Control," *Sensorimotor Control of Movement and Posture*, pp. 357-367 (2002).
Raibert, M.H., "Legged Robots that Balance," MIT Press, Cambridge, MA, p. 89 (1985).
Ralson, H.J., "Neural Control of Locomotion," *Chapter Energetics of Human Walking*, pp. 399-406, Plenum Press (1976).
Rassier, D.E., et al., "Length Dependence of Active Force Production in Skeletal Muscle," *The American Physiological Society*, pp. 1445-1457 (1999).
Riener, R., et al., "Stair Ascent and Descent at Different Inclinations," *Gait and Posture*, 15: 32-44 (2002).
Rietman, J.S., et al., "Gait Analysis in Prosthetics: Opinions, Ideas and Conclusions," *Prosthetics and Orthotics International*, 26: 50-57 (2002).
Robinson, D.W., "Design and Analysis of Series Elasticity in Closed-Loop Actuator Force Control." Unpublished doctoral dissertation, Massachusetts Institute of Technology (2000).
Robinson, D.W., et al., "Series Elastic Actuator Development for a Biomimetic Walking Robot." Paper presented at the IEEE/ASME International Conf. on Adv. Intelligent Mechatronics (Sep. 19-22, 1999).
Rosen, J., et al., "A Myosignal-Based Powered Exoskeleton System," *IEEE Transaction on Systems, Man, and Cybernetics—Part A: Systems and Humans*, 31(3):210-222 (2001).
Ruina, A., et al., "A Collisional Model of the Energetic Cost of Support Work Qualitatively Explains Leg Sequencing in Walking and Galloping, Pseudo-Elastic Leg Behavior in Running and the Walk-To-Run Transition," *J. of Theoretical Biology*, 237: 170-192 (2005).
Rybak, I.A., et al., "Modelling Spinal Circuitry Involved in Locomotor Pattern Generation: Insights from Deletions During Fictive Locomotion," *J. Physiol.*, 577(2):617-639 (2006).
Rybak, I.A., et al., "Modelling Spinal Circuitry Involved in Locomotor Pattern Generation: Insights from the Effects of Afferent Stimulation," *J. Physiol.*, 577(2):641-658 (2006).
Sanderson, D.J. and Martin. P.E., "Lower Extremity Kinematic and Kinetic Adaptations in Unilateral Below-Knee Amputees During Walking," *Gait & Posture*, 6(2):126-136 (1997).
Sanger, T.D., "Bayesian filtering of myoelectric signals," *Journal of Neurophysiology*, 97(2):1839-1845 (Feb. 2007).
Sanger, T.D., "Human Arm Movements Described by a Low-Dimensional Superposition of Principal Components," *The J. of Neuroscience*, 20(3):1066-1072 (2000).
Saranli, U., et al., "RHex: A Simple and Highly Mobile Hexapod Robot," *The International Journal of Robotics Research*, pp. 616-631 (2001).
Sarrigcorgidis, K. and Kyriakopoulos, K.J., "Motion Control of the N.T.U.A. Robotic Snake on a Planar Surface." Paper presented at the Proceedings of the 1998 IEEE International Conference on Robotics & Automation, Leuven, Belgium (May 1998).
Saxena, S. C., and Mukhopadhyay, P., "E.M.G. operated electronic artificial-leg controller," *Med. & Biol. Eng. & Comput.*, 15: 553-557 (1977).

Schaal, S. and Atkeson, C.G., "Constructive Incremental Learning from Only Local Information," *Neural Computation*, 10(8): 2047-2084 (1998).
Schaal, S., "Is Imitation Learning the Route to Humanoid Robots?", *Trends in Cognitive Sciences*, 3: 233-242 (1999).
Scott, S.H. and Winter, D.A., "Biomechanical Model of the Human Foot: Kinematics and Kinetics During the Stance Phase of Walking," *J Biomechanics*, 26(9): 1091-1104 (1993).
Sentis, L. and Khatib, O., "Task-Oriented Control of Humanoid Robots Through Prioritization." Paper presented at the IEEE-RAS/RSJ International Conference on Humanoid Robots, pp. 1-16 (No date given).
Seyfarth, A., et al., "A Movement Criterion for Running," *J. of Biomechanics*, 35: 649-655 (2002).
Seyfarth, A., et al., "Stable Operation of an Elastic Three-Segment Leg," *Biol. Cybern.*, 84: 365-382 (2001).
Seyfarth, A., et al., "Swing-Leg Retraction: A Simple Control Model for Stable Running," *The J. of Experimental Biology*, 206: 2547-2555 (2003).
Sinkjaer, T., et al., "Major role for sensory feedback in soleus EMG activity in the stance phase of walking in man," *Journal of Physiology*, 523.3: 817-827 (2000).
Skinner, H.B., and Effeney, D.J., "Gait Analysis in Amputees," *American Journal of Physical Medicine*, 64(2): 82-89 (1985).
Smidt, G.L., et al., "An Automated Accelerometry System For Gait Analysis," *J. Biomechanics*, 10: 367-375 (1977).
Srinivasan, M., "Energetics of Legged Locomotion: Why is Total Metabolic Cost Proportional to the Cost of Stance Work." ISB XXth Congress—ASB $29^{th}$ Annual Meeting, Cleveland, OH (Jul. 31-Aug. 5, 2003).
Stepien, J., et al., "Activity Levels Among Lower-Limb Amputees: Self-Report Versus Step Activity Monitor," *Arch. Phys. Med. Rehabil.*, 88: 896-900 (2007).
Sugano, S., et al., "Force Control of the Robot Finger Joint equipped with Mechanical Compliance Adjuster," Proceedings of the 1992 IEEE/RSJ International Conference on Intelligent Robots and Systems, Raleigh, NC (Jul. 1992).
Sugihara, T., et al., "Realtime Humanoid Motion Generation through ZMP Manipulation based on Inverted Pendulum Control," Proceedings of the 2002 IEEE International Conference on Robotics & Automation, Washington, DC (May 2002).
Sup, F., et al., "Design and Control of a Powered Transfemoral Prosthesis," *The International Journal of Robotics Research*, 27(2): 263-273 (2008).
Supplementary European Search Report Application No. 10736533.0, dated Aug. 16, 2013.
Supplementary European Search Report Application No. 10736550.0, dated Aug. 1, 2013.
Taga, G., "A Model of the Neuro-Musculo-Skeletal System for Anticipatory Adjustment of Human Locomotion during Obstacle Avoidance," *Biol. Cybern.*, 78:9-17 (1998).
Taga, G., "A model of the neuro-musculo-skeletal system for human locomotion," *Biol. Cybern.*, 73: 97-111 (1995).
Takayuki, F., et al., "Biped Locomotion using Multiple Link Virtual Inverted Pendulum Model," *T.IEE Japan*, 120-C (2): 208-214 (2000).
Thoroughman, K., and Shadmehr, R., "Learning of action through adaptive combination of motor primitives," *Nature*, 407: 742-747(2000).
Tomović, R., and McHee, R.B., "A Finite State Approach to the Synthesis of Bioengineering Control Systems," *IEEE Transactions on Human Factors in Electronics*, 7(2): 65-69 (1966).
Tong, K., and Granat, M., "A practical gait analysis system using gyroscopes," *Medical Engineering & Physics*, 21: 87-94 (1999).
Türker, K., "Electromyography: Some Methodological Problems and Issues," *Phys. Ther.*, 73: 698-710 (1993).
Umberger, B.R., et al., "Mechanical Power and Efficiency of Level Walking with Different Stride Rates," *J. of Experimental Biology*, 210:3255-3265 (2007).
Van den Bogert, A. J., "Exotendons for Assistance of Human Locomotion," Biomedical Engineering OnLine, BioMed Central, 2(17):1-8 (2003).

(56) References Cited

OTHER PUBLICATIONS

Van den Bogert, A. J., et al., "A Method for Inverse Dynamic Analysis Using Accelerometry," *J. Biochemechanics*, 29(7): 949-954 (1996).

Veltink, P.H., et al., "The Feasibility of Posture and Movement Detection by Accelerometry," paper presented at the IEEE meeting (1993).

Visser, J. J., et al., "Length and Moment Arm of Human Leg Muscles as a Function of Knee and Hip-Joint Angles," *Eur. J. Appl. Physiol.*, 61:453-460 (1990).

Vukobratovic, M., and Juricic, D., "Contribution to the Synthesis of Biped Gait," paper presented at the IEEE Transactions on Bio-Medical Engineering, BME-16(1) (Jan. 1969).

Vukobratovic, M., and Stepanenko, J., Mathematical Models of General Anthropomorphic Systems, *Mathematical Biosciences*, 17: 191-242 (1973).

Walsh, C.J., et al., "Biomimetic Design of an Under-Actuated Leg Exoskeleton for Load-Carrying Augmentation," Unpublished Master's thesis, Massachusetts Institute of Technology, Cambridge, MA (2006).

Wang, J., "EMG Control of Prosthetic Ankle Plantar Flexion," *MIT Master's Thesis* (2011).

Waters, R.L., et al., "Energy Cost of Walking of Amputees: The Influence of Level of Amputation," *The Journal of Bone and Joint Surgery*, 58A(1): 42-46 (1976).

Wilkenfeld, A., "Biologically Inspired Autoadaptive Control of a Knee Prosthesis," unpublished doctoral dissertation, Massachusetts Institute of Technology, Cambridge, MA (2000).

Wilkenfeld, A., and Herr, H., "An Auto-Adaptive External Knee Prosthesis," MIT Lab., (No date given).

Willems, P.A., et al., "External, Internal and Total Work in Human Locomotion," *J. of Experiment Biology*, 198:379-393 (1995).

Willemsen, A.Th.M., et al., "Automatic Stance-Swing Phase Detection from Accelerometer Data for Peroneal Nerve Stimulation," presented at the meeting of IEEE Transactions on Biomedical Engineering, 37(12):1201-1208 (1990).

Willemsen, A.Th.M., et al., "Real-Time Gait Assessment Utilizing A New Way of Accelerometry," *J. Biomechanics*, 23(8):859-863 (1990).

Williams, B.C., et al., "Mode Estimation of Model-Based Programs: Monitoring Systems with Complex Behavior," paper submitted to Massachusetts Institute of Technology, Cambridge, MA, (No date given).

Williamson, M.M., "Series Elastic Actuators," A.I. Technical Report # 1524 submitted to Massachusetts Institute of Technology, Cambridge, Massachusetts (Jan. 1995).

Winter, D.A., "Biomechanical Motor Patterns in Normal Walking," *J. of Motor Behavior*, 15(4):302-330 (1983).

Winter, D.A., "Energy Generation and Absorption at the Ankle and Knee during Fast, Natural, and Slow Cadences," *Clinical Orthopedics and Related Research*, 175: 147-154 (1983).

Winter, D.A., and Robertson, D.G.E., "Joint Torque and Energy Patterns in Normal Gait," Biol. Cybernetics, 29:137-142 (1978).

Winter, D.A., and Sienko, S.E., "Biomechanics of Below-Knee Amputee Gait," *J. Biomechanics*, 21(5):361-367 (1988).

Wisse, M., "Essentials of Dynamic Walking: Analysis and Design of Two-legged Robots," 195 pgs, (2004).

Woodward, M.I. and Cunningham, J.L., "Skeletal Accelerations Measured During Different Exercises," *Proc. Instn. Mech. Engrs.*, 207: 79-85 (1993).

Wu, G. and Ladin, Z., "The Study of Kinematic Transients in Locomotion Using the Integrated Kinematic Sensor," *IEEE Transactions on Rehabilitation Engineering*, 4(3):193-200 (1996).

Yakovenko, S., et al., "Contribution of Stretch Reflexes to Locomotor Control: A Modeling Study," *Biol. Cybern.*, 90: 146-155 (2004).

Yamaguchi, G.T., et al., "A Survey of Human Musculotendon Actuator Parameters," *Technical Report: Multiple Muscle Systems Biomechanics and Movement Organization*, (1990).

Yun, X., "Dynamic State Feedback Control of Constrained Robot Manipulators." Paper presented at the Proceedings of the 27$^{th}$ Conference on Decision and Control, Austin, TX (Dec. 1988).

Zajac, F.E., "Muscle and tendon: properties, models, scaling, and application to biomechanics and motor control," *Critical Reviews in Biomedical Engineering*, 17(4):359-411 (1989).

Ziegler-Graham, K., et al., "Estimating the Prevalence of Limb Loss in the United States, 2005 to 2050," *Archives of Physical Medicine and Rehabilitation*, 89(3):422-429 (2008).

Zlatnik, D., et al., "Finite-State Control of a Trans-Femoral (TF) Prosthesis," *IEEE Transactions on Control Systems Technology*, 10(3): 408-420 (2002).

\* cited by examiner

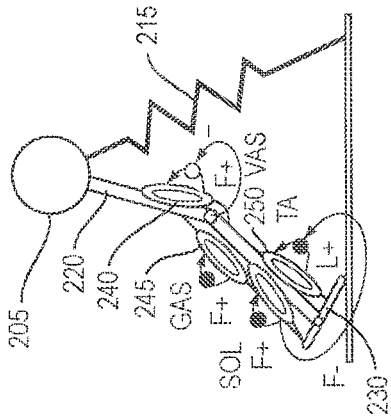
FIG. 2A
FIG. 2B
FIG. 2C
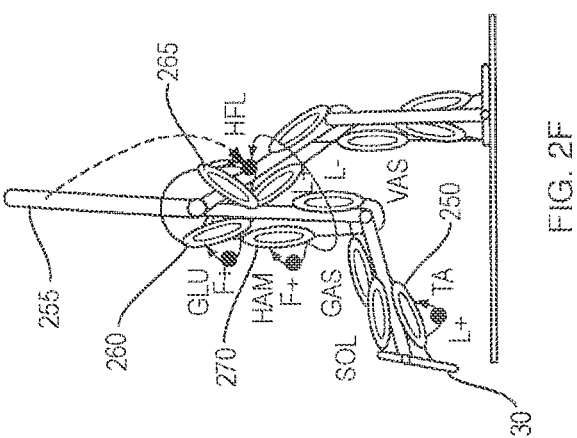
FIG. 2D
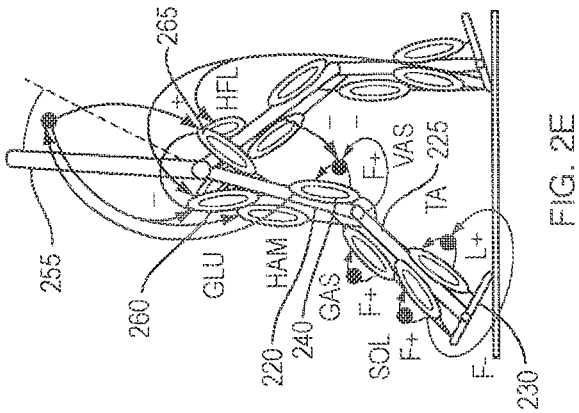
FIG. 2E
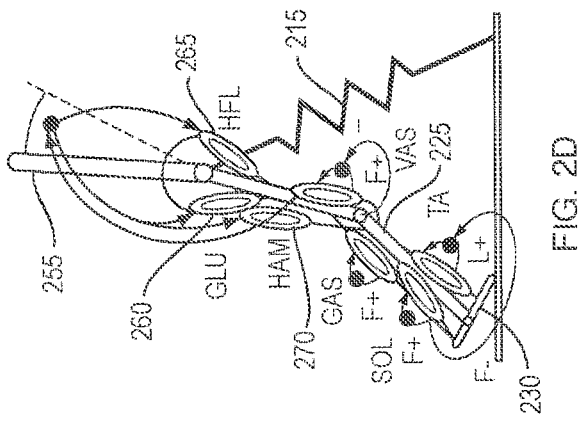
FIG. 2F

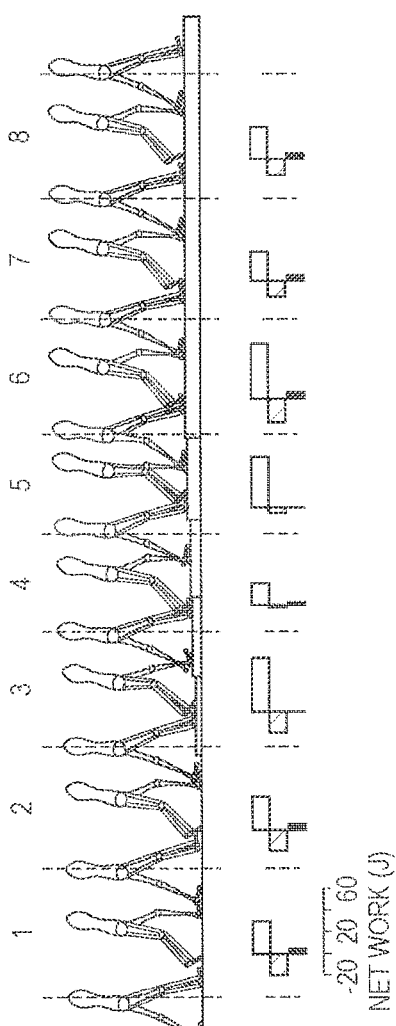
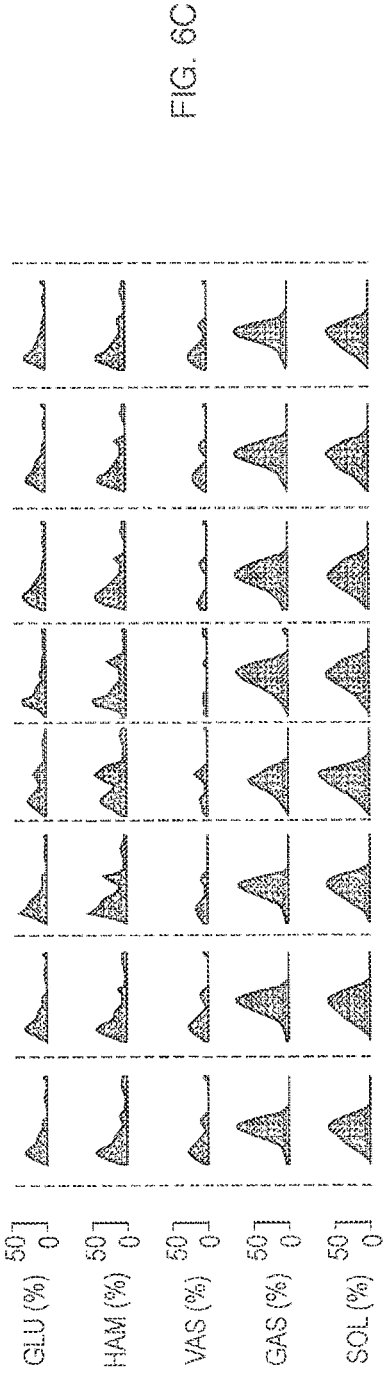
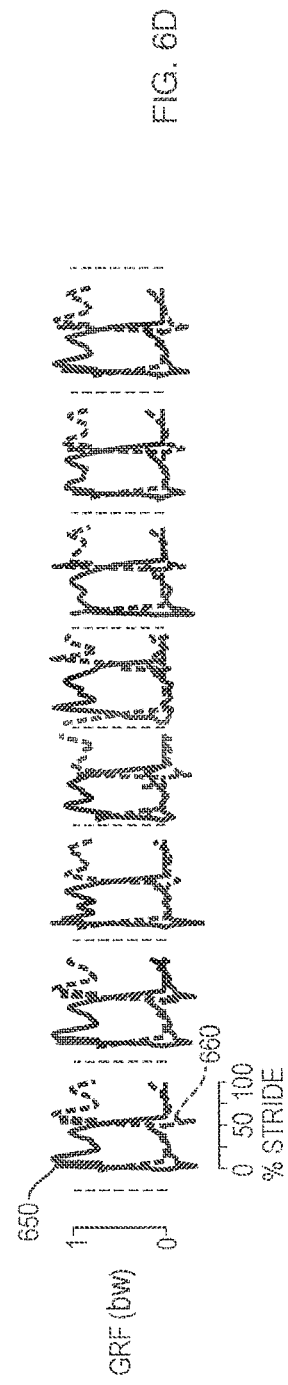
FIG. 6A
FIG. 6B
FIG. 6C
FIG. 6D

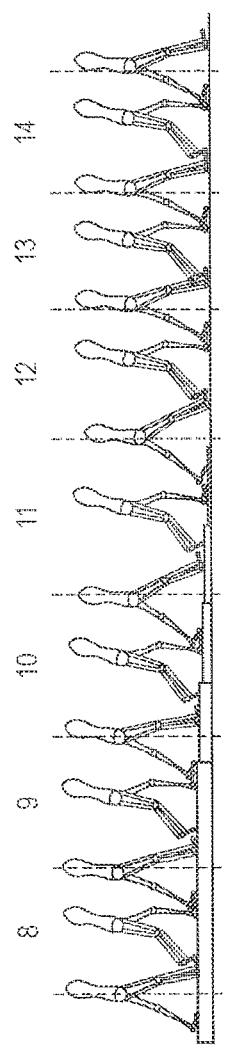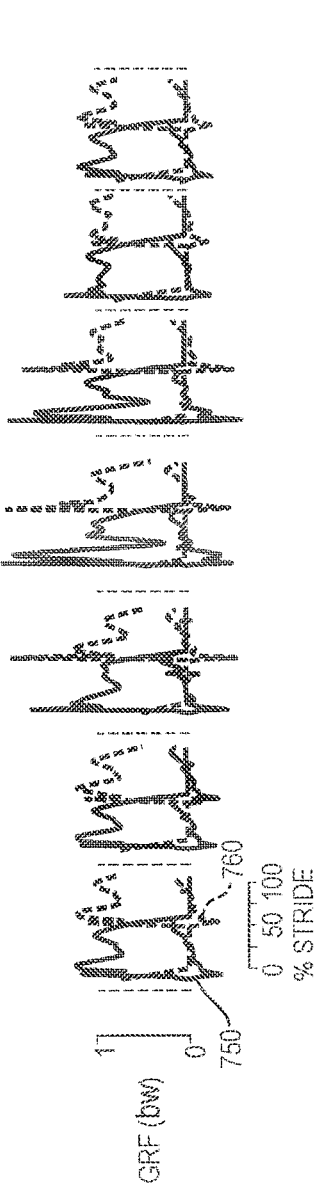

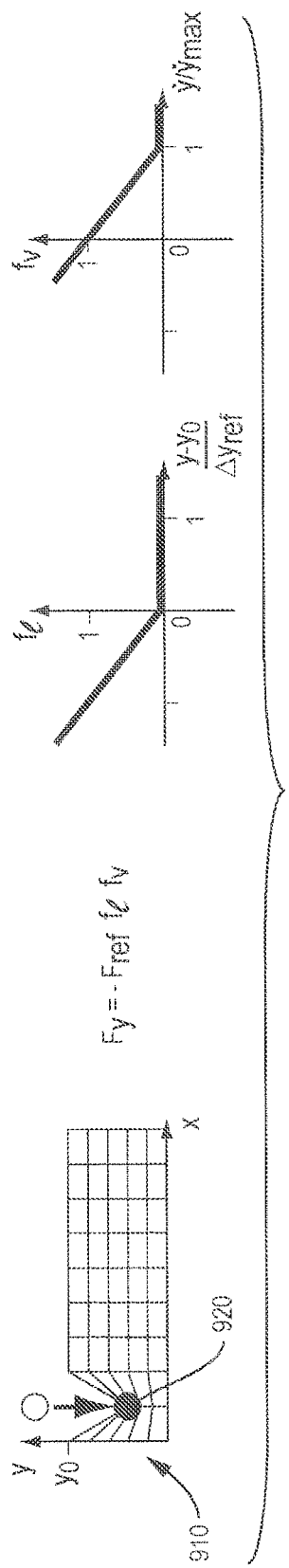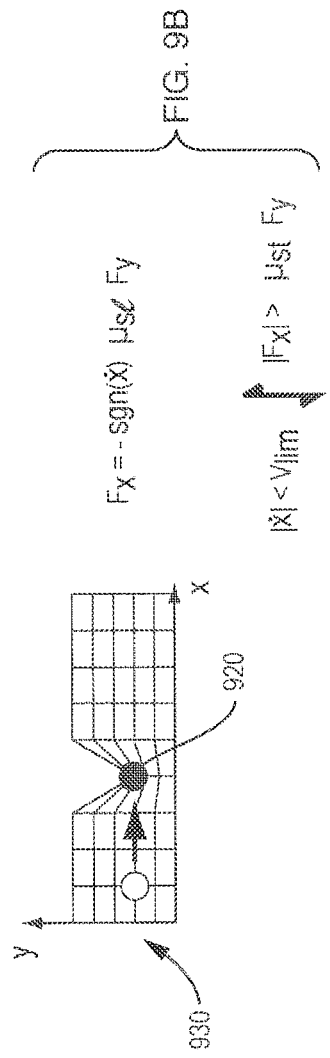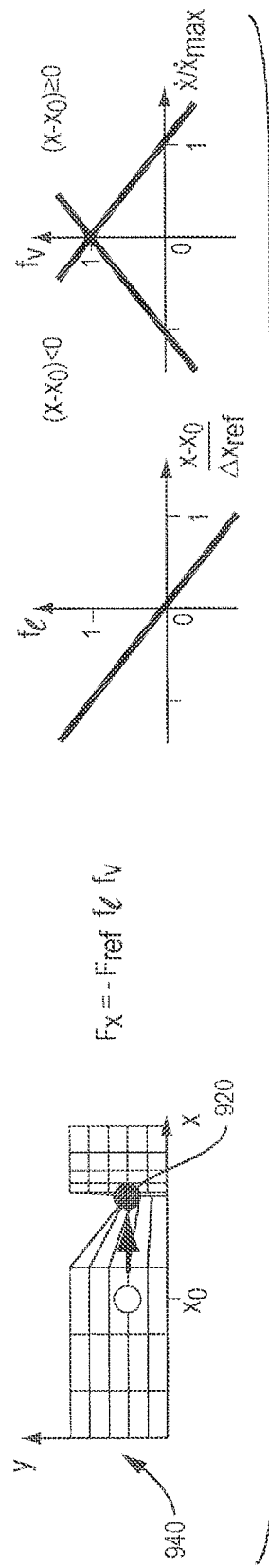

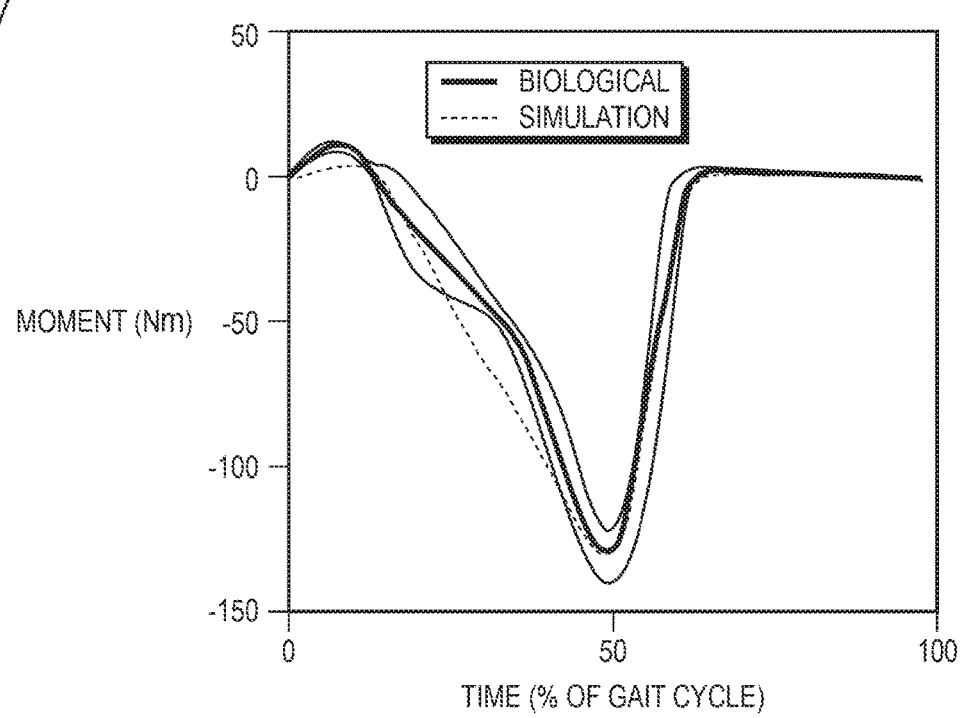
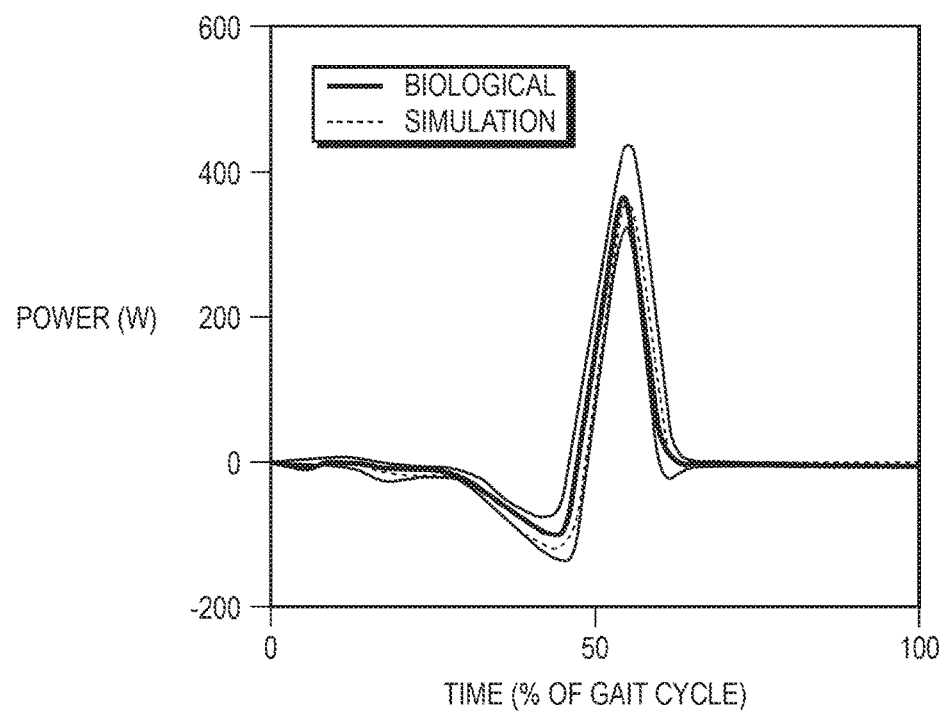
FIG. 29B

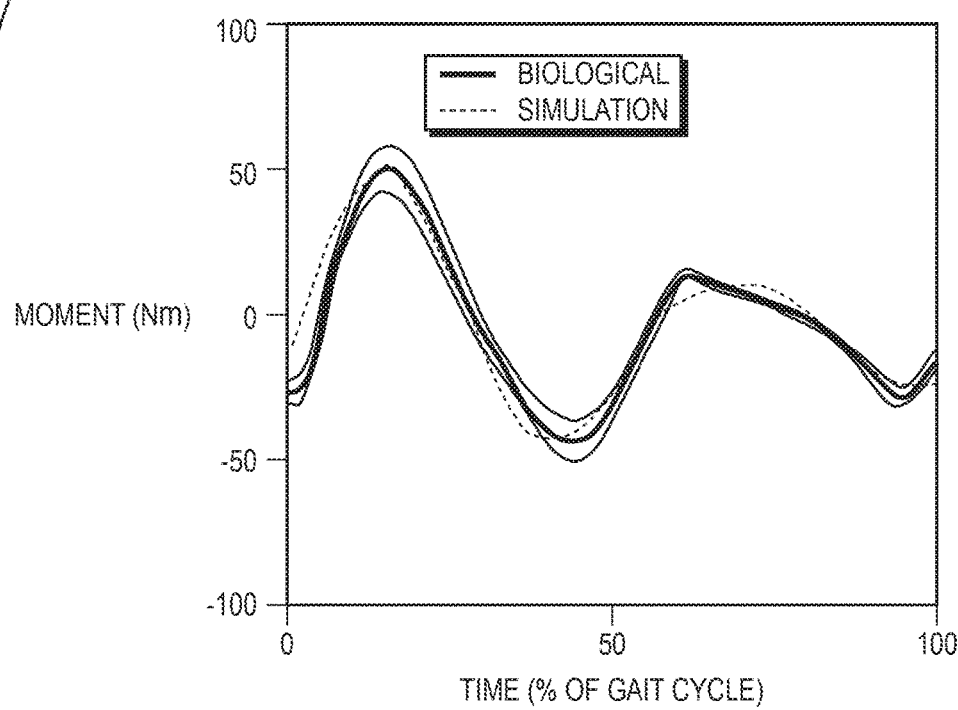
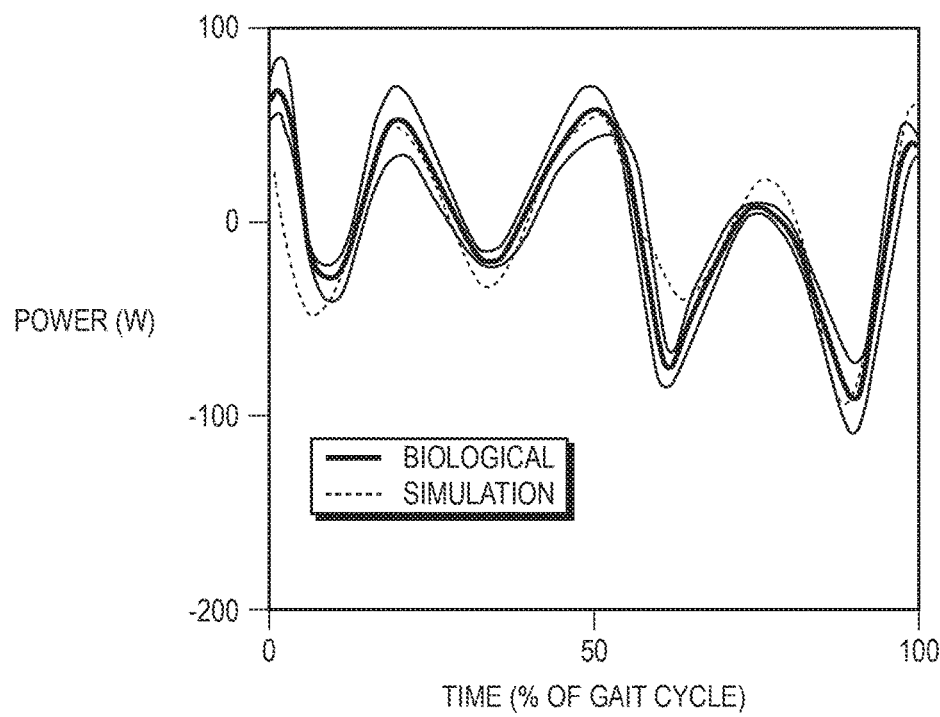
FIG. 29C

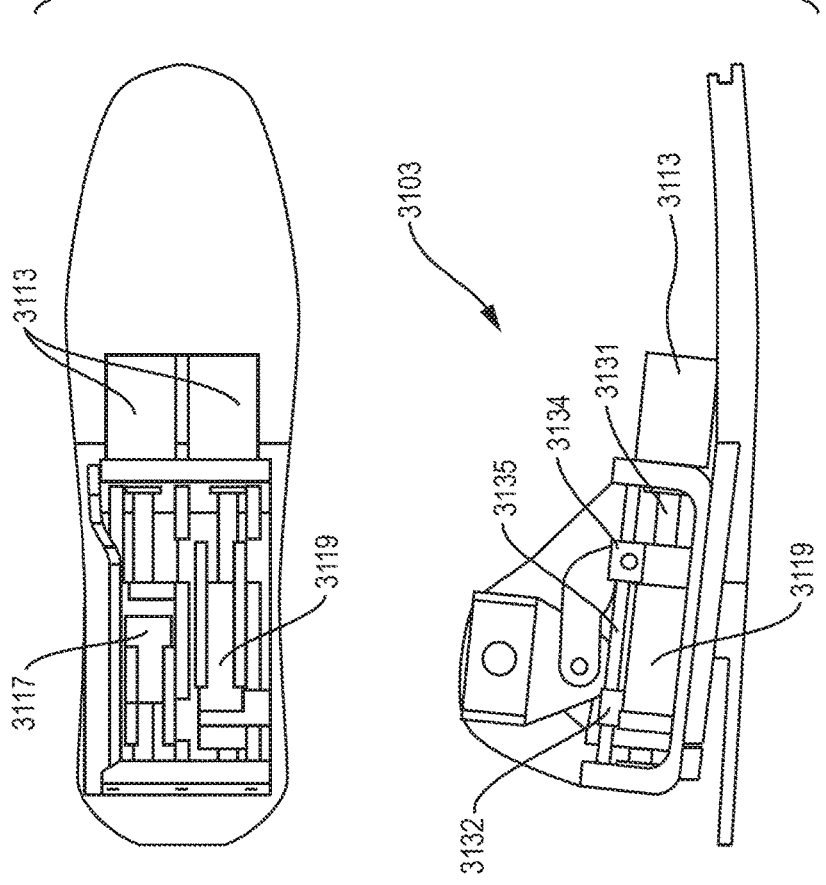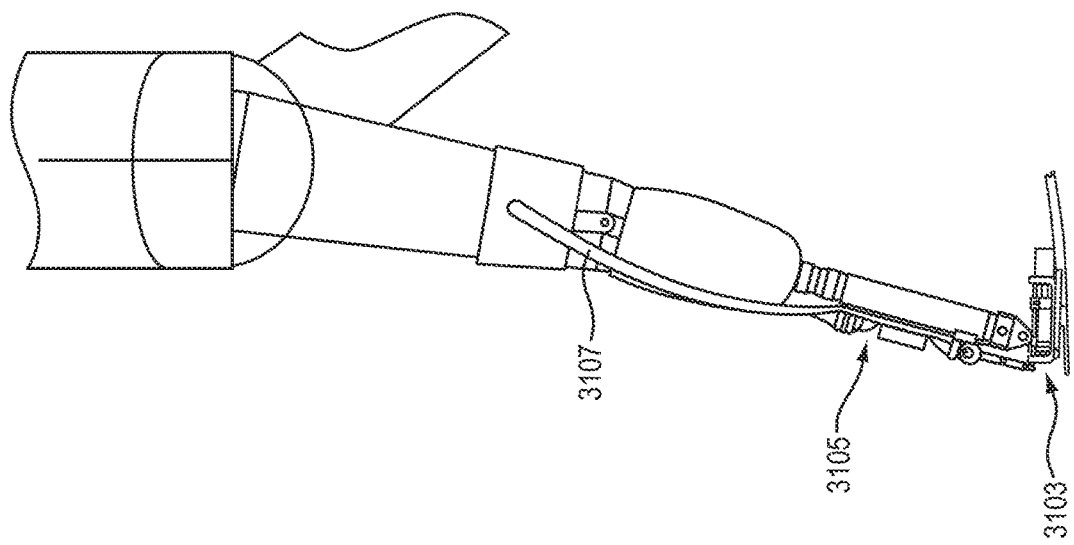

US 11,491,032 B2

ARTIFICIAL JOINTS USING AGONIST-ANTAGONIST ACTUATORS

RELATED APPLICATIONS

This application is a continuation application of U.S. patent application Ser. No. 15/342,661, filed Nov. 3, 2016, which is a continuation of U.S. patent application Ser. No. 14/520,091, filed Oct. 21, 2014, now U.S. Pat. No. 9,539,117, which is a divisional of U.S. patent application Ser. No. 12/698,128, filed Feb. 1, 2010, now U.S. Pat. No. 8,864,846, which claims the benefit of U.S. Provisional Patent Appl. Ser. No. 61/148,545, filed Jan. 30, 2009, and is a continuation-in-part of U.S. patent application Ser. No. 12/608,627, filed Oct. 29, 2009, now U.S. Pat. No. 8,870,967, which is a continuation of U.S. patent application Ser. No. 11/642,993, filed Dec. 19, 2006, now abandoned, which claims the benefit of the U.S. Provisional Patent Appl. Ser. No. 60/751,680, filed Dec. 19, 2005, and is a continuation-in-part of U.S. patent application Ser. No. 11/600,291, filed Nov. 15, 2006, now abandoned, which claims the benefit of U.S. Provisional Appl. No. 60/736,929, filed Nov. 15, 2005 and U.S. Provisional Appl. No. 60/705,651, filed Aug. 4, 2005, and is a continuation-in-part of U.S. patent application Ser. No. 11/395,448, filed Mar. 31, 2006, now abandoned, which claims the benefit of U.S. Provisional Patent Appl. No. 60/666,876, filed Mar. 31, 2005, and of U.S. Provisional Patent Appl. No. 60/704,517, filed Aug. 1, 2005, and U.S. patent application Ser. No. 11/600,291, filed Nov. 15, 2006, now abandoned, is a continuation-in-part of U.S. patent application Ser. No. 11/499,853, filed Aug. 4, 2006, now U.S. Pat. No. 7,313,463, which claims the benefit of U.S. Provisional Appl. 60/705,651, filed Aug. 4, 2005.

U.S. patent application Ser. No. 11/499,853, filed Aug. 4, 2006, now U.S. Pat. No. 7,313,463 is a continuation-in-part of U.S. patent application Ser. No. 11/395,448, filed Mar. 31, 2006, now abandoned, which claims the benefit of U.S. Provisional Appl. No. 60/704,517, filed Aug. 1, 2005, and U.S. Provisional Appl. No. 60/666,876, filed Mar. 31, 2005.

U.S. patent application Ser. No. 12/698,128, filed Feb. 1, 2010, now U.S. Pat. No. 8,864,846, is also a continuation-in-part of U.S. patent application Ser. No. 12/157,727, filed Jun. 12, 2008, now U.S. Pat. No. 8,512,415, which claims the benefit of U.S. Provisional Appl. No. 60/934,223, filed Jun. 12, 2007, and is a continuation-in-part of U.S. patent application Ser. No. 11/642,993, filed Dec. 19, 2006, now abandoned.

The present application claims the benefit of the filing date of each of the foregoing patent applications and incorporates the disclosures of each of the foregoing applications herein by reference in their entirety.

GOVERNMENT SUPPORT

This invention was made with U.S. government support under Grant Numbers VA241-P-0026; 650D70025 and VA241-P-0479, 650-D85022, awarded by the United States Veterans Administration. The government has certain rights in this invention.

FIELD OF THE TECHNOLOGY

The present invention relates to control of artificial joints and limbs for use in prosthetic, orthotic, exoskeletal, or robotic devices and, in particular, to control methodology for a robotic leg based on a neuromuscular model of locomotion.

BACKGROUND OF THE INVENTION

Legged locomotion of animals and humans is controlled by a complex network of neurons. Proposed in the early 20th century [Brown, T. G., 1914. On the nature of the fundamental activity of the nervous centres; together with an analysis of the conditioning of rhythmic activity in progression, and a theory of the evolution of function in the nervous system. J Physiol 48 (1), 18-46.]. and firmly established today [Orlovsky, G., Deliagina, T., Grillner, S., 1999. Neuronal control of locomotion: from mollusc to man. Oxford University Press, New York], the central pattern generator (CPG) forms the basis of this network.

In the current view, the CPG consists of layers of neuron pools in the spinal cord [Rybak, I. A., Shevtsova, N. A., Lafreniere-Roula, M., McCrea, D. A., 2006. Modelling spinal circuitry involved in locomotor pattern generation: insights from deletions during fictive locomotion. J Physiol 577 (Pt 2), 617-639] which, through other neuron pools channeling muscle synergies, provide rhythmic activity to the leg extensor and flexor muscles [Dietz, V., 2003. Spinal cord pattern generators for locomotion. Clin Neurophysiol 114 (8), 1379-1389; Minassian, K., Persy, I., Rattay, F., Pinter, M. M., Kern, H., Dimitrijevic, M. R., 2007. Human lumbar cord circuitries can be activated by extrinsic tonic input to generate locomotor-like activity. Hum Mov Sci 26 (2), 275-295] sufficient to generate stepping movements, even in the absence of spinal reflexes [Grillner, S., Zangger, P., 1979. On the central generation of locomotion in the low spinal cat. Exp Brain Res 34 (2), 241-261; Frigon, A., Rossignol, S., 2006. Experiments and models of sensorimotor interactions during locomotion. Biol Cybern 95 (6), 607-627]. Spinal reflexes are nevertheless part of this complex network [Rybak, I. A., Stecina, K., Shevtsova, N. A., McCrea, D. A., 2006. Modelling spinal circuitry involved in locomotor pattern generation: insights from the effects of afferent stimulation. J Physiol 577 (Pt 2), 641-658], contributing to the selection of locomotive patterns, the timing of the extensor and flexor activities, and the modulation of the CPG output.

Using this combination of a central pattern generation and modulating reflexes, neuromuscular models of lampreys [Ekeberg, O., Grillner, S., 1999. Simulations of neuromuscular control in lamprey swimming. Philos Trans R Soc Lond B Biol Sci 354 (1385), 895-902], salamanders [Ijspeert, A., Crespi, A., Ryczko, D., Cabelguen, J.-M., 2007. From swimming to walking with a salamander robot driven by a spinal cord model. Science 315 (5817), 1416-1420], cats [Ivashko, D. G., Prilutski, B. I., Markin, S. N., Chapin, J. K., Rybak, I. A., 2003. Modeling the spinal cord neural circuitry controlling cat hindlimb movement during locomotion. Neurocomputing 52-54, 621-629; Yakovenko, S., Gritsenko, V., Prochazka, A., 2004. Contribution of stretch reflexes to locomotor control: a modeling study. Biol Cybern 90 (2), 146-155; Maufroy, C., Kimura, H., Takase, K., 2008. Towards a general neural controller for quadrupedal locomotion. Neural Netw 21 (4), 667-681], and humans [Ogihara, N., Yamazaki, N., 2001. Generation of human bipedal locomotion by a bio-mimetic neuro-musculo-skeletal model. Biol Cybern 84 (1), 1-11; Paul, C., Bellotti, M., Jezernik, S., Curt, A., 2005. Development of a human neuro-musculo-skeletal model for investigation of spinal cord injury. Biol Cybern 93 (3), 153-170] have developed into essential tools for studying different control strategies in animal and human locomotion. The emphasis of these models has been to reproduce the architecture of the CPG and underlying reflexes suggested by experiments [Pearson, K., Ekeberg, O., Buschges, A., 2006. Assessing sensory function in locomotor systems using neuro-mechanical simulations. Trends Neurosci 29 (11), 625-631]. However, little attention has been paid to understanding how such architectures might represent or encode principles of locomotion mechanics.

These principles suggest that, in contrast to the complexity of the identified neural networks, legged locomotion requires little or no control. For instance, two conceptual models of walking [Alexander, R., 1976. Mechanics of bipedal locomotion. In: Perspectives in experimental biology (Ed. Davies, P. S.) Pergamon, Oxford; Mochon, S., McMahon, T., 1980. Ballistic walking. J. Biomech. 13 (1), 49-57] and running [Blickhan, R., 1989. The spring-mass model for running and hopping. J. of Biomech. 22, 1217-1227; McMahon, T., Cheng, G., 1990. The mechanism of running: how does stiffness couple with speed? J. of Biomech. 23, 65-78] have been put forth that capture dominant mechanisms of legged locomotion. Researchers have demonstrated the capacity of these models to self-stabilize if the mechanical system is properly tuned [McGeer, T., 1990. Passive dynamic walking. Int. J. Rob. Res. 9 (2), 62-82; McGeer, T., 1992. Principles of walking and running. Vol. 11 of Advances in Comparative and Environmental Physiology. Springer-Verlag Berlin Heidelberg, Ch. 4; Seyfarth, A., Geyer, H., Günther, M., Blickhan, R., 2002. A movement criterion for running. J. of Biomech. 35, 649-655; Ghigliazza, R., Altendorfer, R., Holmes, P., Koditschek, D., 2003. A simply stabilized running model. SIAM J. Applied. Dynamical Systems 2 (2), 187-218]. Walking and running robots have moreover demonstrated the practical relevance and control benefits derived from this principle [Raibert, M., 1986. Legged robots that balance. MIT press, Cambridge; McGeer, T., 1990. Passive dynamic walking. Int. J. Rob. Res. 9 (2), 62-82; Saranli, U., Buehler, M., Koditschek, D., 2001. Rhex: A simple and highly mobile hexapod robot. Int. Jour. Rob. Res. 20 (7), 616-631; Collins, S., Ruina, A., Tedrake, R., Wisse, M., 2005. Efficient bipedal robots based on passive-dynamic walkers. Science 307 (5712), 1082-1085]. But it remains an open question how this and other principles of legged mechanics are integrated into the human motor control system.

The importance of this interplay between mechanics and motor control has been recognized by neuroscientists and biomechanists alike [Pearson, K., Ekeberg, O., Buschges, A., 2006. Assessing sensory function in locomotor systems using neuro-mechanical simulations. Trends Neurosci 29 (11), 625-631]. For instance, although it is generally accepted that the CPG forms a central drive for motor activity in locomotion [Grillner, S., Zangger, P., 1979. On the central generation of locomotion in the low spinal cat. Exp Brain Res 34 (2), 241-261; Dietz, V., 2003. Spinal cord pattern generators for locomotion. Clin Neurophysiol 114 (8), 1379-1389; Frigon, A., Rossignol, S., 2006. Experiments and models of sensorimotor interactions during locomotion. Biol Cybern 95 (6), 607-627; Ijspeert, A. J., 2008. Central pattern generators for locomotion control in animals and robots: a review. Neural Netw 21 (4), 642-653], Lundberg suggested in 1969 that, out of its rather simple central input, spinal reflexes, which relay information about locomotion mechanics, could shape the complex muscle activities seen in real locomotion [Lundberg, A., 1969. Reflex control of stepping. In: The Nansen memorial lecture V, Oslo: Universitetsforlaget, 5-42]. Refining this idea, Taga later proposed that, because "centrally generated rhythms are entrained by sensory signals which are induced by rhythmic movements of the motor apparatus . . . [,] motor output is an emergent property of the dynamic interaction between the neural system, the musculo-skeletal system, and the environment" [Taga, G., 1995. A model of the neuro-musculo-skeletal system for human locomotion. I. Emergence of basic gait. Biol. Cybern. 73 (2), 97-111]. In support, he presented a neuromuscular model of human locomotion that combines a CPG with sensory feedback and demonstrates how basic gait can emerge from the global entrainment between the rhythmic activities of the neural and of the musculo-skeletal system.

What the actual ratio of central and reflex inputs is that generates the motor output continues to be debated [Pearson, K. G., 2004. Generating the walking gait: role of sensory feedback. Prog Brain Res 143, 123-129; Frigon, A., Rossignol, S., 2006. Experiments and models of sensorimotor interactions during locomotion. Biol Cybern 95 (6), 607-627; Hultborn, H., 2006. Spinal reflexes, mechanisms and concepts: from Eccles to Lundberg and beyond. Prog Neurobiol 78 (3-5), 215-232; Prochazka, A., Yakovenko, S., 2007. The neuromechanical tuning hypothesis. Prog Brain Res 165, 255-265]. For instance, for walking cats, it has been estimated that only about 30 percent of the muscle activity observed in the weight bearing leg extensors can be attributed to muscle reflexes [Prochazka, A., Gritsenko, V., Yakovenko, S., 2002. Sensory control of locomotion: reflexes versus higher-level control. Adv Exp Med Biol 508, 357-367; Donelan, J. M., McVea, D. A., Pearson, K. G., 2009. Force regulation of ankle extensor muscle activity in freely walking cats. J Neurophysiol 101 (1), 360-371].

In humans, the contribution of reflexes to the muscle activities in locomotion seems to be more prominent. Sinkjaer and colleagues estimated from unloading experiments that reflexes contribute about 50 percent to the soleus muscle activity during stance in walking [Sinkjaer, T., Andersen, J. B., Ladouceur, M., Christensen, L. O., Nielsen, J. B., 2000. Major role for sensory feedback in soleus EMG activity in the stance phase of walking in man. J Physiol 523 Pt 3, 817-827]. More recently, Grey and colleagues found that the soleus activity changes proportionally to changes in the Achilles tendon force, suggesting a direct relationship between positive force feedback and activity for this muscle [Grey, M. J., Nielsen, J. B., Mazzaro, N., Sinkjaer, T., 2007. Positive force feedback in human walking. J Physiol 581 (1), 99-105]. Whether such a large reflex contribution is present for all leg muscles remains open. Perhaps a proximo-distal gradient exists in motor control where proximal leg muscles are mainly controlled by central inputs while distal leg muscles are dominated by reflex inputs due to higher proprioceptive feedback gains and a larger sensitivity to mechanical effects, as Daley and colleagues concluded from locomotion experiments with birds [Daley, M. A., Felix, G., Biewener, A. A., 2007. Running stability is enhanced by a proximo-distal gradient in joint neuromechanical control. J Exp Biol 210 (Pt 3), 383-394].

Adaptation to terrain is an important aspect of walking. Today's commercially-available ankle-foot prostheses utilize lightweight, passive structures that are designed to present appropriate elasticity during the stance phase of walking [S. Ron, Prosthetics and Orthotics: Lower Limb and Spinal. Lippincott Williams & Wilkins 2002]. The advanced composites used in these devices permit some energy storage during controlled dorsiflexion and plantar flexion, and subsequent energy release during powered plantar flexion, much like the Achilles tendon in the intact human [A. L. Hof, B. A. Geelen, Jw. Van den Berg, "Calf muscle moment, work and efficiency in level walking; role of series elasticity," Journal of Biomechanics, Vol. 16, No. 7, pp. 523-537, 1983; D. A. Winter, "Biomechanical motor pattern in normal walking," Journal of Motor Behavior, Vol. 15, No. 4, pp. 302-330, 1983].

Although this passive-elastic behavior is a good approximation to the ankle's function during slow walking, normal and fast walking speeds require the addition of external energy, and thus cannot be implemented by any passive ankle-foot device [M. Palmer, "Sagittal plane characterization of normal human ankle function across a range of walking gait speeds," Master's Thesis, Massachusetts Institute of Technology, Cambridge, Mass., 2002; D. H. Gates, "Characterizing ankle function during stair ascent, descent, and level walking for ankle prosthesis and orthosis design," Master's Thesis, Boston University, 2004; A. H. Hansen, D. S. Childress, S. C. Miff, S. A. Gard, K. P. Mesplay, "The human ankle during walking: implication for the design of biomimetic ankle prosthesis," Journal of Biomechanics, Vol. 37, Issue 10, pp. 1467-1474, 2004]. This deficiency is reflected in the gait of transtibial amputees using passive ankle-foot prostheses. Their self-selected walking speed is slower, and stride length shorter, than normal [D. A. Winter and S. E. Sienko. "Biomechanics of below-knee amputee gait," Journal of Biomechanics, 21, pp. 361-367, 1988]. In addition, their gait is distinctly asymmetric: the range of ankle movement on the unaffected side is smaller [H. B. Skinner and D. J. Effeney, "Gait analysis in amputees," Am J Phys Med, Vol. 64, pp. 82-89, 1985; H. Bateni and S. Olney, "Kinematic and kinetic variations of below-knee amputee gait," Journal of Prosthetics & Orthotics, Vol. 14, No. 1, pp. 2-13, 2002], while, on the affected side, the hip extension moment is greater and the knee flexion moment is smaller [D. A. Winter and S. E. Sienko. "Biomechanics of below-knee amputee gait," Journal of Biomechanics, 21, pp. 361-367, 1988; H. Bateni and S. Olney, "Kinematic and kinetic variations of below-knee amputee gait," Journal of Prosthetics & Orthotics, Vol. 14, No. 1, pp. 2-13, 2002]. They also expend greater metabolic energy walking than non-amputees [N. H. Molen, "Energy/speed relation of below-knee amputees walking on motor-driven treadmill," Int. Z. Angew, Physio, Vol. 31, p 173, 1973; G. R. Colborne, S. Naumann, P. E. Longmuir, and D. Berbrayer, "Analysis of mechanical and metabolic factors in the gait of congenital below knee amputees," Am. J. Phys. Med. Rehabil., Vol. 92, pp 272-278, 1992; R. L. Waters, J. Perry, D. Antonelli, H. Hislop. "Energy cost of walking amputees: the influence of level of amputation," J Bone Joint Surg. Am., Vol. 58, No. 1, pp. 4246, 1976; E. G. Gonzalez, P. J. Corcoran, and L. R. Rodolfo. Energy expenditure in B/K amputees: correlation with stump length. Archs. Phys. Med. Rehabil. 55, 111-119, 1974; D. J. Sanderson and P. E. Martin. "Lower extremity kinematic and kinetic adaptations in unilateral below-knee amputees during walking," Gait and Posture. 6, 126 136, 1997; A. Esquenazi, and R. DiGiacomo. "Rehabilitation After Amputation," Journ Am Podiatr Med Assoc, 91(1): 13-22, 2001]. These differences could possibly be a result of the amputees' greater use of hip power to compensate for the lack of ankle power [A. D. Kuo, "Energetics of actively powered locomotion using the simplest walking model," J Biomech Eng., Vol. 124, pp. 113-120, 2002; A. D. Kuo, J. M. Donelan, and A. Ruina, "Energetic consequences of walking like an inverted pendulum: Step-sto-step transitions," Exerc. Sport Sci. Rev., Vol. 33, No. 2, pp. 88-97, 2005; A. Ruina, J. E. Bertram, and M. Srinivasan, "A collisional model of the energetic cost of support work qualitatively explains leg sequencing in walking and galloping, pseudo-elastic leg behavior in running and the walk-to-run transition." J. Theor. Biol., Vol. 237, No. 2, pp. 170-192, 2005].

Passive ankle-foot prostheses cannot provide the capability of adaptation to terrain. To provide for a normal, economical gait beyond slow walking speeds, powered ankle-foot prostheses have now been developed [S. Au and H. Herr. "Initial experimental study on dynamic interaction between an amputee and a powered ankle-foot prosthesis," Workshop on Dynamic Walking: Mechanics and Control of Human and Robot Locomotion, Ann Arbor, Mich., May 2006; S. K. Au, J. Weber, and H. Herr, "Biomechanical design of a powered ankle-foot prosthesis," Proc. IEEE Int. Conf. On Rehabilitation Robotics, Noordwijk, The Netherlands, pp. 298-303, June 2007; S. Au, J. Weber, E. Martinez-Villapando, and H. Herr. "Powered Ankle-Foot Prosthesis for the Improvement of Amputee Ambulation," IEEE Engineering in Medicine and Biology International Conference. August 23-26, Lyon, France, pp. 3020-3026, 2007; H. Herr, J. Weber, S. Au. "Powered Ankle-Foot Prosthesis," Biomechanics of the Lower Limb in Health, Disease and Rehabilitation. September 3-5, Manchester, England, pp. 72-74, 2007; S. K. Au, "Powered Ankle-Foot Prosthesis for the Improvement of Amputee Walking Economy," Ph.D. Thesis, Massachusetts Institute of Technology, Cambridge, Mass., 2007; S. Au, J. Weber, and H. Herr. "Powered Ankle-foot Prosthesis Improves Walking Metabolic Economy," IEEE Trans. on Robotics, Vol. 25, pp. 51-66, 2009; J. Hitt, R. Bellman, M. Holgate, T. Sugar, and K. Hollander, "The sparky (spring ankle with regenerative kinetics) projects: Design and analysis of a robotic transtibial prosthesis with regenerative kinetics," in Proc. IEEE Int. Conf. Robot. Autom., Orlando, Fla., pp 2939-2945, May 2006; S. K. Au, H. Herr, "On the Design of a Powered Ankle-Foot Prosthesis: The Importance of Series and Parallel Elasticity," IEEE Robotics & Automation Magazine. pp. 52-59, September 2008]. Some of these are of size and weight comparable to the intact human ankle-foot, and have the elastic energy storage, motor power, and battery energy to provide for a day's typical walking activity [S. K. Au, H. Herr, "On the Design of a Powered Ankle-Foot Prosthesis: The Importance of Series and Parallel Elasticity," IEEE Robotics & Automation Magazine. pp. 52-59, September 2008].

The use of active motor power in these prostheses raises the issue of control. In previous work with these powered devices, the approach taken was to match the torque-ankle state profile of the intact human ankle for the activity to be performed [S. K. Au, "Powered Ankle-Foot Prosthesis for the Improvement of Amputee Walking Economy," Ph.D. Thesis, Massachusetts Institute of Technology, Cambridge, Mass., 2007; J. Hitt, R. Bellman, M. Holgate, T. Sugar, and K. Hollander, "The sparky (spring ankle with regenerative kinetics) projects: Design and analysis of a robotic transtibial prosthesis with regenerative kinetics," in Proc. IEEE Int. Conf. Robot. Autom., Orlando, Fla., pp 2939-2945, May 2006; F. Sup, A. Bohara, and M. Goldfarb, "Design and Control of a Powered Transfemoral Prosthesis," The International Journal of Robotics Research, Vol. 27, No. 2, pp. 263-273, 2008]. The provision of motor power meant that the open work loops of the angle-torque profiles in faster walking could be supported, rather than just the spring-like behavior provided by passive devices. However, this control approach exhibited no inherent adaptation. Instead, torque profiles were required for all intended activities and variation of terrain, along with an appropriate means to select among them.

In general, existing commercially available active ankle prostheses are only able to reconfigure the ankle joint angle during the swing phase, requiring several strides to converge to a terrain-appropriate ankle position at first ground contact.

Further, they do not provide any of the stance phase power necessary for normal gait, and therefore cannot adapt net stance work with terrain slope. In particular, control schemes for powered ankle-foot prostheses rely upon fixed torque-ankle state relationships obtained from measurements of intact humans walking at target speeds and across known terrains. Although effective at their intended gait speed and terrain, these controllers do not allow for adaptation to environmental disturbances such as speed transients and terrain variation.

Neuromuscular models with a positive force feedback reflex scheme as the basis of control have recently been employed in simulation studies of the biomechanics of legged locomotion [H. Geyer, H. Herr, "A muscle-reflex model that encodes principles of legged mechanics predicts human walking dynamics and muscle activities," (Submitted for publication); H. Geyer, A. Seyfarth, R. Blickhan, "Positive force feedback in bouncing gaits?," Proc. R Society. Lond. B 270, pp. 2173-2183, 2003]. Such studies show promise regarding the need for terrain adaptation.

Biomimetic Hybrid Actuators employed in biologically-inspired musculoskeletal architectures as described in the above noted U.S. patent application Ser. No. 11/395,448 employ an electric motor for supplying positive energy to and storing negative energy from an artificial joint or limb, as well as elastic elements such as springs, and controllable variable damper components, for passively storing and releasing energy and providing adaptive stiffness to accommodate level ground walking as well as movement on stairs and surfaces having different slopes.

The above noted application Ser. No. 11/495,140 describes an artificial foot and ankle joint consisting of a curved leaf spring foot member that defines a heel extremity and a toe extremity, and a flexible elastic ankle member that connects said foot member for rotation at the ankle joint. An actuator motor applies torque to the ankle joint to orient the foot when it is not in contact with the support surface and to store energy in a catapult spring that is released along with the energy stored in the leaf spring to propel the wearer forward. A ribbon clutch prevents the foot member from rotating in one direction beyond a predetermined limit position, and a controllable damper is employed to lock the ankle joint or to absorb mechanical energy as needed. The controller and a sensing mechanisms control both the actuator motor and the controllable damper at different times during the walking cycle for level walking, stair ascent and stair descent.

The above noted U.S. patent application Ser. No. 11/600, 291 describes an exoskeleton worn by a human user consisting of a rigid pelvic harness worn about the waist of the user and exoskeleton leg structures each of which extends downwardly alongside one of the human user's legs. The leg structures include hip, knee and ankle joints connected by adjustable length thigh and shin members. The hip joint that attaches the thigh structure to the pelvic harness includes a passive spring or an active actuator to assist in lifting the exoskeleton and said human user with respect to the ground surface upon which the user is walking and to propel the exoskeleton and human user forward. A controllable damper operatively arresting the movement of the knee joint at controllable times during the walking cycle, and spring located at the ankle and foot member stores and releases energy during walking.

The additional references listed below identify materials which are referred to in the description that follows. When cited, each reference is identified by a single number in brackets; for example, the first reference below is cited using the notation "{1}."

1. Palmer, Michael. Sagittal Plane Characterization of Normal Human Ankle Function across a Range of Walking Gait Speeds. Massachusetts Institute of Technology Master's Thesis, 2002.
2. Gates Deanna H., Characterizing ankle function during stair ascent, descent, and level walking for ankle prosthesis and orthosis design. Master thesis, Boston University, 2004.
3. Hansen, A., Childress, D. Miff, S. Gard, S. and Mesplay, K., The human ankle during walking: implication for the design of biomimetic ankle prosthesis, Journal of Biomechanics, 2004 (In Press).
4. Koganezawa, K. and Kato, I., Control aspects of artificial leg, IF AC Control Aspects of Biomedical Engineering, 1987, pp. 71-85.
5. Herr H, Wilkenfeld A. User-Adaptive Control of a Magnetorheological Prosthetic Knee. Industrial Robot: An International Journal 2003; 30: 42-55.
6. Seymour Ron, Prosthetics and Orthotics: Lower limb and Spinal, Lippincott Williams & Wilkins, 2002.
7. G. A. Pratt and M. M. Williamson, "Series Elastic Actuators," presented at 1995 IEEE/RSJ International Conference on Intelligent Robots and Systems, Pittsburgh, Pa., 1995.
8. Inman V T, Ralston H J, Todd F. Human walking. Baltimore: Williams and Wilkins; 1981.
9. Hof. A. L. Geelen B. A., and Berg, J. W. Van den, "Calf muscle moment, work and efficiency in level walking; role of series elasticity," Journal of Biomechanics, Vol 16, No. 7, pp. 523-537, 1983.
10. Gregoire, L., and et al, Role of mono- and bi-articular muscles in explosive movements, International Journal of Sports Medicine 5, 614-630.
11. Endo, K., Paluska D., Herr, H. A quasi-passive model of human leg function in level-ground walking. IEEE/RSJ International Conference on Intelligent Robots and Systems OROS); Oct. 9-16, 2006; Beijing, China.

As noted in references {1}, {2}, {3}, and {4} above, an artificial limb system that mimics a biological limb ideally needs to fulfill a diverse set of requirements. The artificial system must be a reasonable weight and have a natural morphological shape, but still have an operational time between refueling or battery recharges of at least one full day. The system must also be capable of varying its position, stiffness, damping and non-conservative motive power in a comparable manner to that of a normal, healthy biological limb. Still further, the system must be adaptive, changing its characteristics given such environmental disturbances as walking speed and terrain variation. The current invention describes a novel actuator and limb architecture capable of achieving these many requirements.

From recent biomechanical studies described in references {1}, {2} and {3} above, researchers have determined that biological joints have a number of features. Among these are:

(a) the ability to vary stiffness and damping;
(b) the ability to generate large amounts of positive mechanical work (non-conservative motive output); and
(c) the ability to produce large amounts of power and torque when needed.

An example of the use of more than one control strategy in a single biological joint is the ankle. See {1} and {2}. For level ground ambulation, the ankle behaves as a variable stiffness device during the early to midstance period, storing and releasing impact energies. Throughout terminal stance, the ankle acts as a torque source to power the body forward. In distinction, the ankle varies damping rather than stiffness during the early stance period of stair descent. These biomechanical findings suggest that in order to mimic the actual behavior of a human joint or joints, stiffness, damping, and non-conservative motive power must be actively controlled in the context of an efficient, high cycle-life, quiet and cosmetic biomimetic limb system, be it for a prosthetic or orthotic device. This is also the case for a biomimetic robot limb since it will need to satisfy the same mechanical and physical laws as its biological counterpart, and will benefit from the same techniques for power and weight savings.

The current state of the art in prosthetic leg systems include a knee joint that can vary its damping via magnetorheological fluid as described in {5}, and a carbon fiber ankle which has no active control, but that can store energy in a spring structure for return at a later point in the gait cycle e.g. the Flex-Foot {4} or the Seattle-Lite {6}. None of these systems are able to add energy during the stride to help keep the body moving forward or to reduce impact losses at heel strike. In the case of legged robotic systems, the use of the Series Elastic Actuator (SEA) enables robotic joints to control their position and torque, such that energy may be added to the system as needed. See {7}. In addition, the SEA can emulate a physical spring or damper by applying torques based on the position or velocity of the joint. However, for most applications, the SEA requires a tremendous amount of electric power for its operation, resulting in a limited operational life or an overly large power supply. Robotic joint designs in general use purely active components and often do not conserve electrical power through the use of variable stiffness and variable-damping devices.

SUMMARY OF THE INVENTION

For an artificial joint to behave like a biological joint, a synthetic actuator must have the following properties:

1) The actuator must consume negligible power when exerting zero force. Near the equilibrium length of muscle (peak of active tension-length curve), the passive tension is typically zero. Thus, a muscle-actuated joint goes limp when the muscles are not electrically stimulated.

2) The actuator must consume negligible power when outputting force at constant length (isometric) and while performing dissipative, non-conservative work. Muscle tissue is very efficient for isometric and dissipative control modes.

3) The actuator must be capable of independently engaging flexion and extension tendon-like, series springs. Since biological joints have at least one flexor muscle and at least one extensor muscle, the time at which a flexor tendon becomes taught or engaged can be independent of the time at which an extensor tendon becomes engaged. As an example, with a muscle-actuated joint, the elastic energy from one tendon can be released as a second tendon is being elongated.

4) The actuator must be capable of independently varying joint position and stiffness. Through co-contraction between a muscle flexor and extensor, joint stiffness can be modulated without changing joint position. Further, joint position can be varied while keeping joint stiffness constant.

5) The actuator must be capable of exploiting series elasticity for mechanical power amplification, or a "catapult" control modality. For motion tasks that require high mechanical power, muscle-tendon units in animals and humans often employ a catapult control where the muscle belly stretches the series tendon, and later that stored elastic energy is released to achieve relatively higher joint powers than would be possible if the muscle belly were to generate that power directly.

In one aspect, the present invention is a controller and a control methodology for a biomimetic robotic leg based on a neuromuscular model of human locomotion. The control architecture commands biomimetic torques at the ankle, knee, and hip joints of a powered leg prosthesis, orthosis, or exoskeleton during walking. In a preferred embodiment, the powered device includes artificial ankle and knee joints that are torque controllable. Appropriate joint torques are provided to the user as determined by the feedback information provided by sensors mounted at each joint of the robotic leg device. These sensors include, but are not limited to, angular joint displacement and velocity using digital encoders, hall-effect sensors or the like, torque sensors at the ankle and knee joints, and at least one inertial measurement unit (IMU) located between the knee and the ankle joints.

Sensory information of joint state (position and velocity) from the robotic leg is used as inputs to a neuromuscular model of human locomotion. Joint state sensory information from the robotic leg is used to determine the internal state for each of its virtual muscles, and what the individual virtual muscle force and stiffness should be given particular levels of muscle activation is determined from a spinal reflex model. If the robotic leg is a leg prosthesis worn by a transfemoral amputee, angular sensors at the ankle and knee measure joint state for these joints. For the hip joint, the absolute orientation of the user's thigh is determined using both the angular joint sensor at the prosthetic knee and an IMU positioned between the prosthetic knee and the ankle joints. To estimate hip position and velocity, the control architecture works under the assumption that the upper body (torso) maintains a relative vertical position during gait.

In one aspect, the invention is a model-based neuromechanical controller for a robotic limb comprising at least one joint, the controller comprising a neuromuscular model including a muscle model, muscle tendon lever arm and muscle tendon length equations and reflect control equations, the neuromuscular model being configured to receive feedback data relating to a measured state of the robotic limb and, using the feedback data, and the muscle model, muscle tendon lever arm and muscle tendon length equations and reflect control equations of the neuromuscular model, to determine at least one torque command, the controller further comprising a torque control system in communication with the neuromuscular model, whereby the torque control system receives the at least one torque command from the neuromuscular model for controlling the robotic limb joint. In a preferred embodiment, the feedback data is provided by at least one sensor mounted at each joint of the robotic limb. In another preferred embodiment, the robotic limb is a leg and the controller further includes a finite state machine synchronized to the leg gait cycle, the finite state machine being configured to receive the feedback data from the at least one sensor to determine a gait phase of the robotic leg using the feedback data received.

In another aspect, the invention is a model-based method for controlling a robotic limb comprising at least one joint, comprising the steps of receiving feedback data relating to the state of the robotic limb at a finite state machine, determining the state of the robotic limb using the finite state machine and the received feedback data, determining, using a neuromuscular model that includes muscle tendon lever arm and muscle tendon length equations and reflex control equations, and state information from the finite state machine, at least one desired joint torque or stiffness command to be sent to the robotic limb and commanding the biomimetic torques and stiffnesses determined by the muscle model processor at the robotic limb joint.

BRIEF DESCRIPTION OF THE DRAWINGS

Other aspects, advantages and novel features of the invention will become more apparent from the following detailed description of the invention when considered in conjunction with the accompanying drawings wherein:

FIGS. 2A-F depict six stages in the evolution of a general neuromuscular model architecture, according to one aspect of the present invention;

FIGS. 6A-D depict adaptation to walking up stairs, including snapshots of the model (FIG. 6A), net work (FIG. 6B), extensor muscle activation patterns (FIG. 6C), and the corresponding ground reaction force (FIG. 6D), according to one aspect of the present invention;

FIGS. 7A-D depict adaptation to walking down stairs, including snapshots of the model (FIG. 7A), net work (FIG. 7B), extensor muscle activation patterns (FIG. 7C), and the corresponding ground reaction force (FIG. 7D), according to one aspect of the present invention;

FIGS. 9A-C depict a contact model, according to one aspect of the present invention;

FIGS. 29B and 29C are graphs comparing the behaviors of biological ankle and knee joints respectively with the modeled joints of FIG. 29A;

FIG. 31A shows the major components of the transtibial system are shown;

FIG. 31B shows the monoarticular ankle mechanism of FIG. 31A in more detail;

DETAILED DESCRIPTION

Figure 1:
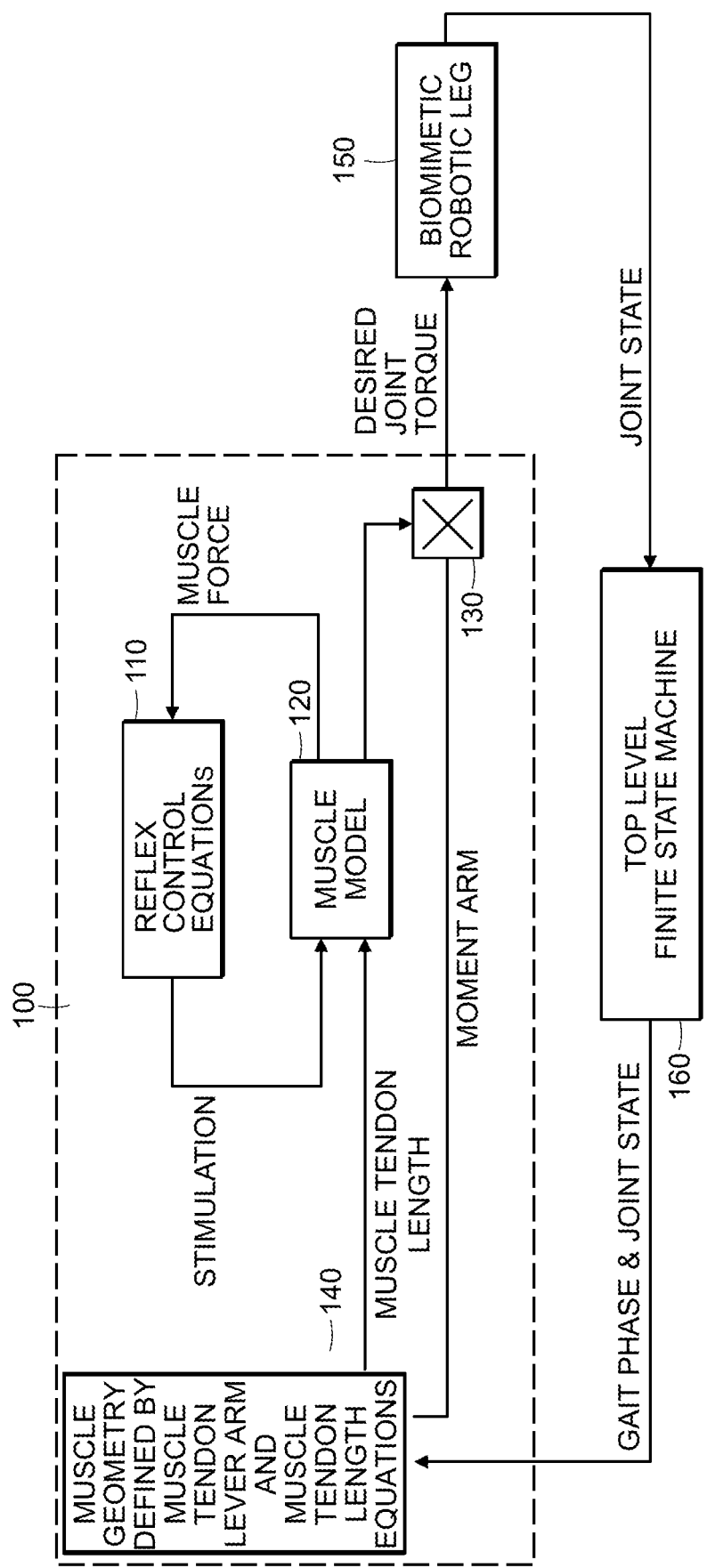
FIG. 1 is a block diagram of an exemplary embodiment of a general neuromuscular model architecture, according to one aspect of the present invention.

A control architecture is presented to command biomimetic torques at the ankle, knee, and hip joints of a powered leg prosthesis, orthosis, or exoskeleton during walking. In this embodiment, the powered device includes artificial ankle and knee joints that are torque controllable. Appropriate joint torques are provided to the user as determined by the feedback information provided by sensors mounted at each joint of the robotic leg device. These sensors include, but are not limited to, angular joint displacement and velocity using digital encoders, hall-effect sensors or the like, torque sensors at the ankle and knee joints and at least one inertial measurement unit (IMU) located between the knee and the ankle joints.

Sensory information of joint state (position and velocity) from the robotic leg (hip, knee and ankle) is used as inputs to a neuromuscular model of human locomotion. This model uses joint state sensory information from the robotic leg to determine the internal state for each of its virtual muscles, and establishes what the individual virtual muscle force and stiffness should be given particular levels of muscle activation determined from a spinal reflex model. If the robotic leg is a leg prosthesis worn by a transfemoral amputee, angular sensors at the ankle and knee measure joint state for these joints. For the hip joint, the absolute orientation of the user's thigh is determined using both the angular joint sensor at the prosthetic knee and an IMU positioned between the prosthetic knee and the ankle joints. To estimate hip position and velocity, the control architecture works under the assumption that the upper body (torso) maintains a relative vertical position during gait.

As used herein, and in the Appl.s incorporated by reference herein, the following terms expressly include, but are not to be limited to:

"Actuator" means a type of motor, as defined below.

"Agonist" means a contracting element that is resisted or counteracted by another element, the antagonist.

"Agonist-antagonist actuator" means a mechanism comprising (at least) two actuators that operate in opposition to one another: an agonist actuator that, when energized, draws two elements together and an antagonist actuator that, when energized, urges the two elements apart.

"Antagonist" means an expanding element that is resisted or counteracted by another element, the agonist.

"Biomimetic" means a man-made structure or mechanism that mimics the properties and behavior of biological structures or mechanisms, such as joints or limbs.

"Dorsiflexion" means bending the ankle joint so that the end of the foot moves upward.

"Elastic" means capable of resuming an original shape after deformation by stretching or compression.

"Extension" means a bending movement around a joint in a limb that increases the angle between the bones of the limb at the joint.

"Flexion" means a bending movement around a joint in a limb that decreases the angle between the bones of the limb at the joint.

"Motor" means an active element that produces or imparts motion by converting supplied energy into mechanical energy, including electric, pneumatic, or hydraulic motors and actuators.

"Plantarflexion" means bending the ankle joint so that the end of the foot moves downward.

"Spring" means an elastic device, such as a metal coil or leaf structure, which regains its original shape after being compressed or extended.

An exemplary embodiment of a neuromuscular model-based control scheme according to this aspect of the invention is shown as a block diagram in FIG. 1. In FIG. 1, a neuromuscular model 100 according to the invention includes reflex control equations 110 for each modeled muscle unit 120. The predicted forces and stiffnesses from all the modeled muscles are used to compute 130 model estimates of desired joint torques and stiffnesses using muscle moment arm values provided by muscle tendon lever arm and muscle tendon length equations 140, which moment arm and muscle tendon length values from joint state, e.g., joint angle, and data from the literature. A muscle tendon unit (MTU), also referred to a muscle tendon complex (MTC), and associated parameters, are described below with reference to FIGS. 8, 14 and 15. For the purposes of this description, MTU has the same meaning as MTC. The model estimates are then sent to torque control system of biomimetic robotic leg 150 as desired net torque and stiffness values for joints of biomimetic robotic leg 150. Top level finite state machine 160 then tracks the torque and stiffness values at each robotic joint of biomimetic robotic leg 150. Finite state machine 160 receives joint state as an input and provides gait phase and joint state as outputs to neuromuscular model 100.

In order for each of the virtual muscle to produce its required force, a muscle stimulation parameter STIM(t) is required. This parameter can be determined from either an outside input or a local feedback loop. In the control methodology for the exemplary biomimetic leg, the STIM(t) is computed based on local feedback loops. This architecture is based on the reflex feedback framework developed by Geyer and Herr [H. Geyer, H. Herr, "A muscle-reflex model that encodes principles of legged mechanics predicts human walking dynamics and muscle activities," (Submitted for publication), herein incorporated by reference in its entirety]. In this framework the neural-control is designed to mimic the stretch reflex of an intact human muscle. This neuromuscular reflex-based control methodology allows the biomimetic robotic leg to replicate human-like joint mechanics.

Neuromechanical model. A human model with a reflex control that encodes principles of legged mechanics predicts human walking dynamics and muscle activities. While neuroscientists identify increasingly complex neural networks that control animal and human gait, biomechanists find that locomotion requires little motor control if principles of legged mechanics are heeded. Here it is shown how muscle reflex behavior could be vital to link these two observations. A model of human locomotion was developed that is driven by muscle reflex behaviors that encode principles of legged mechanics. Equipped with this principle-based reflex control, the model stabilizes into the walking gait from its dynamic interplay with the ground, tolerates ground disturbances, and self-adapts to stairs. Moreover, the model shows qualitative agreement with joint angles, joint torques and muscle activations known from experiments, suggesting that human motor output could largely be shaped by muscle reflex behaviors that link principles of legged mechanics into the neural networks responsible for locomotion.

A human walking model with a motor control is based on muscle reflexes, which are designed to include such principles of legged mechanics. These principles derive from simple conceptual models of legged locomotion and include the reliance on compliant leg behavior in stance [Blickhan, R., 1989. The spring-mass model for running and hopping. J. of Biomech. 22, 1217-1227; Ghigliazza, R., Altendorfer, R., Holmes, P., Koditschek, D., 2003. A simply stabilized running model. SIAM J. Applied. Dynamical Systems 2 (2), 187-218; Geyer, H., Seyfarth, A., Blickhan, R., 2006. Compliant leg behaviour explains the basic dynamics of walking and running. Proc. R. Soc. Lond. B 273, 2861-2867], the stabilization of segmented legs based on static joint torque equilibria [Seyfarth, A., Günther, M., Blickhan, R., 2001. Stable operation of an elastic three-segmented leg. Biol. Cybern. 84, 365-382; Günther, M., Keppler, V., Seyfarth, A., Blickhan, R., 2004. Human leg design: optimal axial alignment under constraints. J. Math. Biol. 48, 623-646], the exploitation of ballistic swing-leg mechanics [Mochon, S., McMahon, T., 1980. Ballistic walking. J. Biomech. 13 (1), 49-57], and the enhancement of gait stability using swing-leg retraction [Seyfarth, A., Geyer, H., Günther, M., Blickhan, R., 2002. A movement criterion for running. J. of Biomech. 35, 649-655; Seyfarth, A., Geyer, H., Herr, H. M., 2003. Swing-leg retraction: a simple control model for stable running. J. Exp. Biol. 206, 2547-2555]. Hill-type muscles combined with spinal reflexes are employed. including positive force and length feedback schemes, to effectively encode these mechanical features.

Comparing the model's behavior with kinetic, kinematic, and electromyographic evidence from the literature for human walking, it has been shown that a neuromuscular model with a motor control designed to encode principles of legged mechanics can produce biological walking mechanics and muscle activities. This reflex control allows the model to tolerate sudden changes in ground level and to adapt to stair ascent and descent without parameter interventions.

The structure and control of the human model evolves in six steps from a conceptual point-mass model into a neuromuscular biped with an upper body and two, three-segment legs each actuated by seven muscles and controlled by muscle reflexes. FIGS. 2A-F depict six stages in the evolution of a general neuromuscular model architecture, according to this aspect of the present invention. The first three stages integrate and stabilize compliant leg behavior in stance (FIG. 2A-C). The fourth stage adds an upper body and its balance control (FIG. 2D). The last two stages prepare and ensure the pro- and retraction of the legs during swing (FIGS. 2E and 2F).

In FIGS. 2A-F, described in more detail in the paragraphs that follow, evolving from a stance leg configuration (FIG. 2A), compliant leg behavior as key to walk and run is generated (FIG. 2B) by driving the soleus muscle (SOL) and the lumped vasti group muscles (VAS) with positive force feedbacks F+. To prevent knee overextension the biarticular gastrocnemius muscle (GAS) is added (FIG. 2C) using F+, and the VAS gets inhibited if the knee extends beyond a 170° threshold. To prevent ankle overextension, the tibialis anterior muscle (TA) is added whose pulling of the ankle joint into a flexed position by positive length feedback L+ is suppressed under normal stance conditions by negative force feedback F− from soleus. To allow leg swings, an upper body is added (FIG. 2D). It is driven into a reference lean with respect to the vertical by the hip flexor (HFL) and co-activated hip extensor muscles (GLU, HAM) of the stance leg, where the biarticular HAM prevents knee overextension resulting from hip extensor moments. The landing of the other (leading) leg initiates swing by adding/subtracting a constant stimulation to HFL/GLU, respectively, and by suppressing VAS proportionally to the load borne by the other leg (FIG. 2E). The actual leg swing is facilitated by HFL using L+ until it gets suppressed by L− of HAM (FIG. 2F). HFL's stimulation is biased dependent on the upper body's lean at take-off. Moreover, using F+ for GLU and HAM retracts and straightens the leg toward the end of swing. Finally, the now unsuppressed L+ of TA drives the ankle to a flexed position (FIG. 2G).

Stance leg compliance and stability. The bipedal spring-mass model is used as the starting point for the conceptual basis for human locomotion (FIG. 2A). Although this model consists only of point-mass 205 that progresses on two massless spring legs 210, 215, it reproduces the center of mass dynamics observed in human walking and running, unifying both gaits in one conceptual framework based on compliant leg behavior in stance [Geyer, H., Seyfarth, A., Blickhan, R., 2006. Compliant leg behaviour explains the basic dynamics of walking and running. Proc. R. Soc. Lond. B 273, 2861-2867].

To implement compliant behavior in neuromuscular legs, each spring 210, 215 is replaced with thigh 220, shank 225, and foot 230, and a soleus muscle (SOL) 235 and a vasti muscle group (VAS) 240 are added, both generating their muscle activity through local positive force feedback (F+) during the stance period of gait (FIG. 2B). This force reflex is modeled in the same way as in Geyer, H., Seyfarth, A., Blickhan, R., 2003. Positive force feedback in bouncing gaits? Proc. R. Soc. Lond. B 270, 2173-2183. Under positive force feedback, the stimulation Sm(t) of a muscle m is the sum of a pre-stimulation S0,m, and the muscle's time-delayed ($\Delta t$) and gained (G) force Fm: $S_m(t) = S_{0,m} + G_m F_m(t-\Delta t_m)$.

While compliant leg behavior is essential, it also threatens joint stability in segmented legs [Seyfarth, A., Günther, M., Blickhan, R., 2001. Stable operation of an elastic three-segmented leg. Biol. Cybern. 84, 365-382; Günther, M., Keppler, V., Seyfarth, A., Blickhan, R., 2004. Human leg design: optimal axial alignment under constraints. J. Math. Biol. 48, 623-646]. In segmented legs, the knee and ankle torques, $\tau_k$ and $\tau_a$, obey the static equilibrium $\tau_k/\tau_a = h_k/h_a$, where $h_k$ and $h_a$ are the perpendicular distances from the knee and the ankle to the leg force vector Fleg, respectively. In effect, a large extension torque at one joint forces the other joint closer to Fleg, threatening its overextension for spring-like behaving legs [for details see Seyfarth, A., Günther, M., Blickhan, R., 2001. Stable operation of an elastic three-segmented leg. Biol. Cybern. 84, 365-382].

This tendency to overextend at the knee or the ankle is countered by adding the gastrocnemius (GAS) 245 and tibialis anterior (TA) 250 muscles (FIG. 2C). Like SOL and VAS, the biarticular GAS uses local positive force feedback (F+) during the stance period of gait. This muscle reflex not only prevents knee hyperextension resulting from large extension torques at the ankle, but also contributes to generating an overall compliant leg behavior. In contrast, the monoarticular TA uses local positive length feedback (L+) with $S_{TA}(t) = S_{0,TA} + G_{TA}(l_{CE,TA} - l_{off,TA})(t-\Delta_{t,TA})$ where $l_{CE,TA}$ is the TA fiber length and $l_{off,TA}$ is a length offset. Flexing the foot, TA's L+ prevents the ankle from overextending when large knee torques develop. This muscle reflex is not required however if sufficient activity of the ankle extensor muscles preserves the torque equilibrium of knee and ankle. To avoid that TA unnecessarily fights SOL in this situation, the TA stimulation is inhibited with a negative force feedback (F−) from the SOL, resulting in $S_{TA}(t) = S_{0,TA} + G_{TA}(l_{CE,TA} - l_{off,TA})(t-\Delta_{t,TA}) - G_{SOLTA} F_{SOL}(t-\Delta t_{SOL})$. To further protect the knee from hyperextending, the VAS gets inhibited if the knee extends beyond a 170 deg threshold, $S_{VAS}(t) = S_{0,VAS} + G_{VAS} F_{VAS}(t-\Delta t_{VAS}) - k_\varphi \Delta_{\varphi k}(t-\Delta t_k)$, where $k_\varphi$ is a proportional gain, $\Delta\varphi_k=\varphi_k-170$ deg, and $\varphi_k$ is the knee angle. This reflex inhibition is only active if $\Delta\varphi>0$ and the knee is actually extending.

Upper body and its balance. In the next step of evolving from the conceptual spring-mass model into a neuromuscular biped, the point mass representation is discarded and an upper body 255 around which the legs can be swung (FIG. 2D) is introduced. This upper body 255 combines head, arms and trunk (HAT). To balance the HAT 255 during locomotion, to each leg is added a gluteus muscle group (GLU) 260 and a hip flexor muscle group (HFL) 265. The GLU 260 and the HFL 265 are stimulated with a proportional-derivative signal of the HAT's 255 forward lean angle $\theta$ with respect to gravity, $S_{GLU/HFL}\sim\pm[k_p(\theta-\theta_{ref})+k_d d\theta/dt]$, where $k_p$ and $k_d$ are the proportional and derivative gains, and $\theta_{ref}$ is a reference lean angle [for similar approaches compare, for instance, Günther, M., Ruder, H., 2003. Synthesis of two-dimensional human walking: a test of the $\lambda$-model. Biol. Cybern. 89, 89-106]. Also included is the biarticular hamstring muscle group (HAM) 270 with $S_{HAM}\sim S_{GLU}$ to counter knee hyperextension that results from a large hip torque developed by the GLU 260 when pulling back the heavy HAT 255. Since hip torques can only balance the HAT 255 if the legs bear sufficient weight, the stimulations of the GLU 260, HAM 270, and HFL 265 are modulated for each leg proportionally to the amount of body weight it bears. As a result, each leg's hip muscles contribute to the HAT's balance control only during stance.

Swing leg pro- and retraction. The human model's structure is complete, except for a muscle-reflex control that produces swing leg pro- and retraction. It is assumed that a stance leg's functional importance reduces in proportion to the amount of body weight (bw) borne by the contralateral leg, and initiate swing leg protraction already in double support (FIG. 2E). The human model detects which leg enters stance last (contralateral leg), and suppresses F+ of the ipsilateral leg's VAS 240 in proportion to the weight the contralateral leg bears, $S_{VAS}(t)=S_{0,VAS}+G_{VAS}F_{VAS}(t-\Delta t_{VAS})-k_\varphi\Delta\varphi_k(t-\Delta t_k)-k_{bw}|F_{leg}^{contra}|$. The contralateral suppression allows the knee to break its functional spring behavior, and flex while the ankle extends, pushing the leg off the ground and forward. While this catapult mechanism can initiate swing only if the ankle pushes sufficiently, the model further prepares swing leg protraction by increasing the stimulation of the HFL 265, and decreasing that of the GLU 260, by a fixed amount $\Delta S$ in double support.

During actual swing, the main reliance is on a leg's ballistic motion, but it is influenced in two ways (FIG. 2F). On one hand, protraction of the swing leg is facilitated. The HFL 265 is stimulated using positive length feedback (L+) biased by the forward pitch angle $\theta_{ref}$ of the HAT 255 at the stance-to-swing transition, $S_{HFL}(t)=S_{0,HFL}k_{lean}(\theta-\theta_{ref})_{TO}+G_{HFL}(l_{CE,HFL}-l_{off,HFL})(t-\Delta_{t,HFL})$. Using this approach, it is ensured that the swing leg's ballistic motion gains the momentum to bring it forward in time [Mochon, S., McMahon, T., 1980. Ballistic walking. J. Biomech. 13 (1), 49-57].

Furthermore, the swing leg is also prevented from overreaching and its retraction is ensured. If legs reach and maintain a proper orientation during swing, legged systems self-stabilize into a gait cycle [McGeer, T., 1990. Passive dynamic walking. Int. J. Rob. Res. 9 (2), 62-82; Seyfarth, A., Geyer, H., Günther, M., Blickhan, R., 2002. A movement criterion for running. J. of Biomech. 35, 649-655; Ghigliazza, R., Altendorfer, R., Holmes, P., Koditschek, D., 2003. A simply stabilized running model. SIAM J. Applied. Dynamical Systems 2 (2), 187-218; Geyer, H., Seyfarth, A., Blickhan, R., 2006. Compliant leg behaviour explains the basic dynamics of walking and running. Proc. R. Soc. Lond. B 273, 2861-2867]. The tolerance of this mechanical self-stability against disturbances can largely be enhanced if swing legs additionally retract before landing [Seyfarth, A., Geyer, H., 2002. Natural control of spring-like running—optimized self-stabilization. In: Proceedings of the 5th international conference on climbing and walking robots. Professional Engineering Publishing Limited, pp. 81-85; Seyfarth, A., Geyer, H., Herr, H. M., 2003. Swing-leg retraction: a simple control model for stable running. J. Exp. Biol. 206, 2547-2555]. To implement this halt-and-retract strategy, three muscle reflexes are included in the human model. The overreaching of the swing leg that would result from the forward impulse the leg receives when the knee reaches full extension during protraction is prevented. Hereto, the HFL's L+ is inhibited proportional to the stretch which the HAM receives in swing, $S_{HFL}(t)=k_{lean}(\theta-\theta_{ref})TO+G_{HFL}(l_{CE,HFL}-l_{off,HFL})(t-\Delta_{t,HFL})-G_{HAMHFL}(l_{CE,HAM}-l_{off,HAM})(t-\Delta_{t,HAM})$. In addition, F+ is used for the GLU, $S_{GLU}(t)=S_{0,GLU}-G_{GLU}+F_{GLU}(t-\Delta t_{GLU})$, and for the HAM, $S_{HAM}(t)=S_{0,HAM}+G_{HAM}F_{HAM}(t-\Delta t_{HAM})$, to ensure that, dependent on the actual protraction momentum, the swing leg not only halts, but also transfers part of this momentum into leg straightening and retraction. Finally, the TA L+ introduced to ensure foot clearance is kept throughout the swing. The SOL, GAS, and VAS remain silent during this phase.

Reflex control parameters. The different reflex contributions to the muscle stimulations Sm(t) are governed through the equations used in the model. No parameter optimization was performed. Parameters were derived from previous knowledge of reflex behavior (F+, L+) or by making plausible estimates. All muscle stimulations are limited in range from 0.01 to 1 before being translated into muscle activations $\Delta_m(t)$. Table 1 presents the stance reflex equations used in the preferred embodiment.

TABLE 1

$S_{SOL}(t) = S_{0,SOL} + G_{SOL} F_{SOL}(t_1)$
$\quad = 0.01 + 1.2/F_{max,SOL} F_{SOL}(t_1)$ $S_{TA}(t) = S_{0,TA} + G_{TA}[l_{CE,TA}(t_1) - l_{off,TA})] - G_{SOL,TA} F_{SOL}(t_1)$
$\quad = 0.01 + 1.1[l_{CE,TA}(t_1) - 0.71 \, l_{opt,TA})] - 0.3/F_{max,SOL}F_{SOL}(t_1)$ $S_{GAS}(t) = S_{0,GAS} + G_{GAS} F_{GAS}(t_1)$
$\quad = 0.01 + 1.1/F_{max,GAS} F_{GAS}(t_1)$ $S_{VAS}(t) = S_{0,VAS} + G_{VAS} F_{VAS}(t_m) - k_\varphi[\varphi_k(t_m) - \varphi_{k,off}][\varphi_k(t_m) > \varphi_{k,off}]$
$\quad [d\varphi_k/dt(t_m) > 0] - k_{bw}|F_{leg}^{contra}(t_s)|^*DSup$
$\quad = 0.09 + 1.15/F_{max,VAS}F_{VAS}(t_m) - 1.15[\varphi(t_m) - 2.97][\varphi(t_m) > 2.97]$
$\quad [d\varphi_k/dt(t_m) > 0] - 0.00167 |F_{leg}^{contra}(t_s)|^*DSup$ $S_{HAM}(t) = S_{0,HAM} + \{k_p[\theta(t_s) - \theta_{ref}] + k_d \, d\theta/dt(t_s)\} + k_{bw}|F_{leg}^{ipsi}(t_s)|$
$\quad = 0.05 + \{1.9[\theta(t_s) - 0.105] + 0.25 \, d\theta/dt(t_s)\} +$
$\quad 0.00167 |F_{leg}^{ipsi}(t_s)|$ $S_{GLU}(t) = S_{0,GLU} + \{k_p[\theta(t_s) - \theta_{ref}] + k_d \, d\theta/dt(t_s)\} + k_{bw}|F_{leg}^{ipsi}(t_s)| - \Delta S^*DSup$
$\quad = 0.05 + \{1.3[\theta(t_s) - 0.105] + 0.25 \, d\theta/dt(t_s)\} +$
$\quad 0.00167 |F_{leg}^{ipsi}(t_s)| - 0.25^*Dsup$ $S_{HFL}(t) = S_{0,HFL} + \{k_p[\theta(t_s) - \theta_{ref}] + k_d \, d\theta/dt(t_s)\} - k_{bw}|F_{leg}^{ipsi}(t_s)| + \Delta S^*DSup$
$\quad = 0.05 + \{1.9[\theta(t_s) - 0.105] + 0.25 \, d\theta/dt(t_s)\} -$
$\quad 0.00167 |F_{leg}^{ipsi}(t_s)| + 0.25^*DSup$ ($t_1 = t - 20$ ms, $t_m = t - 10$ ms, and $t_s = t - 5$ ms, DSup is 1 if leg is trailing leg in double support, otherwise 0, {}+/− refers to only positive/negative values)

Table 2 presents the swing reflex equations used in the preferred embodiment.

TABLE 2

$S_{SOL}(t) = S_{0,SOL}$
$= 0.01$ $S_{TA}(t) = S_{0,TA} + G_{TA}[\ell_{CE,TA}(t_1) - \ell_{off,TA}]$
$= 0.01 + 1.1[\ell_{CE,TA}(t_1) - 0.71 \ell_{opt,TA}]$ $S_{GAS}(t) = S_{0,GAS}$
$= 0.01$ $S_{VAS}(t) = S_{0,VAS}$
$= 0.01$ $S_{HAM}(t) = S_{0,HAM} + G_{HAM}F_{HAM}(t_s)$
$= 0.01 + 0.65/F_{max,HAM}F_{HAM}(t_s)$ $S_{GLU}(t) = S_{0,GLU} + G_{GLU}F_{GLU}(t_s)$
$= 0.01 + 0.4/F_{max,GLU}F_{GLU}(t_s)$ $S_{HFL}(t) = S_{0,HFL} + GH_{FL}[\ell_{CE,HFL}(t_s) - \ell_{off,HFL}] -$
$\quad G_{HAM,HFL}[\ell_{CE,HAM}(t_s) - \ell_{off,HAM}] + \{k_{lean}[\theta(t_s) - \theta_{ref}]\}PTO$
$= 0.01 + 0.35[\ell_{CE,HFL}(t_s) - 0.6 \ell_{opt,HFL}] -$
$\quad 4[\ell_{CE,HAM}(t_s) - 0.85 \ell_{opt,HAM}] + \{1.15[\theta(t_s) - 0.105]\}PTO$ ({}PTO: constant value taken at previous take off.)

Figure 3:
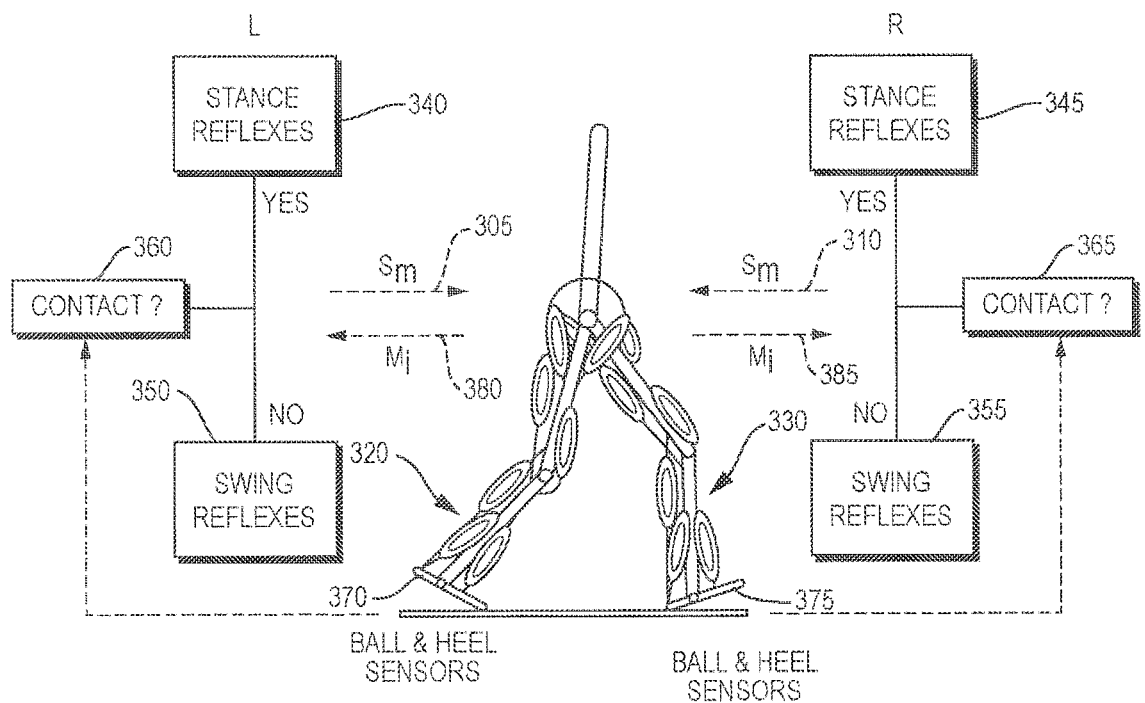
FIG. 3 graphically depicts pattern generation, according to one aspect of a general neuromuscular model architecture according to the present invention.

Results. Although the human model has no central pattern generator (CPG) that feed-forwardly activates its muscles, it switches for each leg between the different reflexes for stance and swing using sensors located at the ball and heel of each foot to detect ground. As a result, the model's dynamic interaction with its mechanical environment becomes a vital part of generating muscle activities. FIG. 3 graphically depicts pattern generation according to this aspect of the invention. In FIG. 3, instead of a central pattern, reflexes generate the muscle stimulations, $S_m$ 305, 310. Left (L) 320 and right (R) 330 leg have separate stance 340, 345 and swing 350, 355 reflexes, which are selected based on contact sensing 360, 365 from ball and heel sensors 370, 375. The reflex outputs depend on mechanical inputs, $M_i$ 380, 385, intertwining mechanics and motor control.

Figure 4A:
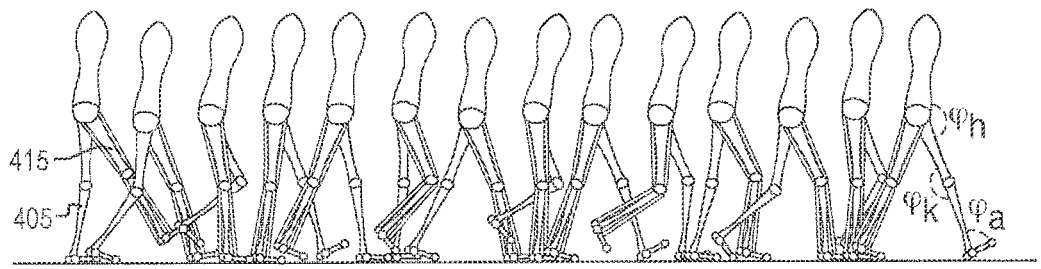
FIGS. 4A and 4B depict walking of a human model self-organized from dynamic interplay between model and ground, and the corresponding ground reaction force, respectively, according to one aspect of the present invention.
Figure 4B:
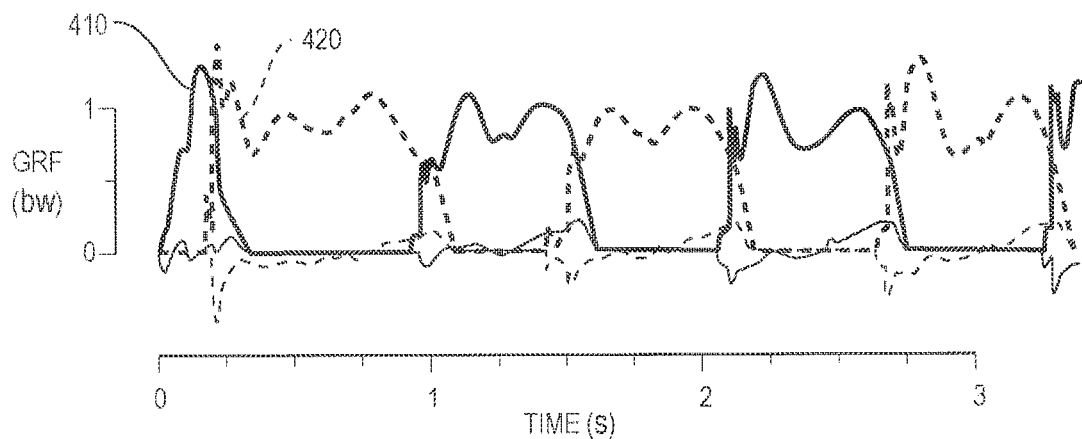

Walking gait. To study how important this interdependence of mechanics and motor control can be to human locomotion, the model was started with its left leg in stance and its right leg in swing at a normal walking speed v0=1.3 ms-1. Since the modeled muscle reflexes include time delays of up to 20 ms, all muscles are silent at first. FIGS. 4A and 4B depict walking of a human model self-organized from dynamic interplay between model and ground and the corresponding ground reaction force, respectively, according to one aspect of the present invention. In FIGS. 4A and 4B, snapshots of human model taken every 250 ms (FIG. 4A) and corresponding model GRF (FIG. 4B) are shown, with separate plots for left 405, 410 and right 415, 420 legs (30 Hz low-pass filtered). Starting with a horizontal speed of 1.3 ms$^{-1}$, the model slows down in the first two steps, but then rapidly recovers into walking at the same speed. Leg muscles are shown only for the right leg 415, indicating muscle activation >10%. Initial conditions for $\varphi_{a,k,h}$ (definition of ankle, knee and hip angle) for each leg were: $\varphi_{a,k,h}$=85 deg, 175 deg, 175 deg (left leg) and $\varphi_{a,k,h}$=90 deg, 175 deg, 140 deg (right leg).

Because of these disturbed initial conditions, the model slightly collapses and slows down in its first step (FIG. 4A). If its parameters are chosen properly, however, the model rapidly recovers in the following steps, and walking self-organizes from the dynamic interplay between model and ground. Here the vertical ground reaction force (GRF) of the legs in stance shows the M-shape pattern characteristic for walking gaits (FIG. 4B), indicating similar whole-body dynamics of model and humans for steady state walking.

Figure 5A:
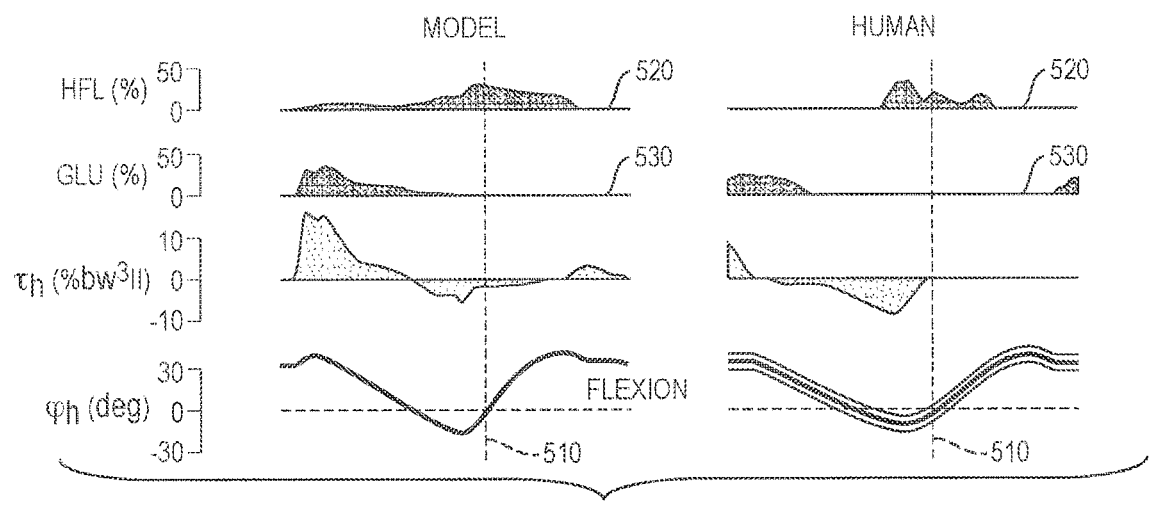
FIGS. 5A-C compare steady state walking for the model and a human subject for hip, knee, and ankle, respectively, according to one aspect of the present invention.
Figure 5B:
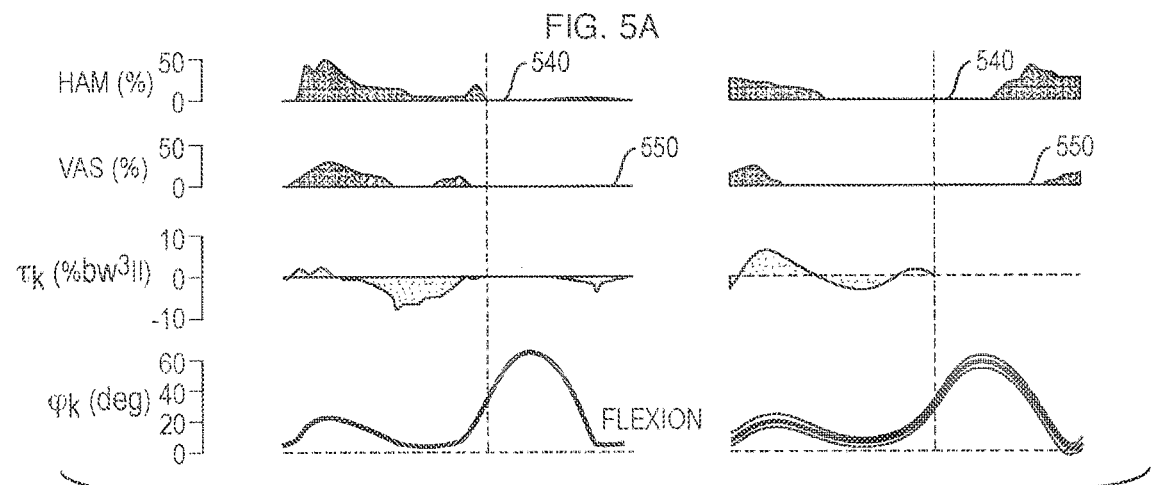
Figure 5C:
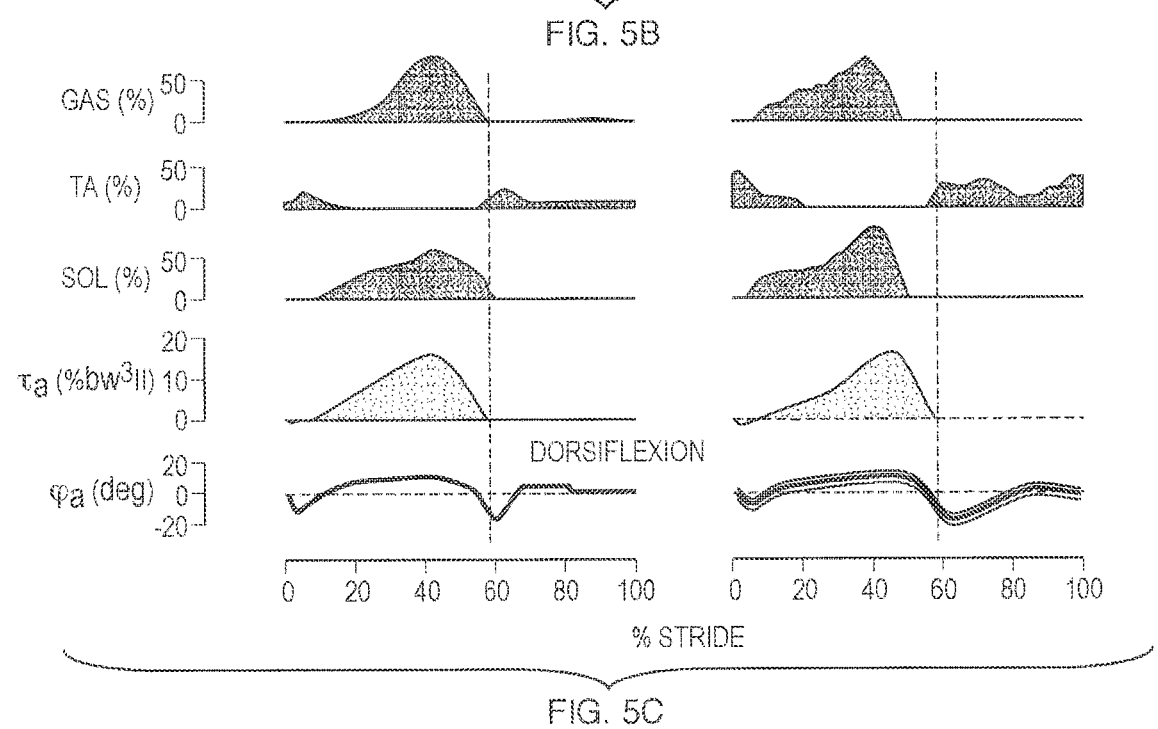

Steady-state patterns of angles, torques and muscle activations. This similarity also holds upon closer inspection; the model shows qualitative agreement with angle, torque and muscle activation patterns known from human walking data. FIGS. 5A-C compare steady state walking at 1.3 ms$^{-1}$ for the model and a human subject for hip (FIG. 5A), knee (FIG. 5B), and ankle (FIG. 5C), respectively, according to one aspect of the present invention. In FIGS. 5A-C, normalized to one stride from heel-strike to heel-strike of the same leg, the model's steady-state patterns of muscle activations, torques, and angles of hip, knee and ankle are compared to human walking data (adapted from Perry, 1992). Vertical dotted lines 510 around 60% of stride indicate toe off. Compared muscles are adductor longus (HFL) 520, upper gluteus maximum (GLU) 530, semimembranosis (HAM) 540, and vastus lateralis (VAS) 550.

The strongest agreement between model prediction and walking data can be found at the ankle (FIG. 5C). The reflex model not only generates ankle kinematics $\varphi_a$ and torques $\tau_a$ observed for the human ankle in walking, but also predicts SOL, TA and GAS activities that resemble the experimental SOL, TA and GAS activities as inferred from their surface electromyographs. For SOL and GAS, this activity is generated exclusively by their local F+ reflexes in stance. For TA, its L+ reflex responds with higher activity to plantar flexion of the foot in early stance, but gets suppressed by F− from SOL during the remainder of that phase. Only when SOL activity reduces at the transition from stance to swing (60% of stride), does the TA's L+ resume, pulling the foot against plantar flexion.

The comparison shows a weaker agreement for the knee and the hip. For instance, although the general trajectory $\varphi_k$ of the human knee is captured by the model, its knee flexes about 10 degree or 30% more than the human's in early stance (FIG. 5B). Related to this larger knee flexion, the model lacks the observed VAS activity in late swing that continues into early stance. Only after heel-strike, the F+ of VAS engages and can activate the muscle group in response to the loading of the leg. The delay in extensor activities causes not only a relatively weak knee in early stance, but also the heavy HAT to tilt forward after impact. Since the balance control of the HAT engages gradually with the weight borne by the stance leg, the balance reflexes are silent until heel-strike and then must produce unnaturally large GLU and HAM activities to return the HAT to its reference lean (FIG. 5C). Hence, the model's hip trajectory $\varphi_h$ and torque pattern $\tau_h$ least resemble that of humans whose hip extensors GLU and HAM are active before impact and can prevent such an exaggerated tilt of the trunk.

Self-adaptation to ground changes. Despite its limited reflex control, the human model tolerates sudden, and self-adapts to permanent, changes of the ground level. FIGS. 6A-D show an example in which the model encounters a sequence of stairs going up 4 cm each. FIGS. 6A-D depict adaptation to walking up stairs, including snapshots of the model (FIG. 6A), net work (FIG. 6B), extensor muscle activation patterns (FIG. 6C), and the corresponding ground reaction force (FIG. 6D), according to one aspect of the present invention. In FIGS. 6A-D, approaching from steady-state walking at 1.3 ms$^{-1}$, eight strides of the human model are shown covering five steps of 4 cm incline each. The model returns to steady-state walking on the 8th stride. One stride is defined from heel-strike to heel-strike of the right leg. Shown in FIG. 6A are snapshots of the model at heel-strike and toe-off of the right leg. For this leg are further shown, in FIG. 6B, the net work during stance generated at hip, knee and ankle with positive work being extension work; in FIG. 6C, the activation patterns of the five extensor muscles of each stride; and, in FIG. 6D, the corresponding ground reaction forces 650 normalized to body weight (bw), with ground reaction forces of the left leg 660 are included for comparison.

Approaching from steady-state walking (1st stride), the model hits the stairs at the end of the 2nd stride with the foot of its outstretched right leg (FIG. 6A). This early impact slows down the model and tilts the upper body forward, which is countered by a large hip torque generated by the GLU and HAM (3rd stride, FIGS. 6B and 6C). Since hip extension torques tend to also extend the knee, the VAS does not feel as much force as in steady-state and its force feedback control lowers its muscle stimulation (FIG. 6C), even though the net work at the knee during stance remains about the same as in steady state. In contrast, the slow down of the model reduces the force the ankle extensors GAS and SOL feel during stance, and their force feedback reflexes produce slightly less muscle stimulation, lowering the net work of the ankle (FIGS. 6B and 6C). In strides 4 and 5 the model settles into upstair walking at about 1 ms$^{-1}$ where the forward and upward thrust is generated mainly at the hip and knee. After reaching the plateau in the 6th stride, the model recovers into its original steady-state walking speed of 1.3 ms$^{-1}$ in the 8th stride.

FIGS. 7A-D depict adaptation to walking down stairs, including snapshots of the model (FIG. 7A), net work (FIG. 7B), extensor muscle activation patterns (FIG. 7C), and the corresponding ground reaction force (FIG. 7D), according to one aspect of the present invention. In FIGS. 7A-D, approaching from steady-state walking at 1.3 ms$^{-1}$, eight strides of the human model are shown covering five steps of 4 cm incline each. The model returns to steady-state walking on the 8th stride. One stride is defined from heel-strike to heel-strike of the right leg. Shown in FIG. 7A are snapshots of the model at heel-strike and toe-off of the right leg. For this leg are further shown, in FIG. 7B, the net work during stance generated at hip, knee and ankle with positive work being extension work; in FIG. 7C, the activation patterns of the five extensor muscles of each stride; and, in FIG. 7D, the corresponding ground reaction forces 750 normalized to body weight (bw), with ground reaction forces of the left leg 760 are included for comparison. The model returns to steady state walking at 1.3 ms$^{-1}$ in the 14th stride after covering five steps down with 4 cm decline each.

FIGS. 7A-D continues the walking sequence with the model encountering stairs going down. At the end of the 9th stride, the model hits the first step down with its right foot (FIG. 7A). The downward motion accelerates the model and results in an overall larger first impact of the right leg in the 10th stride with a stronger response of most extensor muscles (FIGS. 7C and 7D). Only the GAS generates less force, because the knee stays more flexed than usual in this stride. As a result, positive net work at the ankle increases substantially (FIG. 7B). This increase and a larger HFL stimulation (not shown) caused by the forward lean of the upper body at its take-off (FIG. 7A) propel the right leg forward in swing increasing the step length (FIG. 7A). After the transitional 10th stride, the model keeps the larger step length in the downward motion (strides 11 and 12), where the model's downward acceleration is countered by increased activity of the GLU, HAM and VAS immediately following impact (FIGS. 7C and 7D), which reduces net positive work at the hip and increases net negative work at the knee (FIG. 7B), and stabilizes the model into walking down at about 1.5 ms$^{-1}$. Back on level ground, the lack of downward acceleration slows down the model, which automatically reduces its step length (FIG. 7A) and drives it back into steady-state walking at 1.3 ms$^{-1}$ within the 13th and 14th step.

For both walking up and down stairs, no single control is responsible. The key to the model's tolerance and adaptation are its dynamic muscle-reflex responses. The rebound of the stance leg depends on how much load the leg extensors SOL, GAS and VAS feel, which guarantees that the leg yields sufficiently to allow forward progression when going up, but brakes substantially when going down. On the other hand, the forward propulsion of the swing leg varies with the model dynamics. Sudden deceleration after impact of the opposite leg, forward lean of the upper body, and ankle extension rate near the end of stance—all contribute to leg propulsion in swing. These combined features ensure that the swing leg protracts enough in upstair walking and substantially in downstair walking. For the latter, the force feedbacks of GLU and HAM constrain excess rotations of the leg and instead force it to rapidly retract and straighten.

Figure 8:
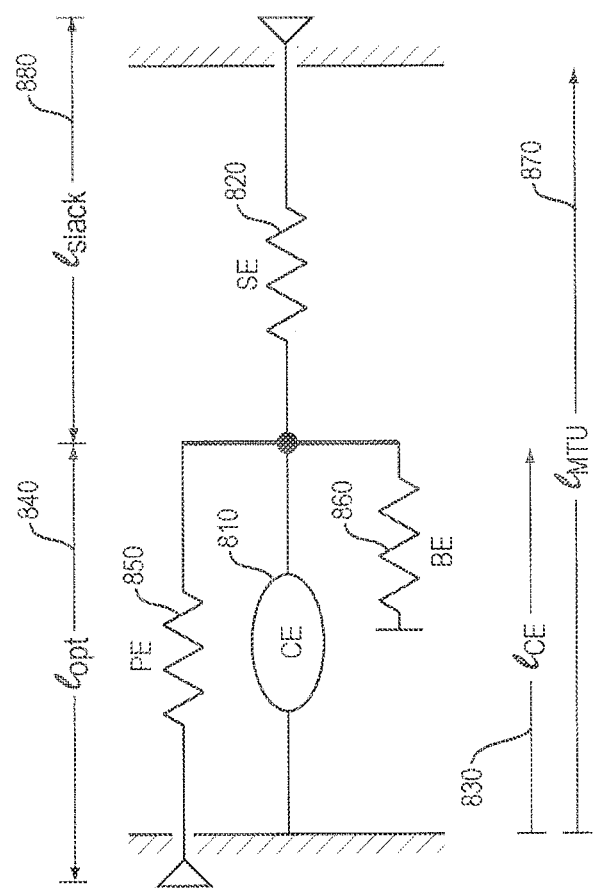
FIG. 8 is a schematic of a muscle-tendon model, according to one aspect of the present invention.

Muscle tendon units. All 14 muscle-tendon units (MTUs) of the biped have the same model structure. FIG. 8 is a schematic of a muscle-tendon model, according to one aspect of the present invention. In FIG. 8, active, contractile element (CE) 810 together with series elasticity (SE) 820 form the muscle-tendon unit (MTU) in normal operation. If CE 810 stretches beyond its optimum length $l_{CE}$ 830 ($l_{CE} > l_{opt}$ 840), parallel elasticity (PE) 850 engages. Conversely, buffer elasticity (BE) 860 prevents the active CE 810 from collapsing if SE 820 is slack ($l_{MTU}$ 870–$l_{CE}$ 830<$l_{slack}$ 880).

As seen in FIG. 8, an active, Hill-type contractile element (CE) produces force in line with a series elasticity (SE). Although the MTUs are fitted into the skeleton such that the individual CEs operate mainly on the ascending limb of their force-length relationship, the MTU model includes a parallel elasticity (PE), which engages if the CE stretches beyond its optimum length $l_{opt}$. In addition, a buffer elasticity (BE) ensures that the CE cannot collapse when the geometry of the leg shortens the MTU so much that it becomes slack. Note that BE is merely a numerical tool that allows the MTU to describe a slack muscle, for instance, a slack GAS when the knee overly flexes. BE does however not result in forces outside the MTU.

Table 3 presents individual MTU parameters. All parameters are estimated from Yamaguchi et al. [Yamaguchi, G. T., Sawa, A. G.-U., Moran, D. W., Fessler, M. J., Winters, J. M., 1990. A survey of human musculotendon actuator parameters. In: Winters, J., Woo, S.-Y. (Eds.), Multiple Muscle Systems: Biomechanics and Movement Organization. Springer-Verlag, New York, pp. 717-778]. The maximum isometric forces $F_{max}$ are estimated from individual or grouped muscle-physiological cross-sectional areas assuming a force of 25N per cm$^{-2}$. The maximum contraction speeds $v_{max}$ are set to $6l_{opt}$ s$^{-1}$ for slow muscles and to $12l_{opt}$ s$^{-1}$ for medium fast muscles. The optimum CE lengths $l_{opt}$ and the SE slack lengths $l_{slack}$ reflect muscle fiber and tendon lengths.

TABLE 3

|  | SOL | TA | GAS | VAS | HAM | GLU | HFL |
|---|---|---|---|---|---|---|---|
| $F_{max}$ (N) | 4000 | 800 | 1500 | 6000 | 3000 | 1500 | 2000 |
| $v_{max}$ ($l_{opt}$ s$^{-1}$) | 6 | 12 | 12 | 12 | 12 | 12 | 12 |
| $l_{opt}$ (cm) | 4 | 6 | 5 | 8 | 10 | 11 | 11 |
| $l_{slack}$ (cm) | 26 | 24 | 40 | 23 | 31 | 13 | 10 |

Details on how CE and SE were modeled can be found in Geyer et al. [Geyer, H., Seyfarth, A., Blickhan, R., 2003. Positive force feedback in bouncing gaits? Proc. R. Soc. Lond. B 270, 2173-2183]. The force of the CE, $F_{CE}$=A $F_{max}$ $f_l$ ($l_{CE}$)$f_v$ ($v_{CE}$), is a product of muscle activation A, CE force-length relationship $f_l$ ($l_{CE}$), and CE force-velocity relationship $f_v$ ($v_{CE}$). Based on this product approach, the MTU dynamics are computed by integrating the CE velocity $v_{CE}$, which is found by inverting $f_v$ ($v_{CE}$). Given that $F_{SE}=F_{CE}+FP_E-F_{BE}$, $f_v$ ($v_{CE}$)=($F_{SE}-F_{PE}+F_{BE}$)/(A $F_{max}$ $f_l$($l_{CE}$)). This equation has a numerically critical point during muscle stretch when $F_{SE}$ $F_{PE}$ approaches zero. To speed up simulations, this critical point is avoided by introducing $f_v$ ($v_{CE}$) into the force production of the parallel elasticity $F_{PE}\sim(l_{CE}-l_{opt})^2$ $f_v$ ($v_{CE}$). Note that PE engages outside the normal range of operation in the model, and like BE, plays a minor role for the muscle dynamics during normal locomotion. With this approach, however, $f_v$ ($v_{CE}$)=($F_{SE}$+$F_{BE}$)/(A $F_{max}$ $f_l$ ($l_{CE}$)+$F_{PE}$) is obtained, which can numerically be integrated using coarse time steps. While this approach is convenient to speed up the model simulation, it was also critical when muscle dynamics were emulated on PC boards with fixed and limited time resolution.

The MTUs have common and individual parameters. The common parameters include the time constant of the excitation contraction coupling, $t_{ecc}$=0.01; the CE force-length relationship's width, w=0.56$l_{opt}$, and residual force factor, c=0.05; the CE force-velocity relationship's eccentric force enhancement, N=1.5, and shape factor, K=5; and the SE reference strain, $\varepsilon_{ref}$=0.04 [for details, see Geyer, H., Seyfarth, A., Blickhan, R., 2003. Positive force feedback in bouncing gaits? Proc. R. Soc. Lond. B 270, 2173-2183]. Also common) parameters are the PE reference strain $\varepsilon_{PE}$=w where $F_{PE}=F_{max}$ ($l_{CE}/l_{opt}-1)^2/\varepsilon_{PE}^2$ $f_v$ ($v_{CE}$), and the BE rest length $l_{min}=l_{opt}$-w and its reference compression $\varepsilon_{BE}$=w/2 where $F_{BE}=F_{max}$ [($l_{min}-l_{CE})/l_{opt}]^2/\varepsilon_{PE}^2$. The individual MTU attachment parameters are readily available from the literature and distinguish each muscle or muscle group. Their values are listed in Table 4.

TABLE 4

| | MTU attachment parameters | | | | | | | | |
|---|---|---|---|---|---|---|---|---|---|
| | ankle | | | knee | | | hip | | |
| | SOL | TA | GAS | GAS | VAS | HAM | HAM | GLU | HFL |
| $r_0$ (cm) | 5 | 4 | 5 | 5 | 6 | 5 | 8 | 10 | 10 |
| $\varphi_{max}$ (deg) | 110 | 80 | 110 | 140 | 165 | 180 | — | — | — |
| $\varphi_{ref}$ (deg) | 80 | 110 | 80 | 165 | 125 | 180 | 155 | 150 | 180 |
| $\rho$ | 0.5 | 0.7 | 0.7 | 0.7 | 0.7 | 0.7 | 0.7 | 0.5 | 0.5 |

Musculoskeletal connections and mass distribution. The MTUs connect to the skeleton by spanning one or two joints. The transfer from muscle forces $F_m$ to joint torques $\tau_m$ is modeled using variable lever arms $r_m(\varphi)=r_0 \cos(\varphi-\varphi_{max})$ for the ankle and knee where $\varphi$ is the joint angle, $\varphi_{max}$ is the angle at which $r_m$ reaches its maximum, and $\tau_m=r_m(\varphi)F_m$. For the hip, it is simply assumed that $r_m(\varphi)=r_0$. On the other hand, changes $\Delta l_m$ in MTU lengths are modeled as $\Delta l_m=\rho r$ [$\sin(\varphi-\varphi_{max})-\sin(\varphi_{ref}-\varphi_{max})$] for the ankle and knee; and as $\Delta l_m=\rho r(\varphi-\varphi_{ref})$ for the hip. The reference angle $\varphi_{ref}$ is the joint angle where $l_m=l_{opt}+l_{slack}$. The factor $\rho$ accounts for muscle pennation angles and ensures that an MTU's fiber length stays within physiological limits throughout the working range of the joint. The specific parameters for each muscle and joint are listed in Table 4. These values are either supported by experimental evidence [Muraoka, T., Kawakami, Y., Tachi, M., Fukunaga, T., 2001. Muscle fiber and tendon length changes in the human vastus lateralis during slow pedaling. J. Appl. Physiol. 91, 2035-2040; Maganaris, C., 2001. Force-length characteristics of in vivo human skeletal muscle. Acta Physiol. Scand. 172, 279-285; Maganaris, C., 2003. Force-length characteristics of the in vivo human gastrocnemius muscle. Clin. Anat. 16, 215-223; Oda, T., Kanehisa, H., Chino, K., Kurihara, T., Nagayoshi, T., Kato, E., Fukunaga, T., Kawakami, Y., 2005. In vivo length-force relationships on muscle fiver and muscle tendon complex in the tibialis anterior muscle. Int. J. Sport and Health Sciences 3, 245-252], or were obtained through rough anatomical estimates.

The seven segments of the human model are simple rigid bodies whose parameters are listed in Table 5. Their values are similar to those used in other modeling studies, for instance, in Günther and Ruder [Günther, M., Ruder, H., 2003. Synthesis of two-dimensional human walking: a test of the λ-model. Biol. Cybern. 89, 89-106]. The segments are connected by revolute joints. As in humans, these joints have free ranges of operation (70°<$\varphi_a$<130°, $\varphi_k$<175° and $\varphi_h$<230°) outside of which mechanical soft limits engage, which is modelled in the same way as the ground impact points. The model's segments have different masses ms and lengths $l_s$, and characteristic distances of their local center of mass, $d_{G,S}$, and joint location, $d_{J,S}$ (measured from distal end), and inertias $\Theta_S$.

TABLE 5

|  | Feet | Shanks | Thighs | HAT |
|---|---|---|---|---|
| $l_S$ (cm) | 20 | 50 | 50 | 80 |
| $d_{G,S}$ (cm) | 14 | 30 | 30 | 35 |
| $d_{J,S}$ (cm) | 16 | 50 | 50 | — |
| $m_S$ (kg) | 1.25 | 3.5 | 8.5 | 53.5 |
| $\Theta_S$ (kgm2) | 0.005 | 0.05 | 0.15 | 3 |

Ground contacts and joint limits. Each foot segment of the bipedal model has contact points at its toe and heel. When impacting the ground, a contact point (CP) gets pushed back by a vertical reaction force $F_y=-F_{ref}f_1f_v$, which, like the muscle force, is the product of a force-length relationship $f_1$ ($\Delta y_{CP}$)=$\Delta y_{CP}/\Delta y_{ref}$ and a force-velocity relationship $f_v$ ($dy_{CP}$/dt)=1 $dy_{CP}$/dt/$v_{max}$ (FIG. 9). This product approach to modeling vertical reaction forces is similar to existing approaches that describe the vertical force as the sum of a spring and a nonlinear spring-damper term [Scott, S., Winter, D., 1993. Biomechanical model of the human foot: kinematics and kinetics during the stance phase of walking. J. Biomech. 26 (9), 1091-1104; Gerritsen, K., van den Bogert, A., Nigg, B., 1995. Direct dynamics simulation of the impact phase in heel-toe running. J. Biomech. 28 (6), 661-668; Günther, M., Ruder, H., 2003. Synthesis of two-dimensional human walking: a test of the λ-model. Biol. Cybern. 89, 89-106]. By separating spring and damper terms, however, the parameters of the contact model can be interpreted as two basic material properties: a ground stiffness $k=F_{ref}/\Delta y_{ref}$ and a maximum relaxation speed $v_{max}$, which characterizes how quickly the ground surface can restore its shape after being deformed. For instance, $v_{max}=\infty$ describes a perfectly elastic ground impact where the ground always pushes back against the CP, and $v_{max}=0$ describes a perfectly inelastic impact where the ground, like sand, pushes back on the CP for downward velocities, but cannot push back for upward velocities. Note that the same impact model is used to describe the mechanical soft limits of the model's joints (see previous section) with a soft limit stiffness of 0.3N m deg$^{-1}$ and a maximum relaxation speed of 1 deg s$^{-1}$.

FIGS. 9A-C depict a contact model, according to one aspect of the present invention. In FIGS. 9A-C, contact occurs 910 if contact point 920 falls below $y_0$. The vertical ground reaction force $F_y$ is, like the muscle force, modeled as the product of a force-length ($f_l$) and a force-velocity relationship ($f_v$) with $\Delta y_{ref}$ being the ground compression at which $F_y=F_{ref}$ when dy/dt=0, and $dy_{ref}/dt$ being the maximum relaxation speed of the ground (small diagrams). Initially, the horizontal ground reaction force $F_x$ is modeled as sliding friction proportional to Fy with sliding coefficient $\mu_{sl}$. If however contact point 920 slows down 930 to below a minimum speed $v_{lim}$, the horizontal model switches to stiction 930. During stiction 930, $F_x$ is also modeled as the product of force-length and force-velocity relationships, which slightly differ from those earlier in order to allow for interactions with the ground in both directions around the stiction reference point $x_0$. The model switches back to sliding friction if $F_x$ exceeds the stiction limit force $\mu_{st} F_y$. Parameters: $F_{ref}=815N$, $\Delta y_{ref}=0.01$ m, $dy_{ref}/dt=0.03$ ms$^{-1}$, $\Delta x_{ref}=0.1$ m, $dx_{ref}/dt=0.03$ ms$^{-1}$, $v_{lim}=0.01$ ms$^{-1}$, $\mu_{sl}=0.8$, $\mu_{st}=0.9$.

In addition to the vertical reaction force, a horizontal reaction force is applied to the CP during ground contact. Initially, this force is modeled as a kinetic friction force that opposes the CP's motion on the ground with a force $F_x=\mu_{sl} F_y$. When the CP slows down to below a speed $v_{lim}$, the horizontal reaction force is modelled as a stiction force computed in a manner similar to that in which the vertical impact force is computed (FIGS. 9A-C). Stiction changes back to kinetic friction if the stiction force exceeds a limit force $F_{lim}=\mu_{st} F_y$. Thus, dependent on the transition conditions, both types of horizontal reaction force interchange until the CP leaves the ground surface.

The results suggest that mechanics and motor control cannot be viewed separately in human locomotion. A neuromuscular model of human locomotion according to one aspect of the invention self-organizes into the walking gait after an initial push, tolerates sudden changes in ground level, and adapts to stair walking without interventions. Central to this model's tolerance and adaptiveness is its reliance on muscle reflexes, which integrate sensory information about locomotion mechanics into the activation of the leg muscles. Having no CPG, the model shows that in principle no central input is required to generate walking motions, suggesting that reflex inputs that continuously mediate between the nervous system and its mechanical environment may even take precedence over central inputs in the control of normal human locomotion.

In addition, the model results suggest that these continuous reflex inputs encode principles of legged mechanics. Current experimental and modeling research on the role of spinal reflexes during locomotion focuses on their contribution to the timing of swing and stance phases and to the production of muscle force in load bearing extensor muscles [Pang, M. Y., Yang, J. F., 2000. The initiation of the swing phase in human infant stepping: importance of hip position and leg loading. J Physiol 528 Pt 2, 389-404; Dietz, V., 2002. Proprioception and locomotor disorders. Nat Rev Neurosci 3 (10), 781-790; Ivashko, D. G., Prilutsky, B. I., Markin, S. N., Chapin, J. K., Rybak, I. A., 2003. Modeling the spinal cord neural circuitry controlling cat hindlimb movement during locomotion. Neurocomputing 52-54, 621-629; Yakovenko, S., Gritsenko, V., Prochazka, A., 2004. Contribution of stretch reflexes to locomotor control: a modeling study. Biol Cybern 90 (2), 146-155; Ekeberg, O., Pearson, K., 2005. Computer simulation of stepping in the hind legs of the cat: an examination of mechanisms regulating the stance-to-swing transition. J Neurophysiol 94 (6), 4256-4268; Maufroy, C., Kimura, H., Takase, K., 2008. Towards a general neural controller for quadrupedal locomotion. Neural Netw 21 (4), 667-681; Donelan, J. M., Pearson, K. G., 2004. Contribution of sensory feedback to ongoing ankle extensor activity during the stance phase of walking. Can J Physiol Pharmacol 82 (8-9), 589-598; Frigon, A., Rossignol, S., 2006. Experiments and models of sensorimotor interactions during locomotion. Biol Cybern 95 (6), 607-627; Grey, M. J., Nielsen, J. B., Mazzaro, N., Sinkjaer, T., 2007. Positive force feedback in human walking. J Physiol 581 (1), 99-105]. The reflex contribution to load bearing has started to link positive force feedback to the underlying dynamics of the locomotor system [Prochazka, A., Gillard, D., Bennett, D., 1997. Positive force feedback control of muscles. J. of Neurophys. 77, 3226-3236; Geyer, H., Seyfarth, A., Blickhan, R., 2003. Positive force feedback in bouncing gaits? Proc. R. Soc. Lond. B 270, 2173-2183]. There appears to be no previous work that systematically expands on the idea of encoding principles of legged dynamics in the motor control system. While some of the muscle reflexes implemented in the human model were simple expedients to let it enter cyclic motions (trunk balance, swing-leg initiation), mainly the stance phase reflexes encoded principles of legged dynamics and control described previously, including compliant stance leg behavior [Blickhan, R., 1989. The spring-mass model for running and hopping. J. of Biomech. 22, 1217-1227; McMahon, T., Cheng, G., 1990. The mechanism of running: how does stiffness couple with speed? J. of Biomech. 23, 65-78; Geyer, H., Seyfarth, A., Blickhan, R., 2006. Compliant leg behaviour explains the basic dynamics of walking and running. Proc. R. Soc. Lond. B 273, 2861-2867], stabilization of segmented chains [Seyfarth, A., Günther, M., Blickhan, R., 2001. Stable operation of an elastic three-segmented leg. Biol. Cybern. 84, 365-382; Günther, M., Keppler, V., Seyfarth, A., Blickhan, R., 2004. Human leg design: optimal axial alignment under constraints. J. Math. Biol. 48, 623-646], and swing-leg retraction [Herr, H., McMahon, T., 2000. A trotting horse model. Int. J. Robotics Res. 19, 566-581; Herr, H., McMahon, T., 2001. A galloping horse model. Int. J. Robotics Res. 20, 26-37; Herr, H. M., Huang, G. T., McMahon, T. A., April 2002. A model of scale effects in mammalian quadrupedal running. J Exp Biol 205 (Pt 7), 959-967; Seyfarth, A., Geyer, H., 2002. Natural control of spring-like running—optimized self-stabilization. In: Proceedings of the 5th international conference on climbing and walking robots. Professional Engineering Publishing Limited, pp. 81-85; Seyfarth, A., Geyer, H., Herr, H. M., 2003. Swing-leg retraction: a simple control model for stable running. J. Exp. Biol. 206, 2547-2555]. Based on these functional reflexes, the model not only converges to known joint angle and torque trajectories of human walking, but also predicts some individual muscle activation patterns observed in walking experiments. This match between predicted and observed muscle activations suggests that principles of legged mechanics could play a larger role in motor control than anticipated before, with muscle reflexes linking these principles into the neural networks responsible for locomotion.

In a preferred embodiment, the neuromechanical model of the invention has been implemented as a muscle reflex controller for a powered ankle-foot prosthesis. This embodiment is an adaptive muscle-reflex controller, based on simulation studies, that utilizes an ankle plantar flexor comprising a Hill-type muscle with a positive force feedback reflex. The model's parameters were fitted to match the human ankle's torque-angle profile as obtained from level-ground walking measurements of a weight and height-matched intact subject walking at 1 m/sec. Using this single parameter set, clinical trials were conducted with a transtibial amputee walking on level ground, ramp ascent, and ramp descent conditions. During these trials, an adaptation of prosthetic ankle work was observed in response to ground slope variation, in a manner comparable to intact subjects, without the difficulties of explicit terrain sensing. Specifically, the energy provided by the prosthesis was directly correlated to the ground slope angle. This study highlights the importance of neuromuscular controllers for enhancing the adaptiveness of powered prosthetic devices across varied terrain surfaces.

In order to produce a controller with the ability to adapt, the neuromuscular model with a positive force feedback reflex scheme as the basis of control of the invention was used as part of the control system for a powered ankle-foot prosthesis. The controller presented here employs a model of the ankle-foot complex for determining the physical torque to command at the ankle joint. In this model, the ankle joint is provided with two virtual actuators. For plantar flexion torque, the actuator is a Hill-type muscle with a positive force feedback reflex scheme. This scheme models the reflexive muscle response due to some combination of afferent signals from muscle spindles and Golgi tendon organs. For dorsiflexion torque, an impedance is provided by a virtual rotary spring-damper.

The parameters of this neuromuscular model were fitted by an optimization procedure to provide the best match between the measured ankle torque of an intact subject walking at a target speed of 1.0 m/sec, and the model's output torque when given as inputs the measured motion of the intact subject. The neuromuscular model-based prosthetic controller was used to provide torque commands to a powered ankle-foot prosthesis worn by an amputee. This control strategy was evaluated using two criteria. First, the controller was tested for the ability to produce prosthesis ankle torque and ankle angle profiles that qualitatively match those of a comparable, intact subject at a target level-ground walking speed. The second performance criterion was the controller's ability to exhibit a biologically-consistent trend of increasing gait cycle net-work for increasing walking slope without changing controller parameters. Detecting variations in ground slope is difficult using typical sensors, so a controller with an inherent ability to adapt to these changes is of particular value.

Figure 10A:
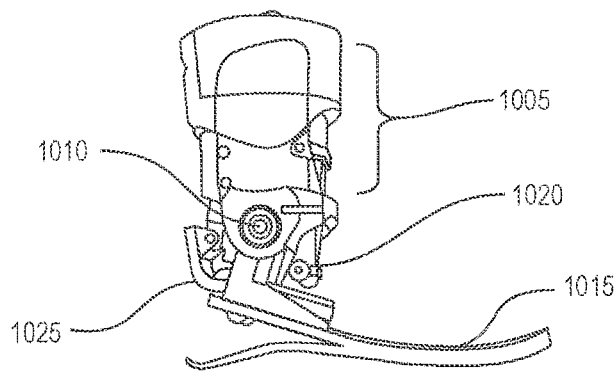
FIGS. 10A-C depict an exemplary embodiment of an ankle-foot prosthesis used in a preferred embodiment, depicting the physical system (FIG. 10A), a diagram of the drive train (FIG. 10B), and a mechanical model (FIG. 10C), respectively, according to one aspect of the present invention.
Figure 10B:
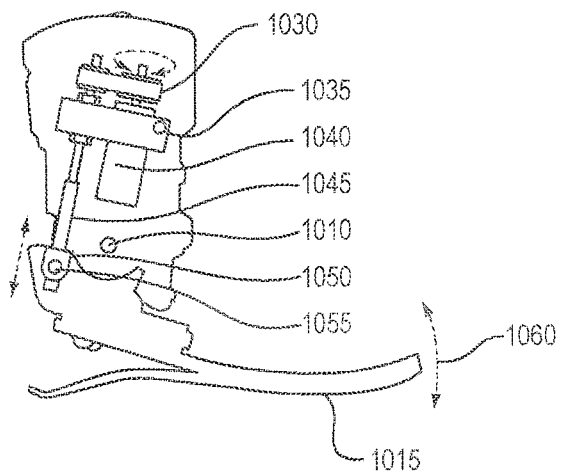
Figure 10C:
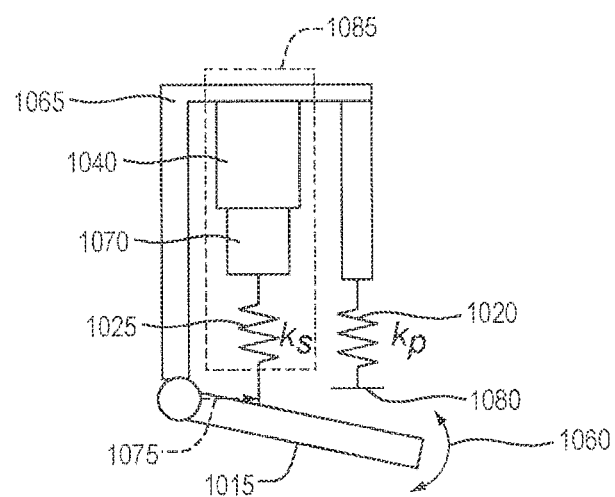

FIGS. 10A-C depict the physical system (FIG. 10A), a diagram of the drive train (FIG. 10B), and a mechanical model (FIG. 10C) for an exemplary embodiment of an ankle-foot prosthesis used in a preferred embodiment. The ankle-foot prosthesis used for this study is one in development by iWalk, LLC. This prosthesis is a successor to the series of prototypes developed in the Biomechatronics Group of the MIT Media Laboratory, which are described in U.S. patent application Ser. No. 12/157,727, filed Jun. 12, 2008, the entire disclosure of which has been incorporated by reference herein in its entirety. The prosthesis is a completely self-contained device having the weight (1.8 kg) and size of the intact biological ankle-foot complex. Seen in FIG. 10A are housing 1005 for the motor, transmission, and electronics, ankle joint 1010, foot 1015, unidirectional parallel leaf spring 1020, and series leaf spring 1025. Depicted in FIG. 10B are timing belt 1030, pin joint main housing 1035, motor 1040, ball screw 1045, ankle joint 1010, ball nut 1050 pin joint (series spring) 1055, and foot motion indicator 1060. Depicted in the mechanical model of FIG. 10C are parent link 1065, motor 1040, transmission 1070, series spring 1025, unidirectional parallel spring 1020, foot 1015, series spring movement arm $r_s$ 1075, spring rest length 1080, and SEA 1085. The rotary elements in the physical system are shown as linear equivalents in the model schematic for clarity.

The ankle joint is a rolling bearing design joining a lower foot structure to an upper leg shank structure topped with a prosthetic pyramid fixture for attachment to the amputee's socket. The foot includes a passive low profile Flex-Foot™ (Osur™) to minimize ground contact shock to the amputee. A unidirectional leaf spring, the parallel spring, acts across the ankle joint, engaging when the ankle and foot are perpendicular to each other. It acts in parallel to a powered drive train, providing the passive function of an Achilles tendon. The powered drive train is a motorized link across the ankle joint as represented in FIG. 10B. From the upper leg shank end, it consists, in series, of a brushless motor, (Powermax EC-30, 200 Watt, 48V, Maxon) operating at 24V, a belt drive transmission with 40/15 reduction, and a 3 mm pitch linear ball screw. At this operating voltage, the theoretical maximum torque that can be generated by the motor through the drivetrain is approximately 340 Nm.

At the foot, the series spring, a Kevlar-composite leaf spring, connects the foot to the ball nut with a moment arm, $r_s$, that is direction-dependent. Therefore, the effective rotary stiffness of the series spring, as evaluated by locking the drive train and exerting a torque about the ankle joint, is 533 N·m/rad for positive torque, and 1200 N·m/rad for negative torque, where positive torque (or plantar flexion torque) is that tending to compress the series spring as represented in FIG. 10C. The drive train and the series spring together comprise a series-elastic actuator (SEA) [G. A. Pratt and M. M. Williamson, "Series elastic actuators," Proceedings on IEEE/RSJ International Conference on Intelligent Robots and Systems, Pittsburgh, pp. 399-406, 1995]. The arrangement of these components is shown schematically in FIG. 10C.

Sensors. A hall-effect angle sensor at the ankle joint is a primary control input, and has a range of −0.19 to 0.19 radians, where zero corresponds to the foot being perpendicular to the shank. Joint angle is estimated with a linear hall-effect sensor (Allegro A1395) mounted on the main housing. This sensor is proximate to a magnet that is rigidly connected to the foot structure so that the magnetic axis is tangent to the arc of the magnet's motion. As a result of this arrangement, the magnetic field strength at the sensor location varies as the magnet rotates past the sensor. Strain gauges are located inside the prosthetic pyramid attachment, allowing for an estimate of the torque at the ankle joint. Strain gauges located on the series spring permit sensing of the output torque of the motorized drive train, thereby allowing for closed-loop force control of the SEA. The motor itself contains Hall-effect commutation sensors and is fitted with an optical shaft encoder that enables the use of advanced brushless motor control techniques.

Microcontroller. Overall control and communications for the ankle-foot prosthesis are provided by a single-chip, 16-bit, DSP oriented microcontroller, the Microchip Technology Incorporated dsPIC33FJ128MC706. The microcontroller operates at 40 million instructions per second, with 128 kilo-bytes of flash program memory, and 16384 bytes of RAM. It provides adequate computation to support real time control.

Motor Controller. A second 16-bit dsPIC33FJ128MC706 was used as a dedicated motor controller. The high computation load and speed requirements of modern brushless motor control methodologies, along with task isolation from the main microcontroller's real time demands motivated this architecture. A high speed digital link between the main microcontroller and the motor microcontroller supplied virtually instantaneous command of the motor.

Wireless Interface. For development and data collection, a high speed serial port of the microcontroller is dedicated to external communications. This port may be used directly via cable or may have a wide variety of wireless communication devices attached. For the present study, the 500 Hz sensor and internal state information is telemetered over the serial port at 460 Kilobaud and transmitted via an IEEE 802.11g wireless local area network device (Lantronix Wiport).

Battery. All power for the prosthesis was provided by a 0.22 kg lithium polymer battery having a 165 Watt-Hour/kg energy density. The battery was able to provide a day's power requirements including 5000 steps of powered walking.

Optimal Mechanical Component Selection. Meeting the requirements for mass, size, torque, speed, energy efficiency, shock tolerance, and nearly silent operation is not a trivial task. Of particular importance is the modeling and optimization of the drive train for the production of the biological torques and motions of walking. Some effects of the motor selection, overall transmission ratio, series elastic spring, and parallel spring are described in S. K. Au, H. Herr, "On the Design of a Powered Ankle-Foot Prosthesis: The Importance of Series and Parallel Elasticity," IEEE Robotics & Automation Magazine. pp. 52-59, September 2008.

Control Architecture. The purpose of the control architecture is to command an ankle torque appropriate to the amputee's gait cycle as determined from available sensor measurements of prosthetic ankle state. The controller determines the appropriate torque using a neuromuscular model of the human ankle-foot complex. In this model, a hinge joint, representing the human ankle joint, is actuated by two competing virtual actuators: a unidirectional plantar flexor which is a Hill-type muscle model, and a dorsiflexor which acts as either a bi-directional proportional-derivative position controller, or a unidirectional virtual rotary spring-damper, depending on the gait phase. A finite state machine maintains an estimate of the phase of the amputee's gait. Depending on this estimated gait phase, one or the other, or both of the virtual actuators produce torques at the virtual ankle joint. The net virtual torque is then used as the ankle torque command to the prosthesis hardware. Physical torque at the ankle joint is produced by both the motorized drive train and the parallel spring. The ankle angle sensor is used to determine the torque produced by the parallel spring, and the remaining desired torque is commanded through the motor controller.

Figure 11:
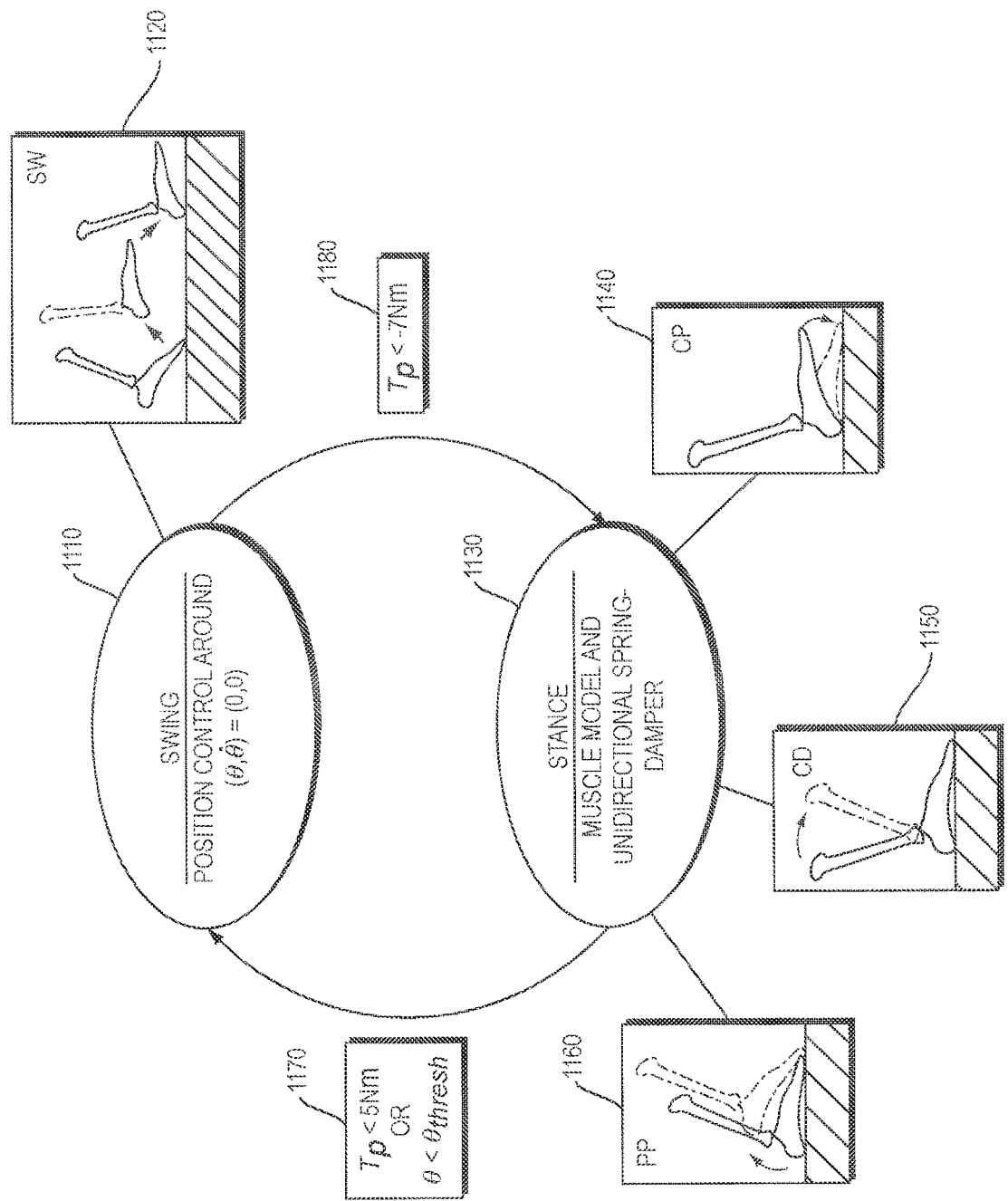
FIG. 11 is a diagram of an exemplary embodiment of a finite state machine synchronized to the gait cycle, with state transition thresholds and equivalent ankle-foot biomechanics during each state, used to implement top level control of the ankle-foot prosthesis of FIGS. 10A-C, according to one aspect of the present invention.

Top Level State Machine Control. Top level control of the prosthesis is implemented by a finite state machine synchronized to the gait cycle. During walking, two states are recognized: swing phase and stance phase. Prosthesis sensor inputs (ankle torque as estimated from the pyramid strain gauges, ankle angle, and motor velocity) are continuously observed to determine state transitions. Conditions for these state transitions were experimentally determined. FIG. 11 depicts the operation of the state machine and the transition conditions. The dorsiflexor and plantar flexor virtual actuators develop torque depending on the gait state estimate from the state machine.

In FIG. 11, the swing state 1110 is visually depicted as SW 1120, and stance 1130 is divided into controlled plantar flexion (CP) 1140, controlled dorsiflexion (CD) 1150, and powered plantar flexion (PP) 1160. State transitions 1170, 1180 are determined using the prosthesis ankle torque, $T_P$, as measured from the pyramid strain gauges, and prosthesis ankle angle, $\theta$.

The transition to swing phase when the foot leaves the ground is detected by either a drop in total ankle torque to less than 5 N·m, as measured using the pyramid strain gauges, or a drop in measured ankle angle, 0, below −0.19 radians to prevent angle sensor saturation. Positive torque is defined as actuator torque tending to plantar flex the ankle, and positive angles correspond to dorsiflexion. To prevent premature state transitions, the ankle torque developed during the stance phase must exceed 20 N·m for these transitions to be enabled. In addition, a 200 ms buffer time provides a minimum time frame for the stance period. The transition to stance phase upon heel-strike is detected by a decrease in torque below −7 N·m as measured using the pyramid strain gauges.

Figure 12:
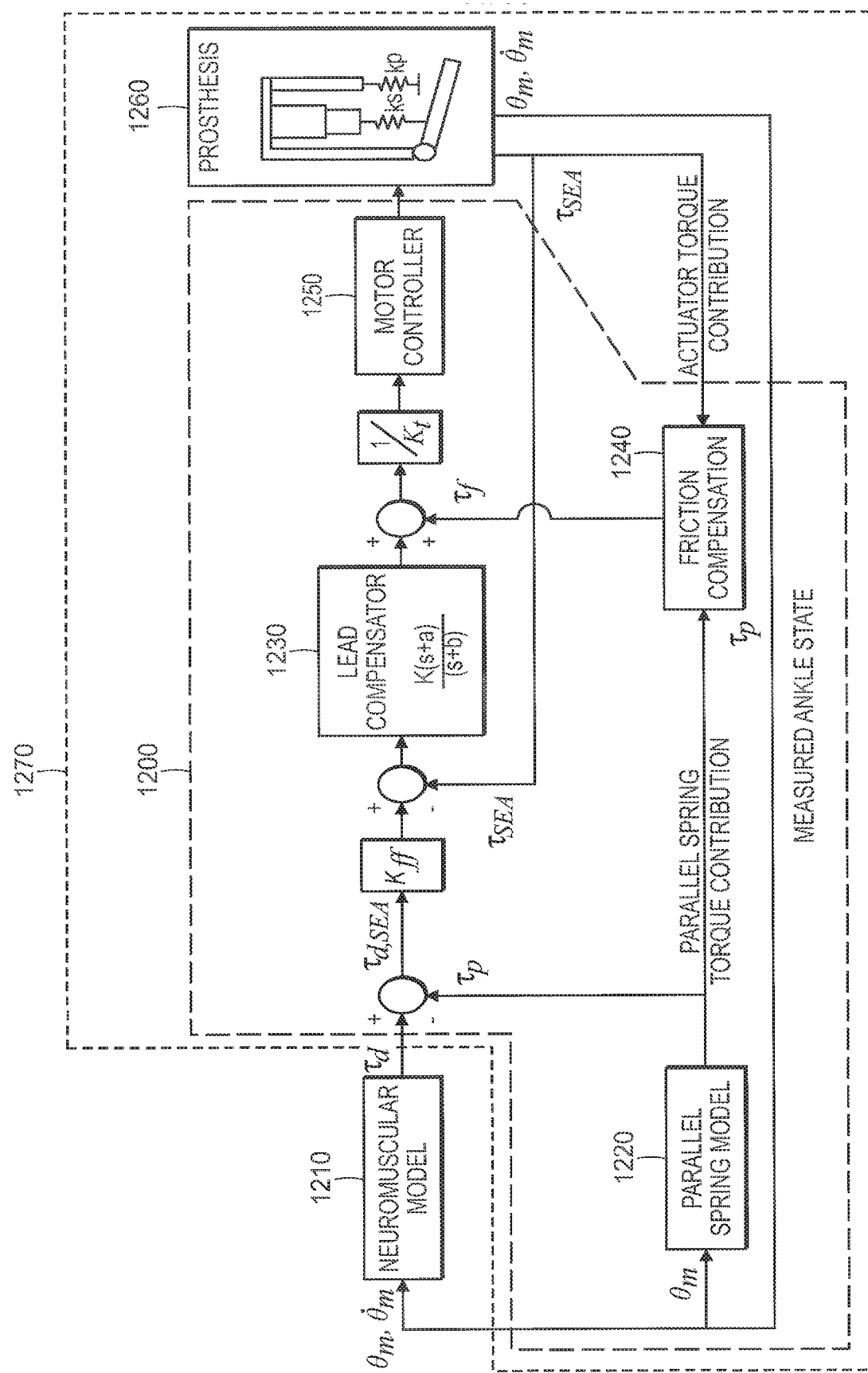
FIG. 12 is a block diagram of an exemplary embodiment of a control system for an ankle-foot prosthesis, according to one aspect of the present invention.

A block diagram of an exemplary embodiment of a control system for an ankle-foot prosthesis according to this aspect of the invention is shown in FIG. 12. Depicted in FIG. 12 are neuromuscular model 1210 and biomimetic robotic limb 1270. Robotic limb 1270 includes torque control system 1200 and robotic limb joint 1260. Torque control system 1200 includes parallel spring model 1220, lead compensator 1230, friction compensator 1240, and motor controller 1250.

The prosthesis measured ankle state, $(\theta_m, \theta'_m)$ is used to produce a torque command from the neuromuscular model, $\tau_d$. This desired ankle torque is fed through a torque control system to obtain a current command to the prosthesis actuator. The three primary components of this torque control system are the feedforward gain $K_{ff}$, lead compensator, and friction compensation term. The parallel spring contribution to prosthesis ankle torque, $\tau_p$, is subtracted from the desired ankle torque to obtain the desired actuator torque $\tau_{d,SEA}$. The closed-loop torque controller then enforces the desired actuator torque using the measured actuator torque, $\tau_{SEA}$. Finally, the friction compensation term produces an additional torque value, $\tau_f$ which is added to the output of the closed-loop torque controller.

Figure 13A:
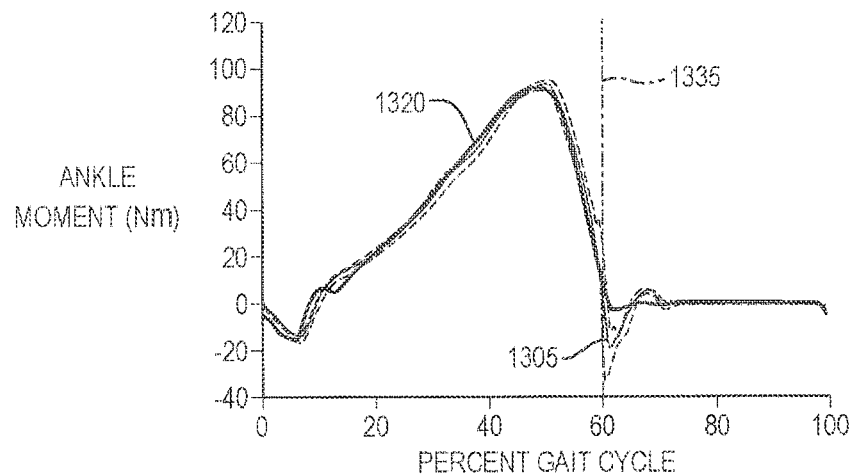
FIGS. 13A-C are exemplary plots of prosthesis torque over one complete gait cycle for three walking conditions: level-ground (FIG. 13A), ramp ascent (FIG. 13B), and ramp descent (FIG. 13C), according to one aspect of the present invention.
Figure 13B:
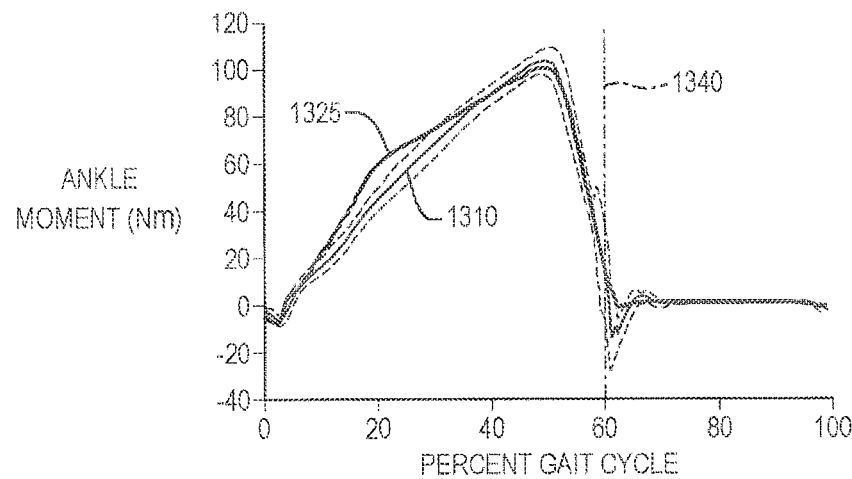
Figure 13C:
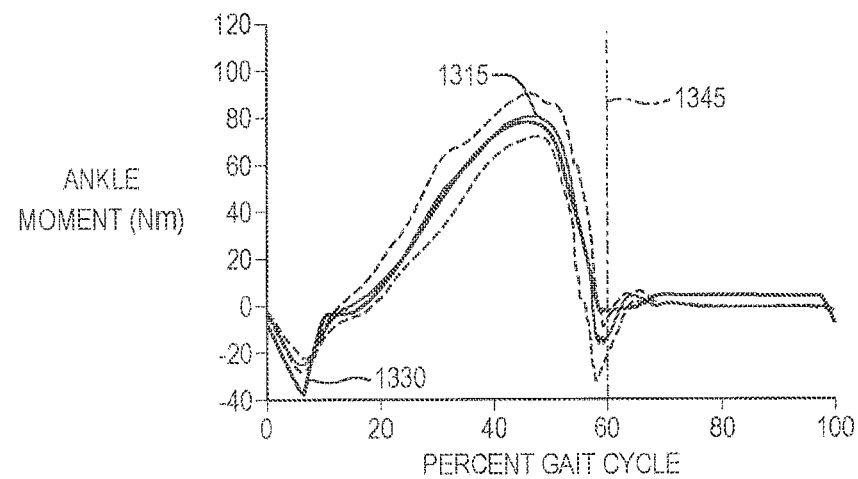

FIGS. 13A-C are plots of prosthesis torque over one complete gait cycle (heel-strike to heel-strike of the same foot) for three walking conditions: level-ground (FIG. 13A), ramp ascent (FIG. 13B), and ramp descent (FIG. 13C). Shown for each are commanded torque mean 1305, 1310, 1315 (thin line)±standard deviation (dashed lines), and prosthesis torque, as estimated using the measured SEA torque contribution and angle-based estimate of the parallel spring torque contribution 1320, 1325, 1330 (thick line). Vertical (dash-dot) lines 1335, 1340, 1345 indicate the end of the stance phase.

Figure 14A:
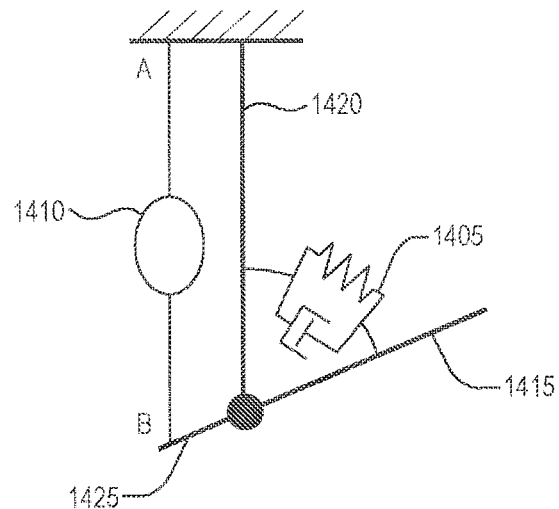
FIGS. 14A-C depict an exemplary embodiment of the musculoskeletal model as implemented on the prosthetic microcontroller, including the two-link ankle joint model (FIG. 14A), detailed Hill-type muscle model (FIG. 14B), and geometry of the muscle model skeletal attachment (FIG. 14C), according to one aspect of the present invention.
Figure 14B:
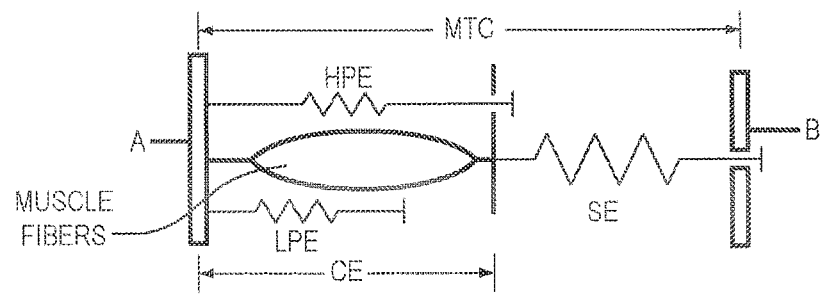
Figure 14C:
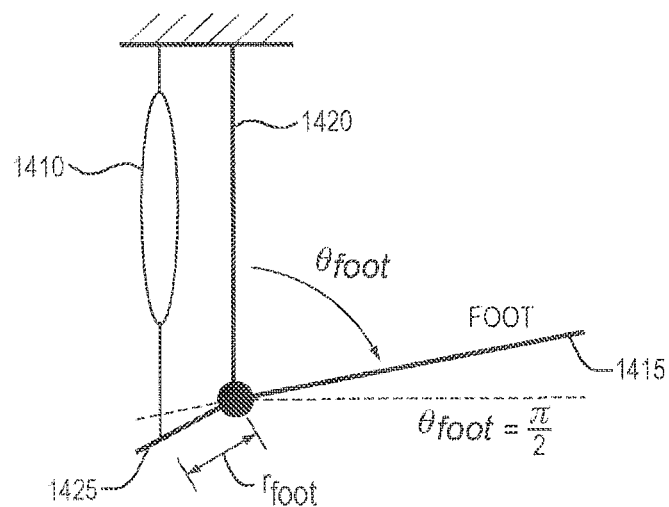

Dorsiflexor Model. FIGS. 14A-C depict an exemplary embodiment of the musculoskeletal model as implemented on the prosthetic microcontroller, including the Hill-type muscle model and spring-damper attachments to the two-link ankle joint model (FIG. 14A), detailed Hill-type muscle model (FIG. 14B), and geometry of the muscle model skeletal attachment (FIG. 14C) including the variable moment-arm implementation and angle coordinate frame for the muscle model. Depicted in FIGS. 14A and 14C are mechanical representations of dorsiflexor (spring-damper) 1405, planar flexor (MTC) 1410, foot 1415, shank 1420, and heel 1425.

The dorsiflexor in FIG. 14A is the dorsiflexor actuator. It represents the Tibialis Anterior and other biological dorsiflexor muscles. This dorsiflexor is implemented as a virtual rotary spring-damper with a set point of [θ=0, θ'=0] and relation:

$$T_{dorsi}=K_P\theta+K_V\theta' \quad (1)$$

Here, $K_P$ is the spring constant, and $K_v$ is the damping constant, θ is the ankle angle and θ' is the ankle angular velocity. For the stance phase, the value of $K_P$ was optimized along with other muscle model parameters to best match the stance phase behavior of the biological ankle for normal level-ground walking. The damping term, $K_V$, was experimentally tuned for stance phase to 5 Nm-s/rad to prevent the forefoot from bouncing off the ground at foot-flat. Also during the stance phase, the dorsiflexor acts only to provide dorsiflexion torque, so to mimic the unidirectional property of biological muscles. Furthermore, when the torque generated by the dorsiflexor drops to zero during stance as a result of the foot becoming perpendicular to the shank, the dorsiflexor is disabled for the remainder of the stance phase. Therefore, the dorsiflexor only contributes to the torque production early in the stance phase, when human dorsiflexor muscles are known to play a significant role [J. Perry, Gait Analysis: Normal and Pathological Function, New Jersey: SLACK Inc., 1992, Chapter 4, pp. 55-57]. In the swing phase, the dorsiflexor acts as a position controller, driving the foot to the set-point [θ=0, θ'=0]. For this, a gain of $K_P$=220 N·m/rad and damping constant of $K_V$=7 N·m·s/rad provides for quick ground clearance of the foot early in the swing phase.

Plantar Flexor Model. The virtual plantar flexor in FIGS. 14A-C comprises a muscle-tendon complex, (MTC) which represents a combination of human plantar flexor muscles. The MTC is based on S. K. Au, J. Weber, and H. Herr, "Biomechanical design of a powered ankle-foot prosthesis," Proc. IEEE Int. Conf. On Rehabilitation Robotics, Noordwijk, The Netherlands, pp. 298-303, June 2007, where it is discussed in further detail. It consists of a contractile element (CE) which models muscle fibers and a series element (SE) which models a tendon. The contractile element consists of three unidirectional components: a Hill-type muscle with a positive force feedback reflex scheme, a high-limit parallel elasticity, and a low-limit, or buffer, parallel elasticity. In series with the contractile element is the series element, which is a nonlinear, unidirectional spring representing the Achilles tendon. The attachment geometry of the muscle-tendon complex to the ankle joint model is nonlinear, complicating the calculation of torques resulting from the actuator force.

Plantar Flexor Series Elastic Element. The series elastic element (SE) operates as a tendon in series with the muscle contractile element as in [H. Geyer, A. Seyfarth, R. Blickhan, "Positive force feedback in bouncing gaits?," Proc. R Society. Lond. B 270, pp. 2173-2183, 2003]. Taking ε as the tendon strain defined as:

$$\varepsilon = \frac{l_{SE} - l_{slack}}{l_{slack}}, \quad (2)$$

where $l_{SE}$ is the length of the series element and $l_{slack}$ is its rest length, the series element is specified to be a nonlinear spring described by H. Geyer, A. Seyfarth, R. Blickhan, "Positive force feedback in bouncing gaits?," Proc. R Society. Lond. B 270, pp. 2173-2183, 2003:

$$F_{SE} = \begin{cases} F_{max}\left(\dfrac{\varepsilon}{\varepsilon_{ref}}\right)^2, & \varepsilon > 0 \\ 0, & \varepsilon \leq 0 \end{cases} \quad (3)$$

where $F_{max}$ is the maximum isometric force that the muscle can exert. Following H. Geyer, A. Seyfarth, R. Blickhan, "Positive force feedback in bouncing gaits?," Proc. R Society. Lond. B 270, pp. 2173-2183, 2003, this quadratic form was used as an approximation of the commonly-modeled piecewise exponential-linear tendon stiffness curve. This approximation was made so to reduce the number of model parameters.

Plantar Flexor Contractile Element. The contractile element (CE) of the plantar flexor virtual actuator, FIG. 14B, is a Hill-type muscle model with a positive force feedback reflex scheme. It includes active muscle fibers to generate force, and two parallel elastic components, as in H. Geyer, H. Herr, "A muscle-reflex model that encodes principles of legged mechanics predicts human walking dynamics and muscle activities," (Submitted for publication). The Hill-type muscle fibers exert a unidirectional force. This force is a function of the muscle fiber length, $l_{CE}$, velocity, $v_{CE}$, and muscle activation, A. The resulting force, $F_{MF}$ is, as in H. Geyer, A. Seyfarth, R. Blickhan, "Positive force feedback in bouncing gaits?," Proc. R Society. Lond. B 270, pp. 2173-2183, 2003, given by:

$$F_{MF}(l_{CE},v_{CE},A)=F_{max}f_L(l_{CE})f_V(v_{CE})A. \quad (4)$$

The force-length relationship, $f_L(l_{CE})$, of the Hill-type muscle is a bell-shaped curve given by:

$$f_L(l_{CE}) = \exp\left[c\left|\frac{l_{CE} - l_{opt}}{l_{opt}w}\right|^3\right], \quad (5)$$

where, $l_{opt}$ is the contractile element length, $l_{CE}$, at which the muscle can provide the maximum isometric force, $F_{max}$. The parameter w is the width of the bell-shaped curve, and the parameter c describes the curve's magnitude near the extremes of the bell, where:

$$f_L(l_{CE}=(1\pm w)l_{opt})=\exp(c). \quad (6)$$

The force-velocity relationship, $f_v(v_{CE})$, of the CE is the Hill equation:

$$f_L(v_{CE}) = \begin{cases} \dfrac{v_{max} - v_{CE}}{v_{max} + Kv_{CE}}, & v_{CE} < 0 \\ N + (N-1)\dfrac{v_{max} + v_{CE}}{7.56Kv_{CE} - v_{max}}, & v_{CE} \geq 0 \end{cases} \quad (7)$$

where $v_{max}$<0 is the maximum contractile velocity of the muscle, $v_{CE}$ is the fiber contraction velocity, K is the curvature constant, and N defines the dimensionless muscle force (normalized by $F_{max}$) such that $$N=f_v(v_{CE}=-v_{max}) \quad (8)$$

Following H. Geyer, H. Herr, "A muscle-reflex model that encodes principles of legged mechanics predicts human walking dynamics and muscle activities," (Submitted for publication), the force-length relationship for the high-limit parallel elasticity (HPE), set in parallel with the CE, is given by:

$$F_{HPE}(l_{CE}) = \begin{cases} F_{max}\left(\dfrac{l_{CE} - l_{opt}}{l_{opt} w}\right)^2, & l_{CE} - l_{opt} \\ 0, & \text{otherwise} \end{cases} \quad (9)$$

A low-limit, buffer parallel elasticity (LPE) is also included, based on H. Geyer, H. Herr, "A muscle-reflex model that encodes principles of legged mechanics predicts human walking dynamics and muscle activities," (Submitted for publication). This was given the form of the nonlinear spring:

$$F_{LPE}(l_{CE}) = \begin{cases} F_{max} \dfrac{\left[\dfrac{(l_{CE} - l_{opt}(1-w))}{l_{opt}}\right]^2}{(w/2)}, & l_{CE} \le l_{opt}(1-w) \\ 0, & \text{otherwise} \end{cases} \quad (10)$$

Therefore, the total plantar flexor force is described by:

$$F_{CE} = F_{MF}(l_{CE}, v_{CE}, A) + F_{HPE} - F_{LPE} \quad (11)$$

Where $F_{CE}$ is the force developed by the contractile element. Since the CE and SE are in series, the following equation holds: $F_{CE} = F_{SE} = F_{MTC}$.

Figure 15:
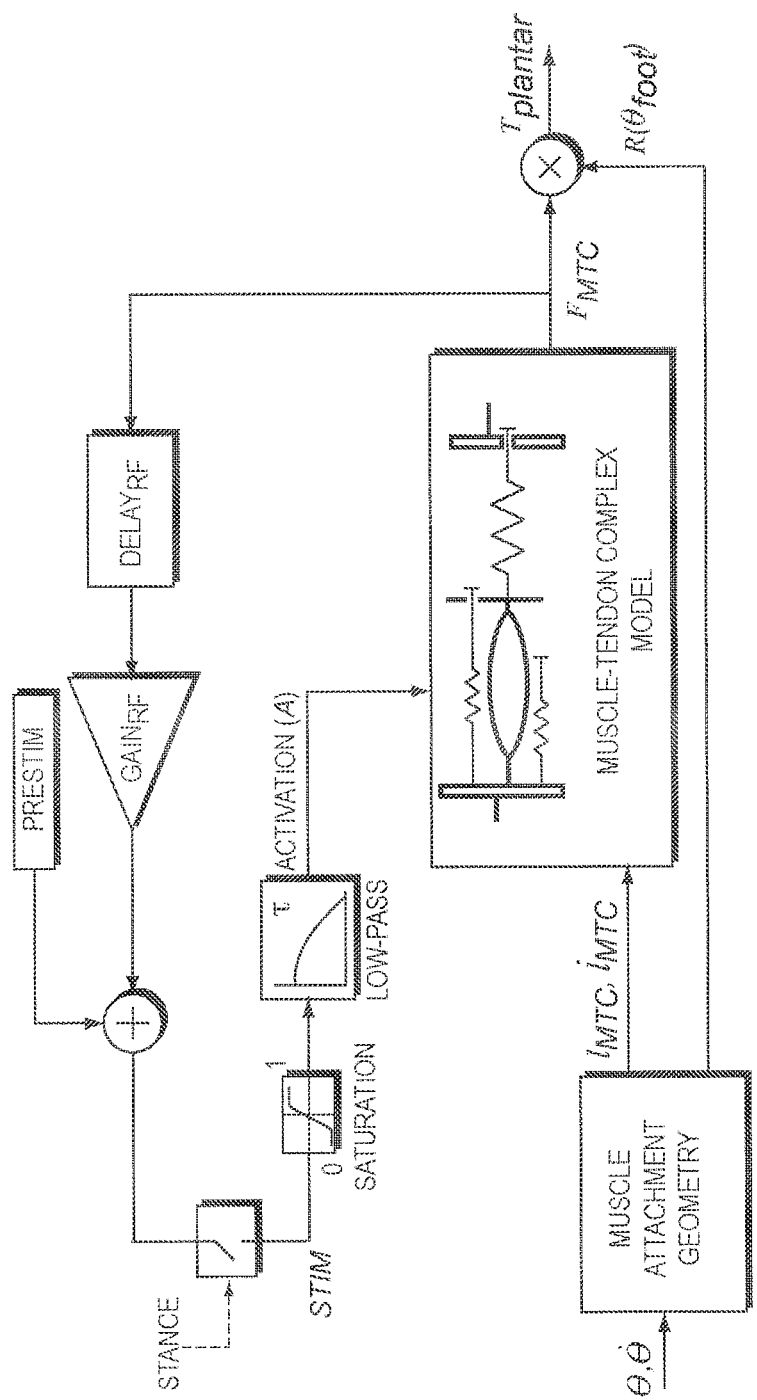
FIG. 15 depicts an exemplary embodiment of a reflex scheme for the virtual plantar flexor muscle, including the relationship among ankle angle, muscle force, and the plantar flexor component of ankle torque, according to one aspect of the present invention.

Reflex Scheme. The contractile element activation, A, is generated using the positive-force feedback reflex scheme shown in FIG. 15, as in [H. Geyer, H. Herr, "A muscle-reflex model that encodes principles of legged mechanics predicts human walking dynamics and muscle activities," (Submitted for publication); H. Geyer, A. Seyfarth, R. Blickhan, "Positive force feedback in bouncing gaits?," Proc. R Society. Lond. B 270, pp. 2173-2183, 2003]. FIG. 15 depicts an exemplary embodiment of a reflex scheme for the virtual plantar flexor muscle, including the relationship among ankle angle, muscle force, and the plantar flexor component of ankle torque.

As depicted in FIG. 15, this feedback loop includes a stance phase switch for disabling the plantar flexor force development during the swing phase. During stance, the plantar flexor force, $F_{MTC}$, is multiplied by a reflex gain $Gain_{RF}$, delayed by $Delay_{RF}$ and added to an offset stimulation, PRESTIM to obtain the neural stimulation signal. The stimulation is constrained to range from 0 to 1, and is low-pass filtered with time constant T to simulate the muscle excitation-contraction coupling. The resulting signal is used as activation in equation (4) with an initial value of PreA. In addition, a suppression gain, $Gain_{SUPP}$, following H. Geyer, H. Herr, "A muscle-reflex model that encodes principles of legged mechanics predicts human walking dynamics and muscle activities," (Submitted for publication), was implemented to help prevent the two actuators from fighting each other during stance. Here, the torque generated by the dorsiflexor is reduced by either $Gain_{SUPP} \cdot F_{MTC}$ or until its value drops to zero.

Plantar Flexor Geometry and Implementation. Within the muscle model framework, the ankle angle, $\theta_{foot}$, is defined as shown in FIG. 14C. Using this angle as the input to the model, the length of the muscle-tendon complex is calculated as in H. Geyer, H. Herr, "A muscle-reflex model that encodes principles of legged mechanics predicts human walking dynamics and muscle activities," (Submitted for publication) by:

$$l_{MTC} = r_{foot}\rho(\sin(\phi_{ref} - \theta_{max}) - \sin(\theta_{foot} - \phi_{max})) + l_{slack} + l_{opt}. \quad (12)$$

where $\rho$ is a scaling factor representing the pennation angle of the muscle fibers, and $\phi_{ref}$ is the ankle angle at which $l_{CE} = l_{opt}$ under no load.

The fiber length, $l_{CE}$ can be computed using $l_{CE} = l_{MTC} - l_{SE}$, where $l_{SE}$ is obtained from the inverse of (3) given the current value of $F_{CE} = F_{SE} = F_{MTC}$ from the muscle dynamics. The fiber contraction velocity, $v_{CE}$, can then be obtained via differentiation. This creates a first order differential equation governed by the dynamics of the neuromuscular model. This equation can be solved for $F_{MTC}$ given the time history of $\theta_{foot}$ and initial condition. However, since integration is computationally more robust than differentiation, an integral form of this implementation was used to solve for $F_{MTC}$, as described in H. Geyer, H. Herr, "A muscle-reflex model that encodes principles of legged mechanics predicts human walking dynamics and muscle activities," (Submitted for publication).

Given the attachment radius, $r_{foot}$, and the angle, $\phi_{max}$, at which maximum muscle-tendon moment arm is realized, the relationship between $F_{MTC}$ and the resulting plantar flexor contribution to ankle torque, $T_{plantar}$, is given by $$T_{plantar} = F_{MTC} \cos(\theta_{foot} - \phi_{max}) r_{foot} = F_{MTC} \cdot R(\theta_{foot}) \quad (13)$$

where $R(\theta_{foot})$ is a variable moment arm resulting from the muscle attachment to the ankle joint model. This relationship is shown graphically in FIG. 15. Hence, the plantar flexor model can ultimately be treated as a dynamical system linking a single input, $\theta_{foot}$, to a single output, $T_{plantar}$.

Neuromuscular Model Parameter Determination. The plantar flexor model is a lumped representation of all of the biological plantar flexor muscles. Likewise, the dorsiflexor represents all biological dorsiflexor muscles. In this work, joint and torque measurements were taken only at the ankle joint. As a result, the state of multi-articular muscles, such as the gastrocnemius, could not be accurately estimated. Therefore the plantar flexor was based upon the dominant monarticular plantar flexor in humans, the Soleus. Therefore, the majority of the plantar flexor parameters values are those reported in H. Geyer, H. Herr, "A muscle-reflex model that encodes principles of legged mechanics predicts human walking dynamics and muscle activities," (Submitted for publication) for the Soleus muscle. Some parameters of the plantar flexor, as well as those for the dorsiflexor, however, were expected to either have been significantly affected by the lumped models, or were not well known from biology. These six parameters were fitted using a combination of a Genetic Algorithm and gradient descent to enable the neuromuscular model to best match the walking data of an intact subject.

Non-Optimized Parameter Values are shown in Table 6.

TABLE 6

| | | | |
|---|---|---|---|
| $l_{opt}$ [m] | 0.04 | w | 0.56 |
| $l_{slack}$ [m] | 0.26 | c | ln(0.05) |
| $v_{max}$ [$l_{opt}$/s] | 6.0 | N | 1.5 |
| $\varepsilon_{ref}$ | 0.04 | K | 5 |
| PreA | 0.01 | $\rho$ | 0.5 |
| T [s] | 0.01 | $r_{foot}$ [m] | 0.05 |
| PreSTIM | 0.01 | $Delay_{RF}$ [s] | 0.02 |

Non-amputee Subject Data Collection. Kinetic and kinematic walking data were collected at the Gait Laboratory of Spaulding Rehabilitation Hospital, Harvard Medical School, in a study approved by the Spaulding committee on the Use of Humans as Experimental Subjects [H. Herr, M. Popovic, "Angular momentum in human walking," The Journal of Experimental Biology, Vol. 211, pp 487-481, 2008]. A healthy adult male (81.9 kg) was asked to walk at slow walking speed across a 10 m walkway in the motion capture laboratory after informed consent was given.

The motion-capture was performed using a VICON 512 motion-capture system with eight infrared cameras. Reflective markers were placed at 33 locations on the subject's body in order to allow the infrared cameras to track said locations during the trials. The cameras were operated at 120 Hz and were able to track a given marker to within approximately 1 mm. The markers were placed at the following bony landmarks for tracking the lower body: bilateral anterior superior iliac spines, posterior superior iliac spines, lateral femoral condyles, lateral malleoli, forefeet and heels. Wands were placed over the tibia and femur, and markers were attached to the wands over the mid-shaft of the tibia and the mid-femur. Markers were also placed on the upper body at the following sites: sternum, clavicle, C7 and T10 vertebrae, head, and bilaterally on the shoulder, elbow, and wrist joints.

Ground reaction forces were measured using two staggered force plates (model no. 2222 or OR6-5-1, by Advanced Mechanical Technology Inc., Watertown, Mass., USA) which were incorporated into the walkway. The precision of these force plates measuring ground reaction force and center of pressure is approximately 0.1 N and 2 mm respectively. The force plate data was collected at 1080 Hz and synchronized with the VICON motion capture data. Joint torques were calculated from the ground reaction forces and joint kinematics using a modified version of a standard inverse dynamics model. Vicon Bodybuilder, by Oxford Metrics, UK was used to perform the inverse dynamics calculations.

Six trials were obtained for a slow level-ground walking speed (1.0 m/s mean) and a single trial was used to represent the target ankle and torque trajectories for this walking condition. The end of the stance phase was defined as the point in time when the joint torque first dropped to zero after the peak torque was reached in the gait cycle. This event occurred at 67% gait-cycle for the selected trial.

Figure 16A:
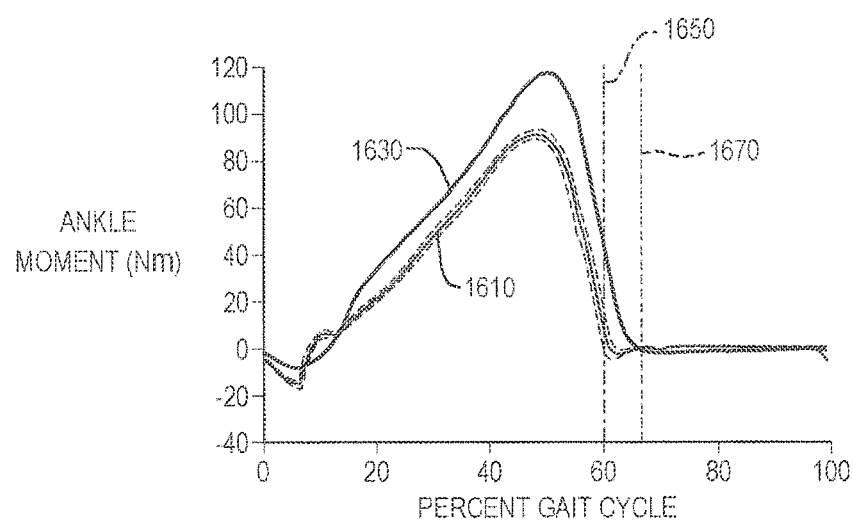
FIGS. 16A and 16B depict prosthesis-measured torque and angle trajectories during trials with an amputee subject compared to those of the biological ankle of a weight and height-matched subject with intact limbs, including ankle torque and ankle angle, respectively.
Figure 16B:
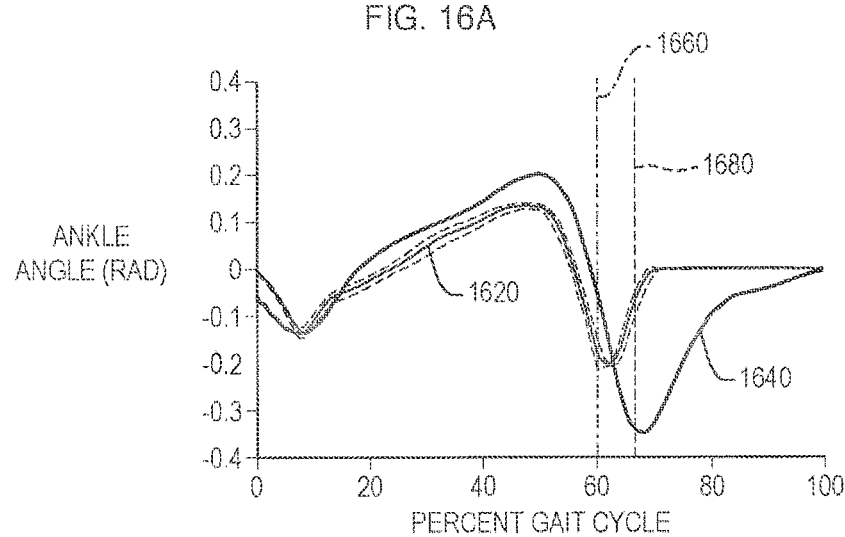

FIGS. 16A and 16B depict prosthesis-measured torque and angle trajectories during trials with an amputee subject compared to those of the biological ankle of a weight and height-matched subject with intact limbs. Shown in FIGS. 16A and 16B are ankle torque (FIG. 16A) and ankle angle (FIG. 16B) over a level-ground gait cycle from heel-strike (0% Cycle) to heel-strike of the same foot (100% Cycle). Plotted in FIGS. 16A and 16B are mean 1610, 1620 (thin line)±one standard deviation (dashed lines) for the prosthesis measured torque and angle profiles resulting from the neuromuscular-model control, and the ankle biomechanics 1630, 1640 (thick line) for a gait cycle of the weight and height-matched subject with intact limbs at the same walking speed (1 m/sec). Vertical lines indicate the average time of the beginning of swing phase 1650, 1660 (thin dash-dot line) for the prosthesis gait cycles and the beginning of the swing phase 1670, 1680 (thick dash-dot line) of the biological ankle.

Fitting of Model Parameters to Experimental Data via Optimization. The following parameters were chosen for tuning: $F_{max}$, $Gain_{FB}$, $Gain_{SUPP}$, $\phi_{ref}$ and $\phi_{max}$. The goal of the parameter tuning was to find the parameter set that would enable the neuromuscular model to best match a biological ankle torque trajectory for a particular walking condition, given the corresponding biological ankle angle trajectory as input to the model. The cost function for the optimization was defined as the squared error between the biologic and model torque profiles during the stance phase, given the biological ankle angle trajectory, i.e.:

$$\text{Cost} = \sum_{t \in STANCE} (T_m(t) - T_{bio}(t))^2. \tag{14}$$

where $T_m$ is the torque output of the model, and $T_{bio}$ is the biological ankle torque.

A Genetic Algorithm optimization was chosen to perform the initial search for optimal parameter values, and a direct search was included to pinpoint the optimal parameter set. The Genetic-Algorithm tool in Matlab was used to implement both optimization methods. The level-ground human walking data at the selected 1.0 m/s walking speed was used to provide the reference behavior for the optimization. The allowable range for each of the optimization parameters are shown in Table 7.

TABLE 7

Optimization Parameter Ranges

| Parameter (Units) | Minimum Value | Maximum Value |
|---|---|---|
| $F_{max}$ (N) | 3000 | 7000 |
| $Gain_{FB}$ | 0.6 | 1.5 |
| $K_P$ (N · m/rad) | 20 | 250 |
| $Gain_{SUPP}$ | 0 | 5 |
| $\phi_{ref}$ (rad) | 0.52 | 2.09 |
| $\phi_{max}$ (rad) | 1.40 | 2.44 |

The initial population was chosen by the optimizer. The parameter values obtained from the parameter optimization are shown in Table 8.

TABLE 8

Fitted Values of Neuromuscular Model Parameters

| $F_{max}$ (N) | 3377 |
|---|---|
| $Gain_{FB}$ | 1.22 |
| $K_P$ (N · m/rad) | 72.9 |
| $Gain_{SUPP}$ | 0 |
| $\phi_{ref}$ (rad) | 1.49 |
| $\phi_{max}$ (rad) | 1.95 |

Results of the parameter optimization. As a verification of the optimization effectiveness, the optimization was run with the final parameters using the biological ankle angle profile as input to the neuromuscular model. A comparison of the resulting torque profile to the biologic torque profile is shown in FIG. 17.

Figure 17:
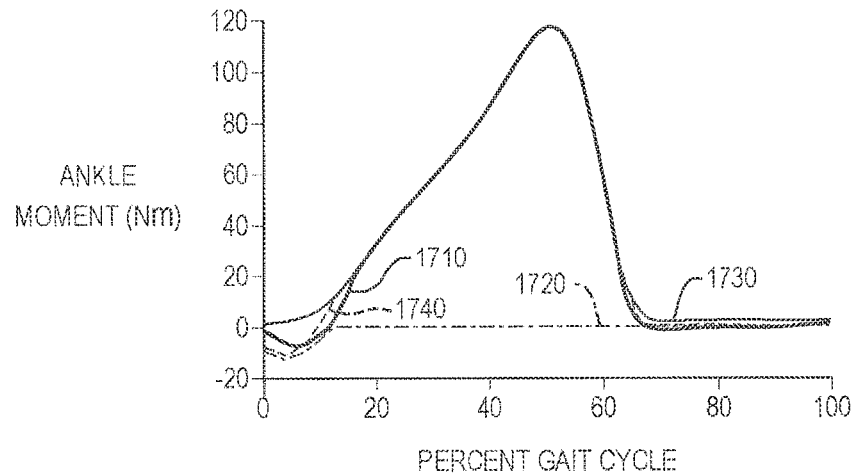
FIG. 17 is a comparison of the torque profile after parameter optimization to the biologic torque profile, according to one aspect of the present invention.

As shown in FIG. 17, a comparison of the ankle moment profile from the intact biological ankle to that of the neuromuscular model with the biological ankle angle profile as the input and with optimized parameter values, are biological ankle moment (grey line) 1710, modeled dorsiflexor component (dash-dot line) 1720, modeled plantar flexor muscle component (thin line) 1730, and total neuromuscular model (plantar flexor and dorsiflexor) moment (dashed line) 1740. The neuromuscular model ankle moment matches the biological ankle moment almost exactly for most of the gait cycle.

Low-Level Torque Control. The physical torque actually produced at the ankle joint during stance phase is from the combined actions of the parallel spring and the motorized drive train. The rotary parallel spring stiffness is approximately linear in the range of operation, with a spring stiffness of 500 N·m/rad. Using this spring constant, the parallel spring contribution is predicted and subtracted from the desired ankle torque. The remaining torque must be produced by the motorized drive train.

The performance of the motorized drive train is improved by use of lead compensation, friction compensation and feed-forward techniques, as shown in FIG. 12. Experimental investigations of the open loop drive train dynamics were performed and used to implement these improvements [M. Eilenberg, "A Neuromuscular-Model Based Control Strategy for Powered Ankle-Foot Prostheses," Master's Thesis, Massachusetts Institute of Technology, Cambridge, Mass., 2009]. The output torque versus commanded torque for level-ground walking, ramp ascent, and ramp descent is shown in FIGS. 13A-C. The prosthesis output torque was estimated using the strain gauge on the series spring for the SEA torque contribution, and the ankle angle-based parallel spring torque estimate for the parallel spring torque contribution.

Clinical Evaluation. The prosthesis was placed on the right leg of a healthy, active, 75 kg transtibial amputee. The subject was allowed time to walk on the prosthesis for natural adjustment. The wireless link to the prosthesis was used to record the walking data from these trials. During the level-ground walking trials, the subject was asked to walk across a 10 m long path. The target intended walking speed was set to 1.0 m/s to match that of the intact subject. The subject began walking approximately 5 m from the beginning of the pathway, and stopped walking approximately 3 m past the end of the path. Markers on the ground were used to note the beginning and end of the 10 m path. A stopwatch was used to verify the average walking speed for each trial by noting when the subject's center of mass passed over each of the markers. A total of 10 trials were captured. Trials with walking speeds within 5% of the target speeds were used for processing, resulting in 45 gait cycles. The subject was next asked to walk up an 11-degree, 2 m long incline at a self-selected speed. The subject started on level-ground approximately 2 m from the start of the incline and stopped approximately 1 m past the incline on a platform for 10 ramp-ascent trials. This same path was then navigated in reverse for 12 ramp-descent trials.

Data Analysis. The first three and last three gait cycles of the level-ground trials were assumed to be transients, and were therefore ignored. Each of the remaining gait cycles were re-sampled to span 1000 data points. Mean and standard-deviation trajectories were computed from the resulting data. For both ramp ascent and descent, the last step on the ramp was used as the representative gait cycle. Each selected gait cycle was re-sampled and averaged in the same manner as described for the level-ground trials.

The net work was calculated for each individual gait cycle by numerically integrating ankle torque over ankle angle from heel-strike to toe-off. Here the swing phase was ignored for the net work calculations. The average net work for each walking condition was then computed from the individual gait cycle net work values.

Results. Torque Tracking. A precondition of the present experiments was the ability of the ankle-foot prosthesis to actually produce the torques and speeds that would be commanded by the neuromuscular controller. This ability is demonstrated in FIGS. 13A-C, illustrating commanded torque versus measured output torque for level-ground walking, ramp ascent, and ramp descent.

Adaptation to Ground Slope. The evaluation of ground slope adaptation of the neuromuscular-model controlled prosthesis was confirmed by the clinical trial data of FIGS. 9a-9c. The numerically integrated data of those trials gave net work values (work loop areas) as follows:

| Level-Ground | 5.4 ± 0.5 | Joules |
| Ramp Ascent | 12.5 ± 0.6 | Joules |
| Ramp Descent | 0.1 ± 1.7 | Joules |

Comparison to a Biological Ankle. The purpose of this neuromuscular model is to represent the inherent dynamics of the human ankle-foot complex in a useful way. Therefore, one may evaluate the resulting prosthesis controller based upon its ability to mimic the human behavior. FIGS. 16A and 16B, discussed previously, show the level-ground walking torque and angle profiles from the prosthesis along with those of a weight and height-matched subject with intact limbs.

Figure 18A:
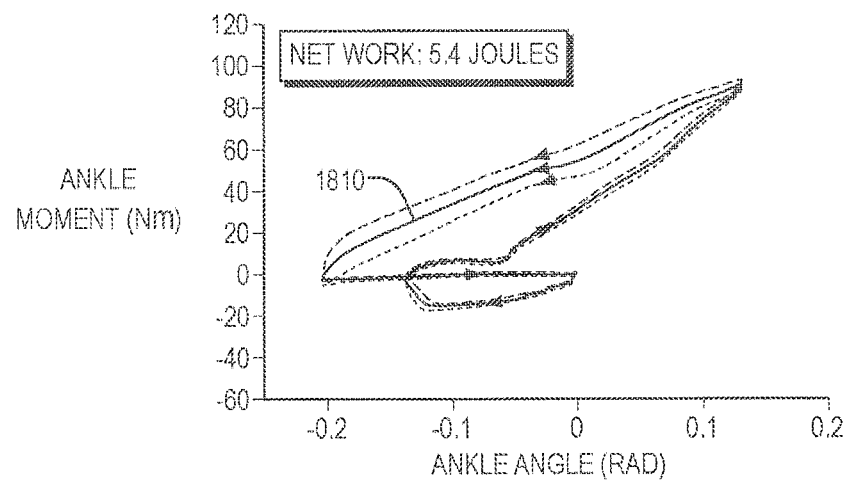
FIGS. 18A-C are plots of experimentally measured prosthesis torque-angle trajectories for an exemplary embodiment of the invention for three different walking conditions: level ground (FIG. 18A), ramp ascent (FIG. 18B), and ramp descent (FIG. 18C)
Figure 18B:
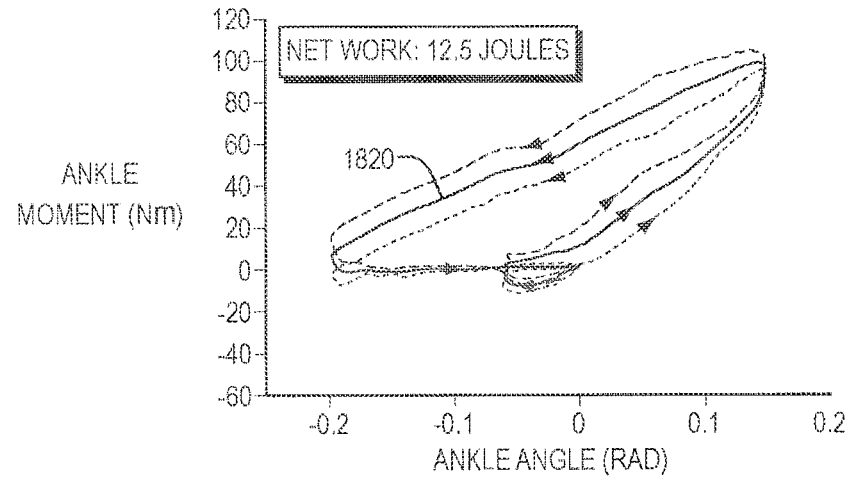
Figure 18C:
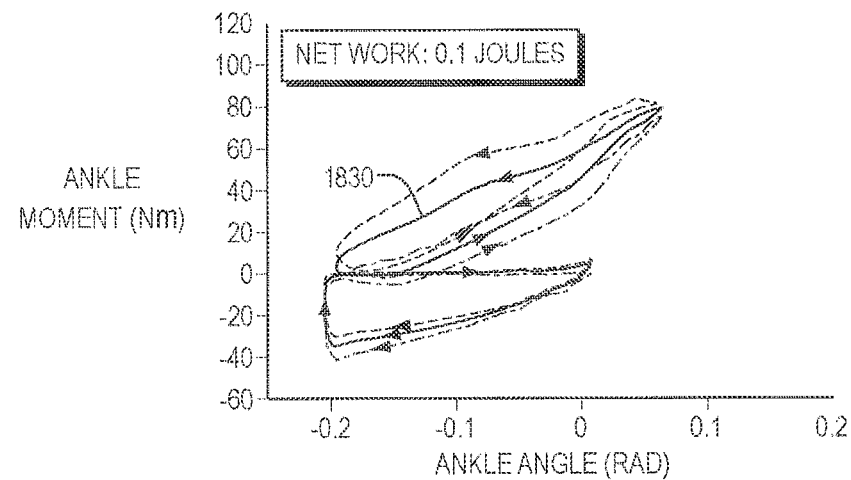

FIGS. 18A-C are plots of measured prosthesis torque-angle trajectories for three different walking conditions: level ground (FIG. 18A), ramp ascent (FIG. 18B), and ramp descent (FIG. 18C). Shown in FIGS. 18A-C, are mean 1810, 1820, 1830±one standard deviation. Arrows indicate forward propagation in time. The average prosthesis net work increases with increasing ground slope. This result is consistent with human ankle data from the literature [A. S. McIntosh, K. T. Beatty, L. N. Dwan, and D. R. Vickers, "Gait dynamics on an inclined walkway," Journal of Biomechanics, Vol. 39, pp 2491-2502, 2006].

The measured ankle torque and ankle angle profiles of the prosthesis qualitatively match those of a comparable intact individual for level-ground walking. The differences observed are of a low order, and may reasonably be attributed to a number of factors, including atrophy and/or hypertrophy in the clinical subject's leg muscles resulting from amputation, differences in limb lengths, and perhaps the lack of a functional biarticular gastrocnemius muscle. In addition, the limited range of the prosthetic angle sensor prohibited the prosthesis from reaching the full range of motion of the intact ankle.

Ground Slope Adaptation. The neuromuscular control presented here exhibits an inherent adaptation to ground slope without explicit sensing of terrain. The increased ankle net work during ramp ascent, and the decreased ankle net work during ramp descent, as compared to that of level ground walking, is consistent with the behavior of an intact human ankle under the same conditions, according to data from [A. S. McIntosh, K. T. Beatty, L. N. Dwan, and D. R. Vickers, "Gait dynamics on an inclined walkway," Journal of Biomechanics, Vol. 39, pp 2491-2502, 2006]. This variation of stance-phase positive net work across walking conditions indicates a slope-adaptive behavior that is emergent of the neuromuscular model. The ability of the neuromuscular model to produce these biomimetic changes in behavior suggests that the model embodies an important characteristic of the human plantar flexor muscles. In addition, it is anticipated that the model has the potential for speed adaptation. In an attempt to move faster, the wearer may push harder on the prosthesis. This additional force could cause the modeled reflex to command higher virtual muscle forces, resulting in greater energy output, and hence higher walking speeds.

Artificial Joints Using Agonist-Antagonist Actuators

In the construction of a biologically realistic limb system that is high performance, light weight, quiet and power efficient, an agonist-antagonist actuator design is proposed herein comprising a plurality of actuators and series elastic structures. Since it is desirable to minimize the overall weight of the limb design, the efficiency of the agonist-antagonist actuator design is critical, especially given the poor energy density of current power supplies, e.g. lithium-ion battery technology. By understanding human biomechanics, the lightest, most energy efficient agonist-antagonist actuator design can be achieved.

In the next section, the key features of biomechanical systems are highlighted. A more complete description of biomechanical systems is found in the patent applications cited in the foregoing "Cross Reference to Related Applications" whose disclosures are incorporated herein by reference.

Joint Biomechanics: The Human Ankle

Understanding normal walking biomechanics provides the basis for the design and development of the agonist-antagonist actuator design. Specifically, the function of human ankle under sagittal plane rotation is described for different locomotor conditions including level-ground walking and stair/slope ascent and descent. In addition, the function of the human knee during level ground walking is described. From these biomechanical descriptions, the justifications for key mechanical components and configurations of the actuator invention are established.

Level-Ground Walking

Figure 19:
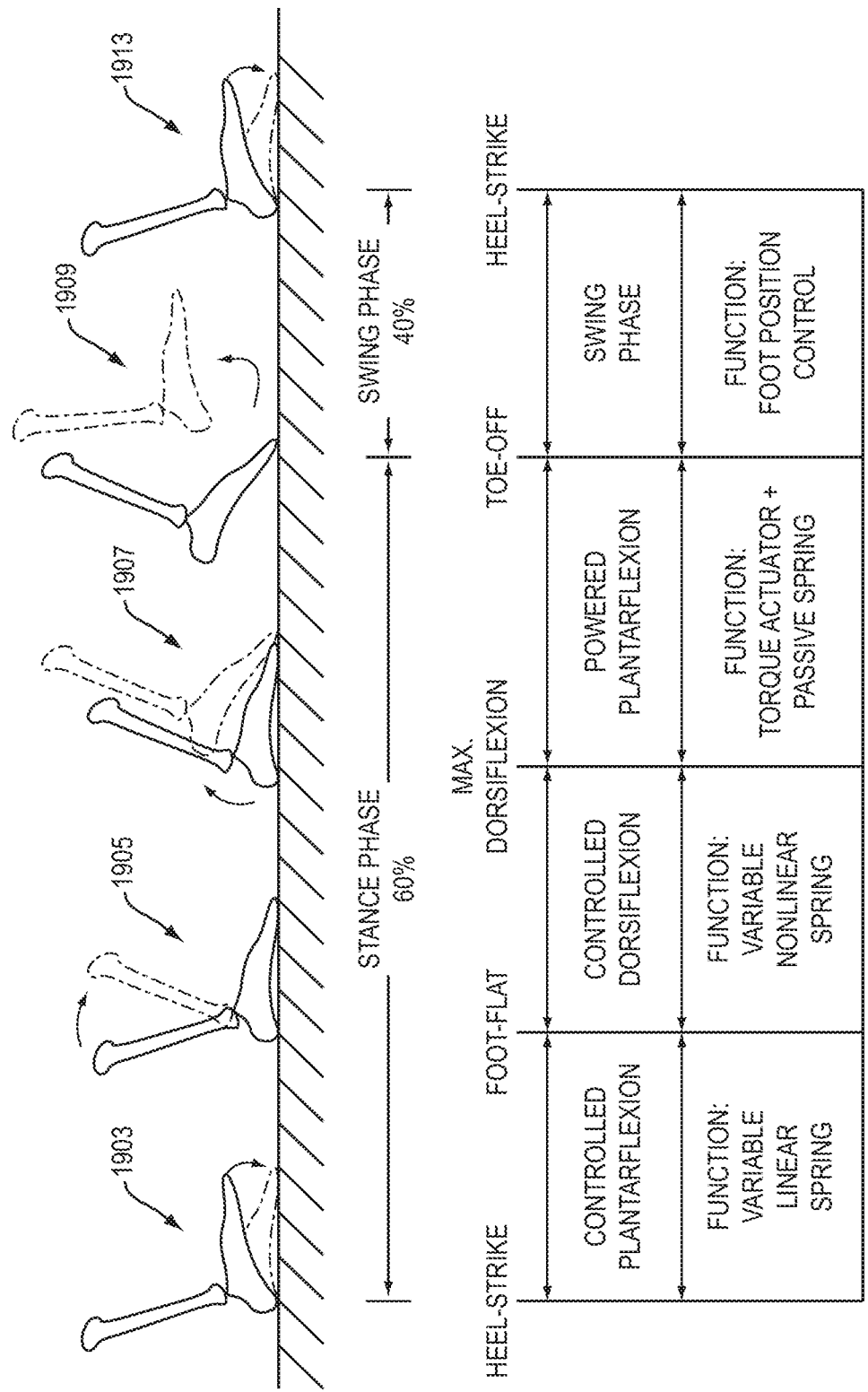
FIG. 19 depicts the various subdivisions of the stance phase of walking.

A level-ground walking gait cycle is typically defined as beginning with the heel strike of one foot seen at 1903 in FIG. 19 and ending at the next heel strike of the same foot seen at 1913. See {8}. The main subdivisions of the gait cycle are the stance phase (~60%) and the swing phase (~40%) which are illustrated in FIG. 19. The swing phase represents the portion of the gait cycle when the foot is off the ground. The stance phase begins at heel strike when the heel touches the floor and ends at toe off when the same foot rises from the ground surface. Additionally, we can further divide the stance phase into three sub-phases: Controlled Plantar Flexion (CP), Controlled Dorsiflexion (CD), and Powered Plantar Flexion (PP).

Detailed descriptions for each phase and the corresponding ankle functions are described in FIG. 19. CP begins at heel-strike 1903 and ends at foot-flat shown at 1905. Simply speaking, CP describes the process by which the heel and forefoot initially make contact with the ground. In {1} and {3}, researchers showed that CP ankle joint behavior is consistent with a linear spring being loaded or stretched where joint torque is proportional to joint position.

During the loading process, the spring behavior is, however, variable; joint stiffness is continuously modulated by the body from step to step. After the CP period, the CD phase begins. In FIG. 20, the average torque versus angle curves are shown for 68 healthy, young participants walking on a level surface. As is shown, during CP (from 1903 to 1905), the ankle behaves as a linear spring of variable stiffness during the loading cycle, but the torque curve does not trace back to point 1, but rather assumes higher torque values during the early period of CD.

Ankle torque versus position during the CD period from 1905 to 1907 can often be described as a nonlinear spring being loaded or stretched where stiffness increases with increasing ankle position. It is noted that as walking speed increases, the extent to which the ankle behaves as a nonlinear spring increases, with the CD loading phase exhibiting distinct nonlinear behavior during fast walking (see fast walking, FIG. 20C). The main function of the ankle during CD is to store elastic energy to propel the body upwards and forwards during the PP phase. See {9} and {3}.

The PP phase begins at 1907 after CD and ends at the instant of toe-off shown at 1909. During PP in moderate to fast walking speeds, the ankle can be modeled as a catapult in series or in parallel with the CD spring or springs. Here the catapult component includes an actuator that does work on a series spring during the CD phase and/or during the first half of the PP phase. The catapult energy is then released along with the spring energy stored during the CD phase to achieve the high plantar flexion power during late stance. This catapult behavior is necessary because the work generated during PP is more than the negative work absorbed during the CP and CD phases for moderate to fast walking speeds as clearly seen in FIGS. 20A-20C. See {1}, {2}, {3} and {9}.

Figure 20A:
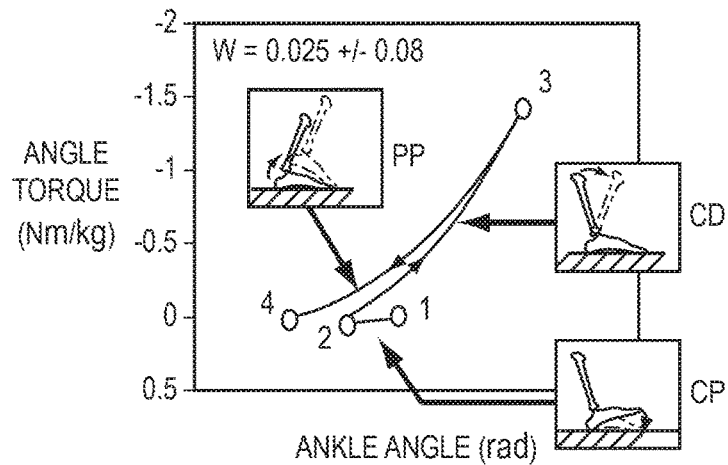
FIGS. 20A, 20B and 20C show torque vs. angle plots in level-ground walking for slow speed, normal and fast walking.
Figure 20B:
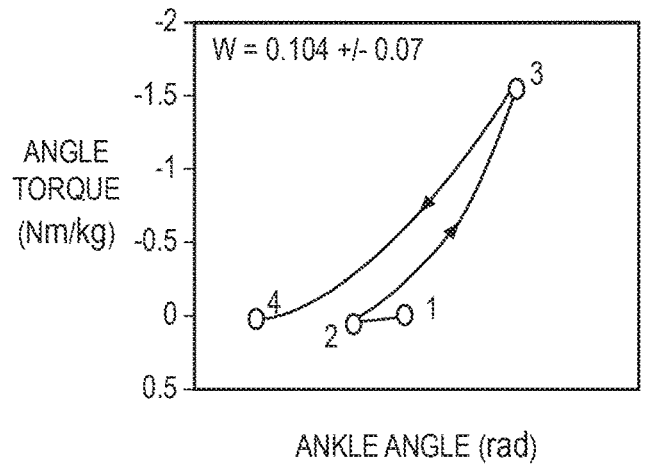
Figure 20C:
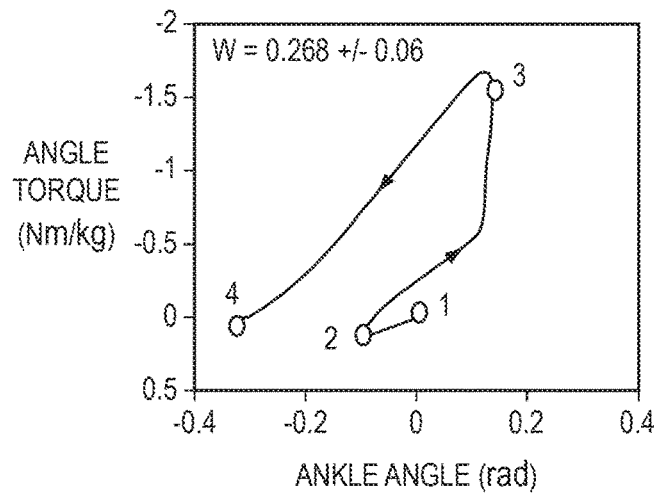

FIGS. 20A, 20B and 20C show torque vs. angle plots in level-ground walking for slow speed walking at 0.9 m/sec (FIG. 20A), normal walking speed at 1.25 m/sec (FIG. 20B) and fast walking at 1.79 m/sec. Only the stance period of a single foot is shown (heel strike to toe off). Point 1 on the charts denotes heel strike, point 2 foot flat, point 3 peak dorsiflexion, and point 4 toe off. Although during slow walking the loading curve (points 2-3) is approximately equal to the unloading curve (points 3-4), for higher walking speeds the torque assumes higher values during the unloading, PP phase (points 3-4). Hence, for walking speeds greater than 0.9 m/s (slow speed), the human ankle cannot be modeled as a series of coupled springs because the positive work performed by the ankle exceeds the negative work. It is noted that, as walking speed increases, the degree of nonlinear behavior during CD (points 2-3) increases along with the total amount of positive work production during PP (points 3-4), consistent with a catapult model where the soleus muscle belly slowly elongates the series Achilles tendon spring during CD, increasing the slope of the torque versus angle curve and the subsequent positive power output of the ankle.

Stair Ascent and Descent

Figure 21:
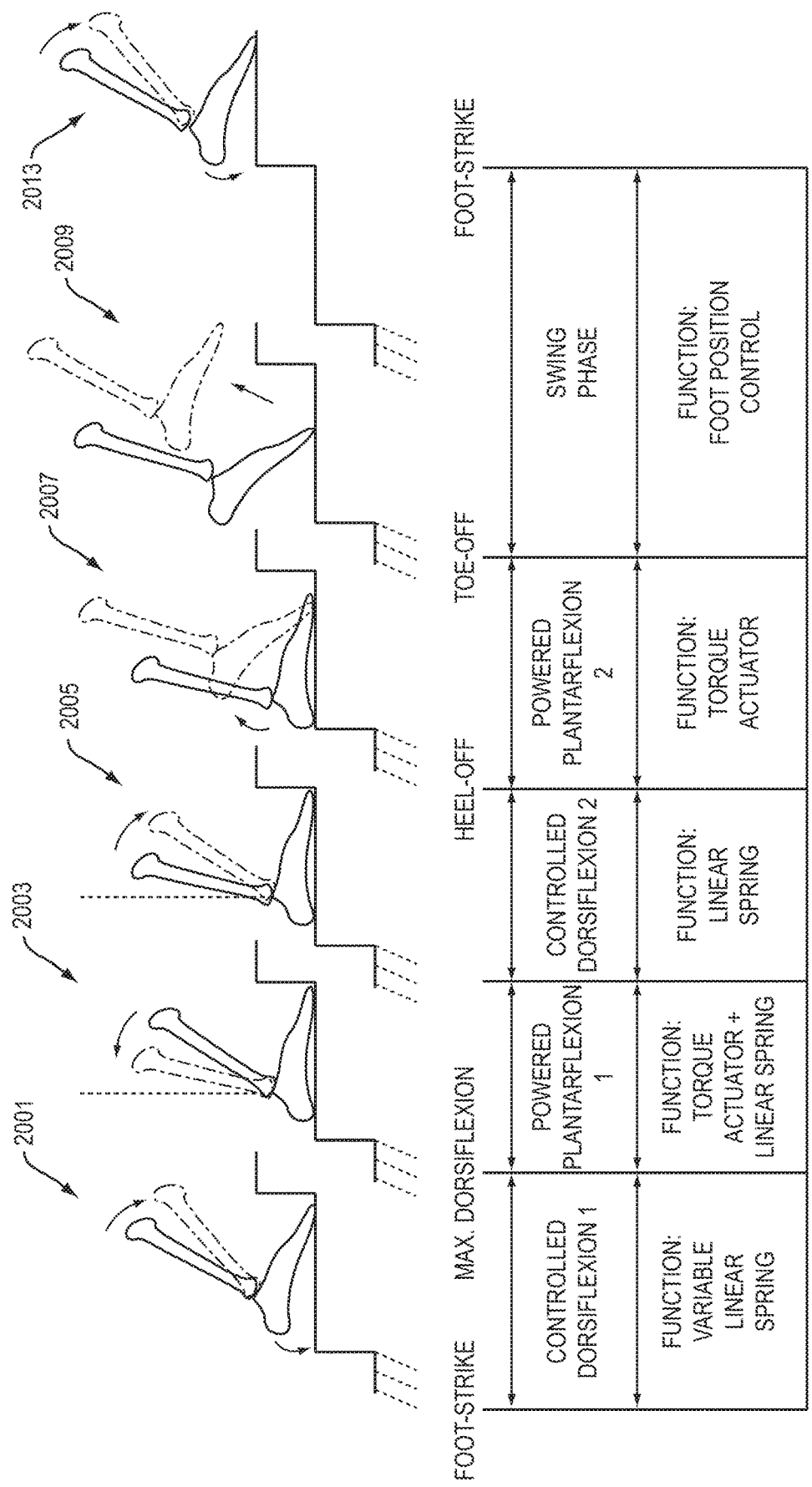
FIG. 21 illustrates human ankle biomechanics for stair ascent.

FIG. 21 illustrates human ankle biomechanics for stair ascent; The first phase of stair ascent is called Controlled Dorsiflexion 1 (CD 1), which begins with foot strike in a dorsiflexed position at 2001 and continues to dorsiflex until the heel contacts the step surface at 2003. In this phase, the ankle can be modeled as a linear spring. The second phase is Powered Plantar flexion 1 (PP 1), which begins at the instant of foot flat (when the ankle reaches its maximum dorsiflexion) at 2003 and ends when dorsiflexion begins once again at 2005. The human ankle behaves as a torque actuator to provide extra energy to support the body weight. The third phase is Controlled Dorsiflexion 2 (CD 2), in which the ankle dorsiflexes as seen at 2005 until heel-off at 2007. For that phase, the ankle can be modeled as a linear spring. The fourth and final phase is Powered Plantar flexion 2 (PP 2). Here the foot pushes off the step as seen at 2007, acting as a torque actuator in parallel with the CD 2 spring to propel the body upwards and forwards until toe-off occurs at 2009 and the swing phase begins.

Figure 22:
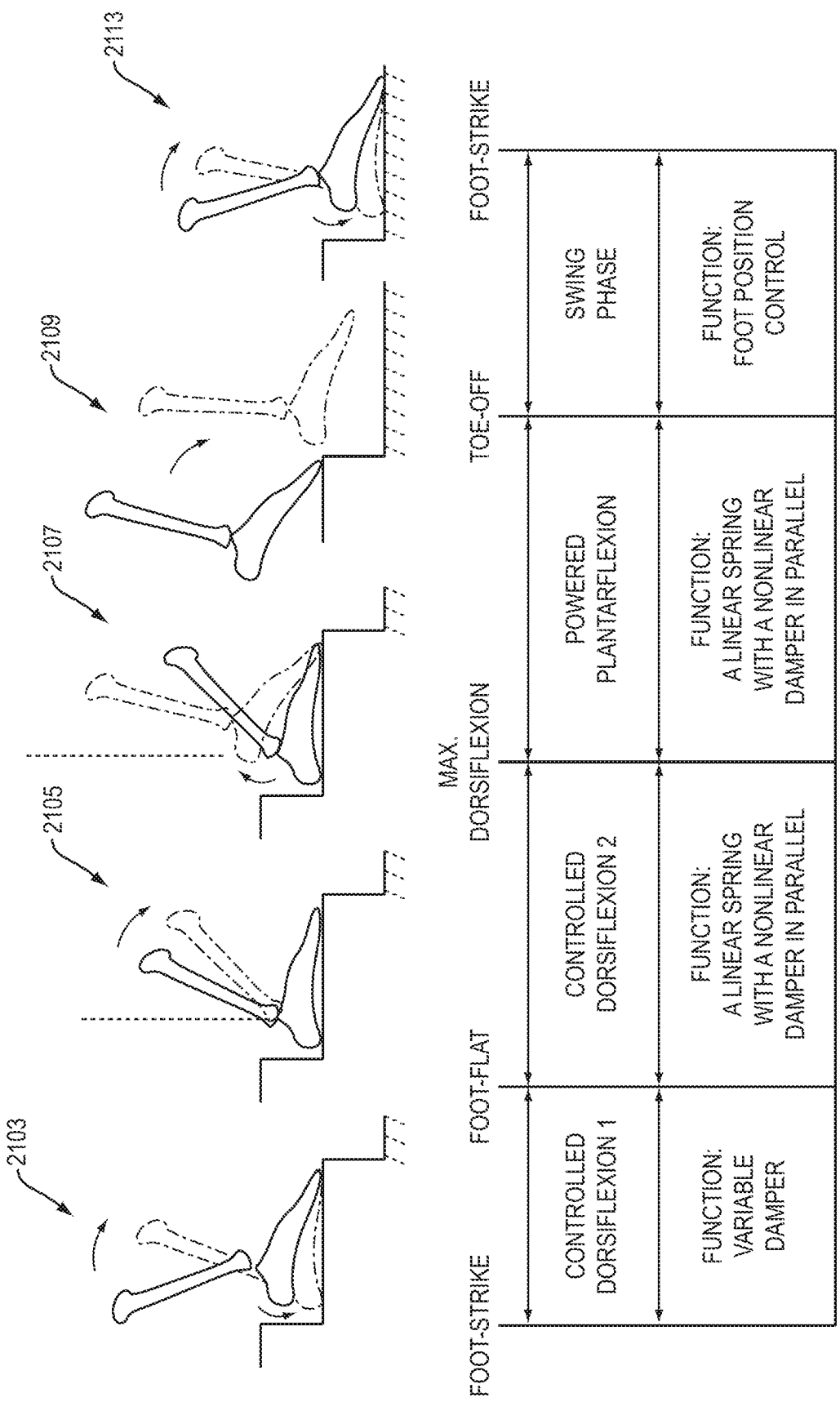
FIG. 22 illustrates human ankle-foot biomechanics for stair descent.

FIG. 22 illustrates the human ankle-foot biomechanics for stair descent. The stance phase of stair descent is divided into three sub-phases: Controlled Dorsiflexion 1 (CDI), Controlled Dorsiflexion 2 (CD2), and Powered Plantar flexion (PP). CDI begins at forefoot strike seen at 2103 and ends at foot-flat seen at 2105. In this phase, the human ankle can be modeled as a variable damper. In CD2, from foot flat at 2105, the ankle continues to dorsiflex forward until it reaches a maximum dorsiflexion posture at 2107. Here the ankle acts as a linear spring in series with a variable-damper designed to effectively control the amount of energy stored by the linear spring. During PP, beginning at 2107, the ankle plantar flexes until the foot lifts from the step at 2109. In this final phase, the ankle releases stored CD2 energy, propelling the body upwards and forwards. From toe off at 2109 until the next foot strike at 2113, the foot in the swing phase.

Because the kinematic and kinetic patterns at the ankle during stair ascent/descent are significantly different from that of level-ground walking (see {2}), a description of such ankle-foot biomechanics seems appropriate. For stair ascent, the human ankle-foot can be effectively modeled using a combination of an actuator and a variable stiffness mechanism. However, for stair descent, variable damping needs also to be included for modeling the ankle-foot complex; the power absorbed by the human ankle is much greater during stair descent than the power released by 2.3 to 11.2 J/kg. See reference {2}.

Joint Biomechanics: The Human Knee

Figure 23A:
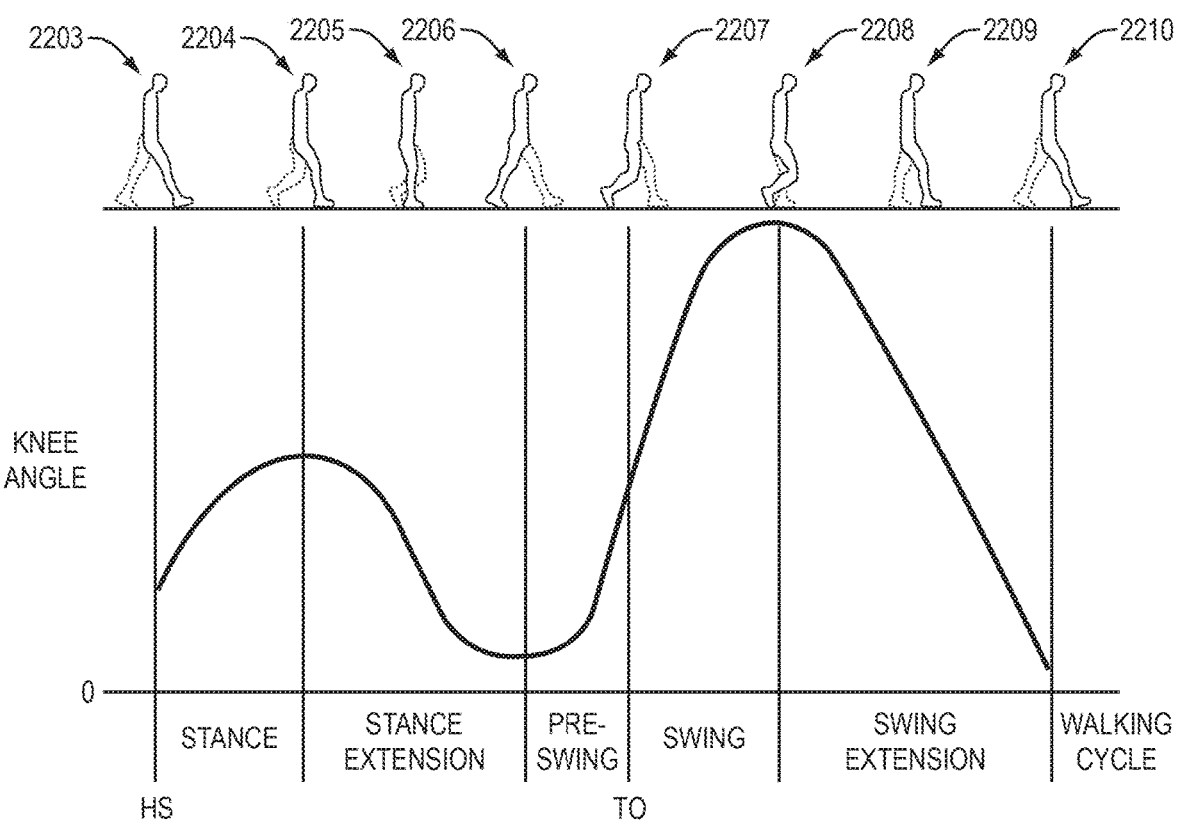
FIGS. 23A and 23B illustrate the manner in which knee angle and knee power respectively vary during the walking cycle for level ground walking.
Figure 23B:
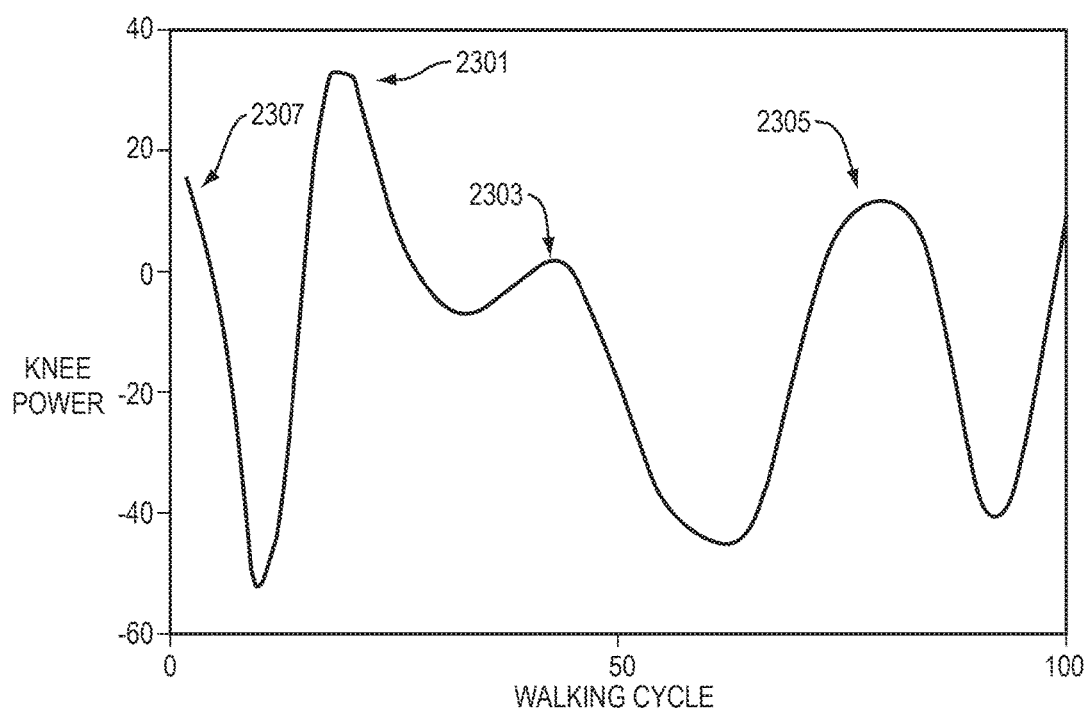

There are five distinct phases to knee operation throughout a level-ground walking cycle as illustrated in FIGS. 23A and 23B. See reference {8}. FIG. 23A shows how the knee angle varies during the walking cycle, and FIG. 23B shows how knee power varies. As seen in FIG. 23A, the stance phase of walking can be divided into three subphases: Stance Flexion, Stance Extension, and Pre-Swing. The swing phase is divided into two phases: Swing Flexion and Swing Extension. As seen in FIG. 23B, for level ground walking, the human knee does more negative work than positive work.

Beginning at heel strike indicated at 2203, the stance knee begins to flex slightly. This flexion period, called the Stance Flexion phase, allows for shock absorption upon impact as well as to keep the body's center of mass at a more constant vertical level throughout the stance period. During this phase, the knee acts as a spring, storing energy in preparation for the Stance Extension phase.

After maximum flexion is reached in the stance knee at 2204, the joint begins to extend, until maximum extension is reached as indicated at 2206. This knee extension period is called the Stance Extension phase. Throughout the first ~60% of Stance Extension, the knee acts as a spring, releasing the stored energy from the Stance Flexion phase of gait. This first release of energy corresponds to power output indicated at 2301 in the graph at the bottom of FIG. 23B. During the last ~30% of Stance Extension, the knee absorbs energy in a second spring and then that energy is released during the next gait phase, or Pre-Swing.

During late stance or Pre-Swing from 2206 to 2207, the knee of the supporting leg begins its rapid flexion period in preparation for the swing phase. During early Pre-Swing, as the knee begins to flex in preparation for toe-off, the stored elastic energy from Stance Extension is released. This second release of energy corresponds to power output seen at 2303 in FIG. 23B.

As the hip is flexed, and the knee has reached a certain angle in Pre-Swing, the leg leaves the ground at 2207 and the knee continues to flex. At toe-off 2207, the Swing Flexion phase of gait begins. Throughout this period, knee power is generally negative where the knee's torque impedes knee rotational velocity. During terminal Swing Flexion, the knee can be modeled as an extension spring in series with a variable damper, storing a small amount of energy in preparation for early Swing Extension.

After reaching a maximum flexion angle during swing at 2208, the knee begins to extend forward. During the early Swing Extension period, the spring energy stored during late Swing Flexion is then released, resulting in power output seen at 2305 in FIG. 23B. During the remainder of Swing Extension, the human knee outputs negative power (absorbing energy) to decelerate the swinging leg in preparation for the next stance period. During terminal Swing Extension, the knee can be modeled as a flexion spring in series with a variable damper, storing a small amount of energy in preparation for early stance (at 2307). After the knee has reached full extension, the foot once again is placed on the ground, and the next walking cycle begins.

An agonist-antagonist actuator described below implements these muscle-like actuation properties. The actuator comprises a plurality of springs, mechanical transmissions, and active elements where each spring is in series with an active element via a transmission, and each spring-transmission-active element combination are in parallel and capable of opposing one another in an agonist-antagonist manner. The components of the agonist-antagonist actuator are listed in Table 9 with their functional purposes outlined.

The Agonist-Antagonist Actuator: An Example

Figure 24A:
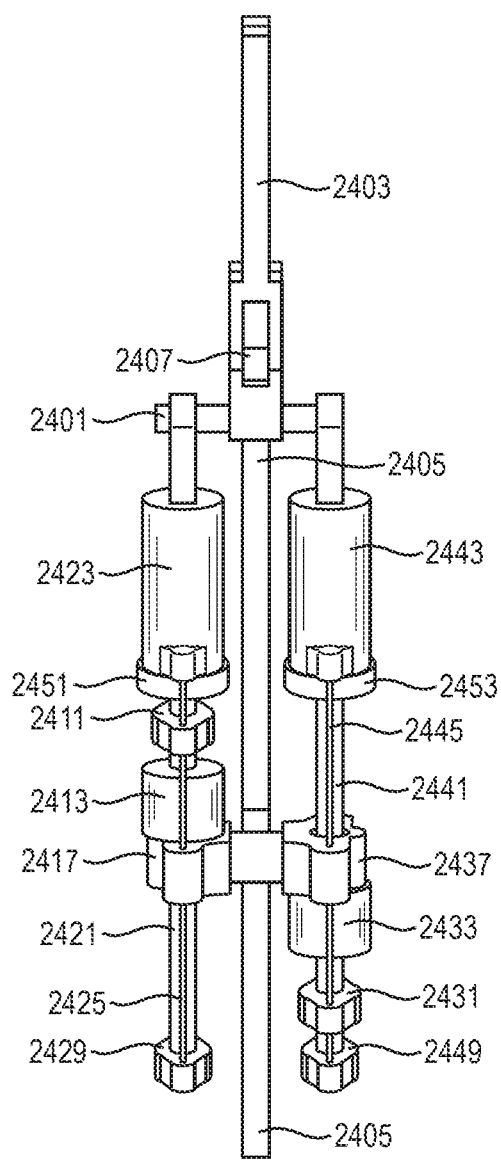
FIGS. 24A and 24B are posterior and side elevational views respectively of an agonist-antagonist actuator embodying the invention.
Figure 24B:
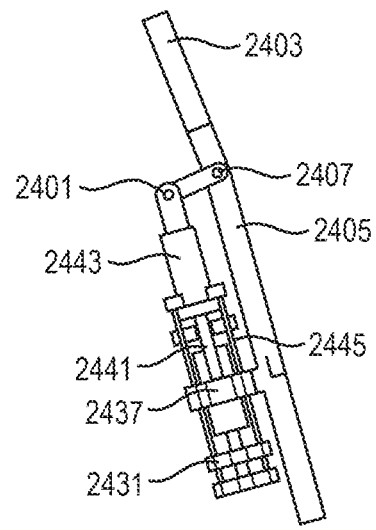

In FIGS. 24A-B, one implementation of the actuator is shown as an example. For this particular actuator form, the active element comprises a motor in parallel with a variable damper. The flexion and extension motors can control the position of flexion and extension nuts, respectively, via ball screw mechanical transmissions. As seen in FIG. 24A, two side-by-side actuators are attached at their upper ends to a cross-rod 2401 which provides a connection point to the upper link 2403 of the joint mechanism. The upper link 2403 is connected to the lower link 2405 at a joint 2407.

The actuator that extends along the left-hand side of the upper and lower links 2403 and 2405 as seen in FIG. 24A includes an extension nut 2411 that engages with and compresses an extension spring 2413. The extension spring 2413 is positioned between the extension nut 2411 and a linear bearing 2417 which is attached to the lower link 2405. An extension ballscrew seen at 2421 connected via a gearbox (not shown) to the armature of an extension motor 2423. An extension nut guidance shaft 2425 is attached to the case of the motor 2423 and extends downwardly from the motor 2423 through the extension nut 2411 and the linear bearing 2417 to a shaft endcap 2429. The guidance shaft 2425 prevents the extension nut from rotating so that, as the extension motor 2423 rotates the extension ballscrew 2421, the extension nut 2411 moves longitudinally with respect to the cross-rod 2401 and the motor 2423, varying the joint angle at which the extension nut engages with the extension spring 2413. Thus, the extension motor 2423 can compress the extension spring 2413 as the extension nut 2411 is driven downward to increase the length of the actuator and extend (increase) the joint angle.

The actuator that extends along the right-hand side of the upper and lower links 2403 and 2405 as seen in FIG. 24A includes a flexion nut 2431 that engages with and compresses a flexion spring 2433. The flexion spring 2433 is positioned between the flexion nut 2431 and a linear bearing 2437 which is attached to the lower link 2405. A flexion ballscrew seen at 2441 connected via a gearbox (not shown) to the armature of a flexion motor 2443. A flexion nut guidance shaft 2445 is attached to the case of the flexion motor 2443 and extends downwardly from the motor 2443 through the linear bearing 2437 and the flexion nut 2431 and the to a flexion shaft endcap 2449. The flexion nut guidance shaft 2445 prevents the extension nut from rotating so that, as the flexion motor 2443 rotates the flexion ballscrew 2441, the flexion nut 2431 moves longitudinally with respect to the cross-rod 2401 and the flexion motor 2443, varying the joint angle at which the flexion nut engages with the flexion spring 2433. Thus, the flexion motor 2423 can compress the flexion spring 2433 as the flexion nut 2431 is driven upwardly to decrease the length of the actuator and decrease the joint angle during flexion.

A variable damper is connected in parallel with each of the motors. An extension variable damper seen at 2451 is connected in parallel with the extension motor 2423 and a flexion variable damper seen at 2453 is connected in parallel with the flexion motor 2443.

Through the independent control of flexion and extension nut positions, the actuator length at which the flexion and extension springs are engaged can be independently controlled (Muscle-Like Property 3). Furthermore, the flexion and extension motors can compress each series spring simultaneously without the joint rotating where each spring exerts an equal but oppositely opposed force.

If the series springs are hardening springs where spring stiffness increases with increasing compression, joint stiffness can be effectively controlled through this agonist-antagonist motor action (Muscle-like property 4). After the motors co-contract and compress the flexion and extension springs to a desired spring deflection and a desired actuator stiffness, to maintain that stiffness, the variable dampers can output high damping levels to impede ballscrew rotation at low power requirements.

Since each motor is in parallel with each variable damper, both motors can be turned off while still maintaining spring deflection and overall actuator stiffness (Muscle-Like Property 2). The actuator can also dissipate mechanical energy at low power (Muscle-Like Property 2).

In the actuator form of FIG. 24A, the ballscrew transmissions are backdrivable. Hence, when an external agent compresses or lengthens the actuator, energy can be dissipated using the variable dampers. Since each variable damper is in parallel with each motor, during such a dissipative action, the motors can act as generators to store electrical power for later use. Finally, zero actuator force can be achieved at zero power consumption (Muscle-Like Property 1). If the motors move the ballscrew nuts away from their respective spring element, the actuator will output zero force and no energy is required to maintain that force.

Component Implementations

Active Element. Depending on the application, each active element could be either a motor or a variable damper/clutch, or a combination of these elements. If the active element includes a variable damper/clutch, it could be implemented using hydraulic, pneumatic, friction, electrorheological, magnetorhelogical, hysteresis brake, or magnetic particle brake damping/clutching strategies. The preferred mechanism for damping control is a hysteresis brake because the zero power damping level is negligible. This feature is important because the variable damper is behind the mechanical transmission where any strain rate dependent, low-end viscous or frictional effect would likely be amplified.

If the active element includes a motor, it could be any electric motor, brushed or brushless. It could also be a hydraulic or pneumatic cylinder or other mechanical power-producing elements such as artificial muscle, piezoelectrics or nitinol wire.

Spring. The springs could be implemented as linear or torsional spring elements. They may be metal die springs, carbon fiber leaf springs, elastomeric compression springs, or pneumatic springs. For the preferred implementations described in this specification, the springs are die compression springs.

Mechanical Transmission. The mechanical transmissions could be implemented as linear or torsional transmission elements. They could be harmonic drives, ballscrew drives, leadscrew drives, or any other mechanical transmission known in the art. For the case where the active element and the series spring are both linear or both rotary elements, and no gear reduction is deemed necessary, the transmission would simply be a material linkage, connecting spring to active element. For example, if the active element is a linear artificial muscle, and the spring a linear, elastomeric element, then the spring would simply be attached directly to the artificial muscle. For the preferred embodiments described in FIGS. 24-28, the mechanical transmissions are ballscrew transmissions.

TABLE 9

Mechanical components of the Agonist-Antagonist Actuator System

| Component | Function |
|---|---|
| Spring | Store and release energy, absorb shock, provide stiffness |
| Active Element | Control positive and negative work and power, control effective spring equilibrium length and stiffness, generate electrical power, clutch to engage series elasticity |
| Mechanical Transmission | Couple spring to active element, offer gear reduction between active element and output, convert rotary active element to linear spring element |

Sensing Implementations

For the Agonist-antagonist actuator to function properly, there are various sensors required to measure the state of the various actuator components. The sensors required to enable general actuator operation and control are:

1) Position sensors located at the biomimetic joint axis to measure joint angle (a rotary potentiometer), and at the active element (motor/variable damper/clutch) rotor to measure total displacement of the element's drive shaft and additionally the active element's velocity (a shaft encoder).

2) A force sensor (strain gauges) to measure the actual torque borne by the joint.

3) A displacement sensor on each spring in order to measure the amount of energy stored.

Instead of directly measuring the deflection of the series springs (#3), sensory information from #1 can be employed. By subtracting the biomimetic joint angle from the active element output shaft angle, it is possible to calculate the amount of energy stored in the motor series spring. Also, the series spring displacement sensor can be used to measure the torque borne by the joint because joint torque can be calculated from the series spring output force.

Many variations exist in the particular sensing methodologies employed in the measurement of the listed parameters. Although preferred sensory methods have been specified, it is noted here that what is critical is to capture the energy state of the spring elements and the velocities of interior points.

In the remaining sections, we present embodiments of the agonist-antagonist actuator capable of providing biologically realistic dynamic behaviors for an artificial ankle and knee joint.

An Agonist-Antagonist Actuator for an Artificial Ankle Joint

Mechanical Design

The ankle design comprises flexion and extension motors for the active elements, and corresponding flexion and extension transmissions and springs. The flexion and extension motors provide control of joint spring equilibrium position and stiffness, damping and non-conservative, motive force output. In the section to follow, we provide an example of how the agonist-antagonist actuator could be employed as an artificial ankle.

Figure 25A:
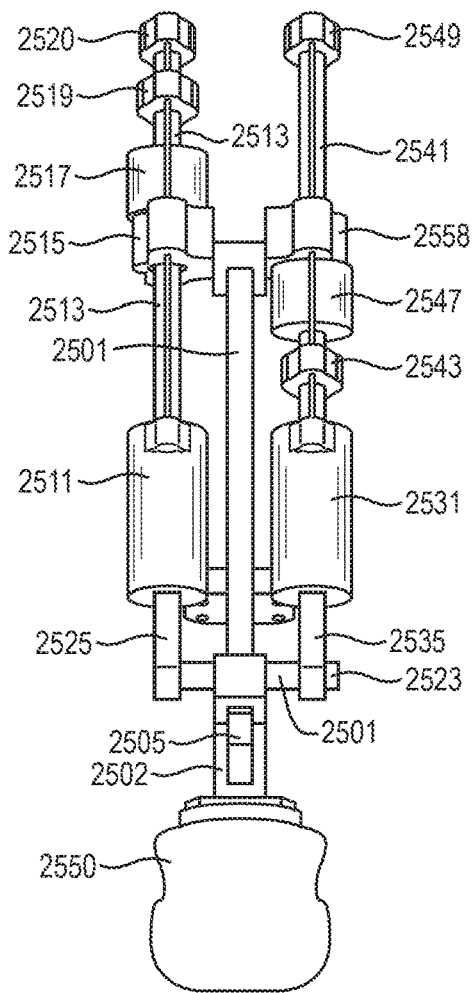
FIGS. 25A and 25B are posterior and side elevational views of an agonist antagonist actuator mechanism implementing an artificial ankle.
Figure 25B:
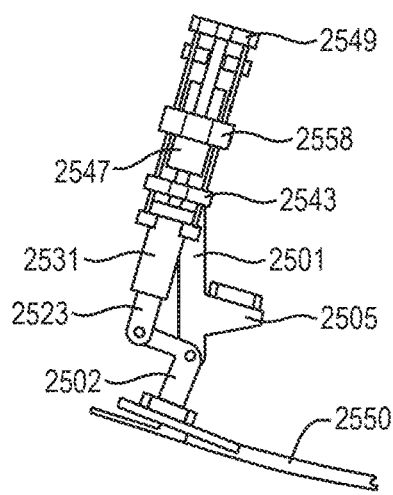

The Agonist-antagonist actuator, as used in an artificial ankle application, is shown in FIGS. 25A and 25B. An upper shin link 2501 and a foot link 2502 rotate with respect to one another about an ankle joint 2505 as best seen in the side view, FIG. 25B. Two actuators extend in parallel alongside the shin link 2501. In the actuator seen at the left in FIG. 25A, a plantar flexion motor 2511 drives a flexion ballscrew 2513 that extends through a linear bearing 2515, a plantar flexion spring 2517 and a plantar flexion nut 2519 to an endcap 2520. The flexion motor 2511 is attached to a crossrod 2523 by a strut 2525. The dorsiflexion actuator is seen at the right in FIG. 25A and includes a dorsiflexion motor 2531 which is attached at its lower end by a strut 2535 to the cross rod 2523. A dorsiflexion ballscrew 2541 is driven by the dorsiflexion motor and extends upwardly through a dorsiflexion nut 2543, a dorsiflexion spring 2547, and a linear bearing 2558 to an endcap 2549. The foot link 2502 is attached to a leaf spring foot plate seen at 2550.

The description that follows explains how, during level-ground walking, the joint might be controlled for the swing, controlled plantar flexion (CP), controlled dorsiflexion (CD), and powered plantar flexion (CP) phases of gait. In addition, the description will explain how the joint might be controlled for stair/slope ascent and descent.

Level-Ground Walking: Swing Phase and CP

During early swing, the plantar flexion ballscrew nut 2519 is positioned such that the ankle joint is dorsiflexed to achieve foot clearance. During terminal stance, three distinct control methods can be employed in preparation for heel strike and the CP phase. In human walking, the amount of energy stored during CP increases with increasing walking speed. To achieve this increase in energy with speed, the total angular deflection of the ankle can be increased with increasing speed and/or the quasi-stiffness or the actual stiffness of the ankle can be increased. Thus, in a first control approach, the effective spring equilibrium length of the actuator at heel strike could be increased with increasing walking speed. Here the spring equilibrium position of the joint is equal to the desired heel strike ankle angle. The effect of this control would be that more mechanical energy is stored in the dorsiflexion spring during CP as walking speed increases. In an alternate approach, during terminal swing both dorsi and plantar flexion motors 2531 and 2511 could do work on their respective series springs in a co-contraction control scheme. If the series springs are hardening springs (stiffness increases with increasing deflection), this cocontraction action would effectively increase the actual stiffness of the actuator, and the ankle joint across which the actuator spans. Still further, in a third approach, the quasistiffness of the actuator/joint could be increased or decreased during CP. For the ankle system shown in FIGS. 25A and 25B, the flexion and extension ballscrews are non-backdriveable. Hence, during CP, if the desired ankle stiffness can be achieved simply by compressing the dorsiflexion spring 2547, the dorsiflexion motor 2531 can be turned off to conserve power. If a lower quasi joint stiffness is required, the dorsiflexion motor 2531 can unwind the dorsiflexion spring 2547 during CP, and if a greater quasi joint stiffness is required, the motor can compress the spring 2547 during CP. Depending on the terrain (smooth or uneven), walking speed, and power consumption constraints, the control algorithm of the artificial ankle will select the appropriate ankle spring equilibrium and stiffness values for terminal swing/CP to achieve a smooth heel strike to forefoot strike transition.

It is noted here that in the invention described herein, there can be separate series spring stiffnesses for joint dorsi and plantar flexion, and these two sets of springs 2517 and 2547 can be selected to give distinct flexion and extension joint stiffnesses at little to no power consumption. If the motors change ankle position when minimal torques are applied to the joint, such as during the swing phase of walking, very little electrical power is required to change the spring equilibrium position of the joint. In the embodiment seen in FIGS. 25A and 25B, where the ballscrews 2513 and 2541 are non-backdriveable, the motors need not consume any electrical power to hold the joint's position even during ground contact. Controlling the joint spring set point at heel strike can be useful, for example, when the wearer switches shoes with different heel heights or when the terrain changes character (slopes/stairs and uneven terrain), thus changing the natural angle of the ankle joint when the foot is resting on a flat ground surface.

Level-Ground Walking: CD and CP Phases

During early CD in human walking, the ankle torque does not return to point 1 in FIG. 20. Rather, the torque assumes a higher value compared to the torque values from points 1 to 2. To achieve this higher torque output, the plantar flexion motor 2511 has to move the plantar flexion nut 2519 to reduce the gap between the nut and the plantar flexion spring 2517 as the dorsiflexion spring 2547 is being compressing during CP. This repositioning of the plantar flexion nut allows the plantar flexion spring to be engaged even before the dorsiflexion spring has released its energy, thus providing a higher torque during early CD than during CP.

During mid to terminal CD in human walking, the ankle torque versus angle curve becomes increasingly nonlinear as walking speed increases. In addition, peak ankle power and the net ankle work during stance increases with increasing walking speed (see FIG. 20). Thus, at 0.9 m/sec, when the human ankle, on average, stores as much energy as it releases, the mechanical response of the artificial ankle during CP will, on average, be dictated by the series, plantar flexion spring. That is to say, the stiffness of the plantar flexion spring will be tuned to correspond to the average, quasi-stiffness (slope of the torque-angle curve) of the human ankle during CD. To decrease the quasi-stiffness of the artificial ankle during CP, the plantar flexion motor would be controlled to unwind the plantar flexion spring, and to increase quasi-stiffness, the motor would compress the spring. Thus, as walking speed increases above 0.9 m/sec, the plantar flexion motor would compress the plantar flexion spring during CD to achieve the following characteristics 1) to increase the quasi-stiffness of the artificial ankle during CD and 2) to increase the power output and the positive work performed during PP. It is noted here that to achieve a passive, spring response during the stance period of walking, the flexion and extension motors can be turned off to conserve power since the ballscrews are non-backdriveable.

From {1} {2}, it has been shown that the maximum dorsiflexion ankle torque during level-ground walking is in the range from 1.5 Nm/kg to 2 Nm/kg, i.e. around 150 Nm to 200 Nm for a 100 kg person. Further, the maximum controlled plantar flexion torque is relatively small, typically in the range of 0.3 Nm/kg to 0.4 Nm/kg. Because of these biomechanics, a uni-directional spring in parallel with the agonist-antagonist actuator of FIGS. 25A and 25B would lower the peak torque requirements of the actuator. The uni-directional spring would engage at a small or zero dorsiflexion angle (90 degrees between foot and shank) and would lower the peak torque requirements of the Agonist-antagonist actuator since the peak controlled plantar flexion torque is considerably smaller than the peak dorsiflexion torque. Thus, additional elements could be added to the design of FIG. 25 such as a parallel, uni-directional spring.

Stair/Slope Ascent and Descent

For ascending a stair or slope, the dorsi and plantar flexion motors would move the nuts to reposition the ankle joint to an appropriate angle given the nature of the stair/slope. Once the artificial toe is loaded at first ground contact, the plantar flexion spring compresses and stores energy. During this CD process the plantar flexion motor can compress the spring farther so that additional power is delivered to the walking robot or prosthesis/orthosis user during PP. After toe-off, the motors control the equilibrium position of the ankle in preparation for the next step.

During stair descent, the body has to be lowered after forefoot contact until the heel makes contact with the stair tread. See re reference {2}. During this CD phase, the plantar flexion motor unwinds the plantar flexion spring as the spring is compressing to effectively dissipate mechanical energy. Once the heel makes contact with the stair tread, the motor can be turned off so that the plantar flexion spring begins to store energy for release during PP. For slope descent, the ankle response is similar, except that mechanical energy is absorbed by the dorsiflexion motor during CP instead of during CD.

An Agonist-Antagonist Actuator for an Artificial Knee Joint

The knee design comprises an extension motor and a flexion variable damper for the active elements, and corresponding flexion and extension transmissions and springs. The extension motor and the flexion variable damper provide control of joint spring equilibrium position and stiffness, damping and nonconservative, motive force output. In this implementation of the agonist-antagonist actuator, a flexion motor is not included in an attempt to simplify the mechanism. Since only a flexion variable damper is present, the flexion nut is mechanically grounded to the linear bearing since a flexion motor is not present to actively reposition the flexion nut. Hence, when the knee joint flexes and extends, the flexion ballscrew rotations, but that rotation does not introduce significant zero-power joint resistance because 1) the flexion ballscrew is highly backdriveable and 2) the flexion variable damper has a negligible low-end damping value. A preferred method for the flexion variable damper is a hysteresis brake because of its minimal low-end damping value. In the section to follow, we provide an example of how the agonist-antagonist actuator could be employed as an artificial knee.

Figure 26A:
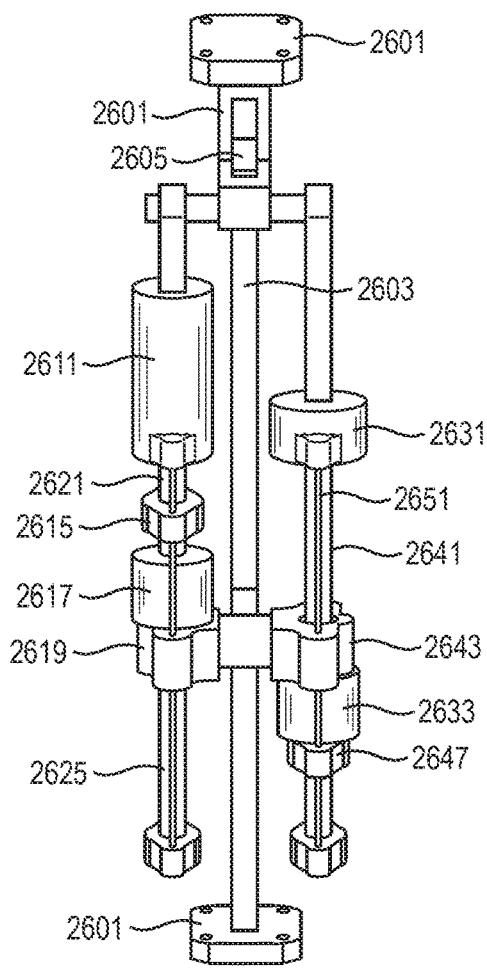
FIGS. 26A and 26B are posterior and side elevational views of agonist-antagonist actuator mechanisms implementing an artificial knee.
Figure 26B:
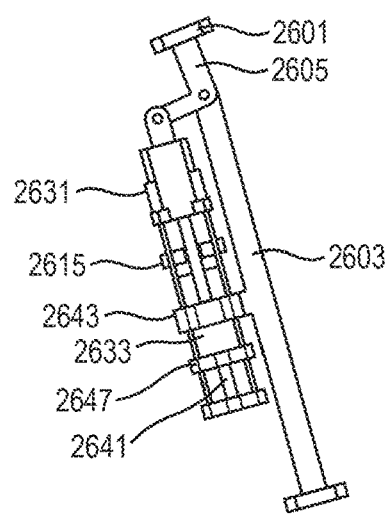
Figure 27A:
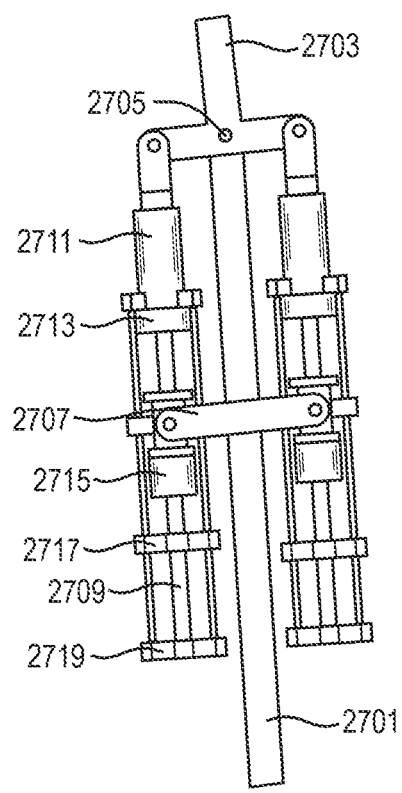
FIGS. 27A and 27B are side elevational and perspective views of an agonist antagonist actuator mechanism positioned on both sides of the joint axis.
Figure 27B:
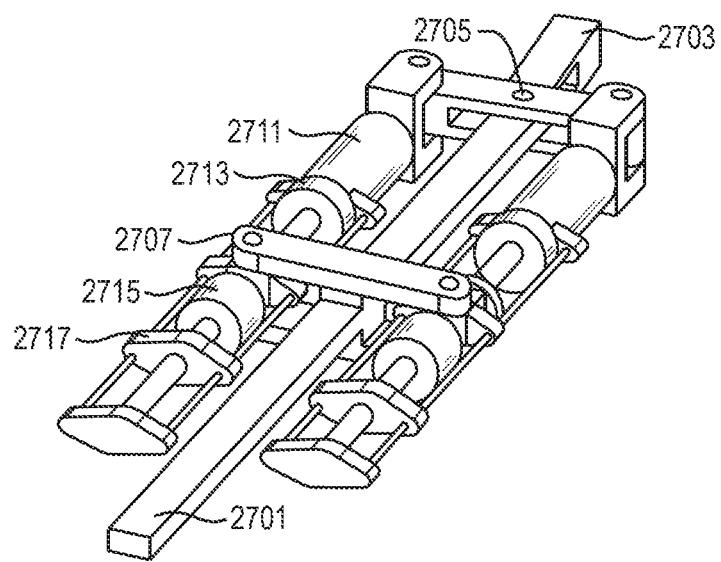

The agonist-antagonist actuator, as used in an artificial knee application, is shown in FIGS. 26A and 26B. The actuator consists of an upper (thigh) link 2601 and a lower (shin) link 2603 which are rotatably connected at a joint 2605. As seen at the left of the lower link 2603, an extension motor 2611 drives an extension ballscrew 2621 that extends downwardly from the motor 2611 through an extension nut 2615, an extension spring 2617, and a linear bearing 2619. An extension nut guidance shaft 2625 prevents the extension nut from rotating as the extension ballscrew 2621 rotates.

The mechanism on the right side of the lower link 2603 is passive; that is, it does not include an active motor element but rather includes a flexion variable damper 2631 and a flexion spring 2633. A flexion ballscrew 2641 extends from the damper 2631 downwardly through a linear bearing 2643, the flexion spring 2633 and a flexion nut 2647. A flexion nut guidance shaft 2651 prevents the flexion nut 2647 from rotating as the extension ballscrew 2641 rotates.

Level-Ground Walking

During level-ground walking, the joint is controlled for the swing, early stance flexion, mid-stance extension, and pre-swing phases of gait. In addition, as described below, the joint may be controlled for stair/slope ascent and descent. Beginning at heel strike, the stance knee begins to flex slightly in normal human walking (FIG. 23). As was noted earlier, this flexion period, called the Stance Flexion phase, allows for shock absorption upon impact as well as to keep the body's center of mass at a more constant vertical level throughout the stance period. During this phase, the artificial knee shown in FIGS. 26A and 26B outputs a spring response, storing energy in preparation for the Stance Extension phase. Here the extension spring 2617 stores energy, and then that energy is released during the Stance Extension phase. In this implementation of the agonist-antagonist actuator, the extension ballscrew transmission is non-backdriveable. Thus, if the desired actuator stiffness during Stance Flexion corresponds to the extension spring stiffness, the extension motor need not be active, reducing electrical power requirements. If a higher or lower quasi joint stiffness is desired, the extension motor 2611 can compress or unwind the extension spring 2613 during early stance knee flexion, respectively, by repositioning the extension nut 2615 that acts on the extension spring 2617.

After maximum flexion is reached in the stance knee in normal human walking, the joint begins to extend, until maximum extension is reached. This knee extension period is called the Stance Extension phase. Throughout the first ~60% of Stance Extension, the knee acts as a spring, releasing the stored energy in the extension spring from the Stance Flexion phase of gait. This first release of energy corresponds to power output P2 in FIG. 23B. During the last ~30% of Stance Extension, the artificial knee is controlled to absorb energy in the flexion spring 2633 and then that energy is released during the next gait phase, or Pre-Swing. Here the energy from hip muscular work and the remaining stored energy in the extension spring 2617 is then stored in the flexion spring 2633. To engage the flexion spring, the flexion variable damper 2631 outputs a high damping value, locking the flexion ballscrew 2641, and forcing the flexion nut 2647 to compress the flexion spring 2633. During this energy storage, if it is desirable to lower the effective quasi-stiffness of the joint, the flexion variable damper 2631 can output lower damping values to allow the flexion ballscrew 2641 to slip, and for energy to be dissipated as heat. Here again, as in the artificial ankle joint of FIGS. 25A and 25B, the flexion and extension springs of the agonist antagonist actuator of FIGS. 26A and 26B are precisely tuned such that biological knee mechanics can be achieved while minimizing power supply demands and overall artificial joint mass.

During late stance or Pre-Swing, a normal human knee of the supporting leg begins its rapid flexion period in preparation for the swing phase. During early Pre-Swing in the artificial knee joint of FIGS. 26A and 26B, as the knee begins to flex in preparation for toe-off, the stored elastic energy in the flexion spring 2633 stored during Stance Extension is released. This second release of energy corresponds to power output P3 in FIG. 23B. During this process, the flexion variable damper 2631 can be used to modulate the amount of stored elastic energy in the flexion spring that is actually released to power the knee joint.

In normal human walking, as the hip is flexed, and the knee has reached a certain angle in Pre-Swing, the leg leaves the ground and the knee continues to flex. At toe-off, the Swing Flexion phase of gait begins. Throughout this period, human knee power is generally negative where the knee's torque impedes knee rotational velocity. In the artificial knee joint of FIGS. 26A and 26B, once the elastic energy from the flexion spring 2633 has been released and the artificial leg has entered the swing phase, the knee joint typically has to absorb mechanical energy to decelerate the swinging lower leg. This can be done in two ways. First, the flexion variable damper 2631 can be used to dissipate mechanical energy as heat and to decelerate the swinging artificial leg. In addition, during late Swing Flexion, the extension motor 2611 can position the extension ballscrew nut 2615 such that the extension spring 2617 compresses and stores elastic energy for use during Swing Extension.

After reaching a maximum flexion angle during swing, a normal human knee begins to extend forward. For the artificial knee of FIGS. 26A and 26B, during the early Swing Extension period, the elastic energy stored during late Swing Flexion in the –extension spring 2617 is released, resulting in power output P4 in FIG. 23B. This control action, once again, reduces the energy demands from the knee's power supply. In all cases, the flexion variable damper 2631 can be used to precisely modulate the amount of power delivered to the swinging artificial leg from the stored elastic energy.

During the remainder of Swing Extension, the human knee typically outputs negative power (absorbing energy) to decelerate the swinging leg in preparation for the next stance period. As with Swing Flexion, this can be done in two ways. First, the flexion variable damper 2631 can be used to dissipate mechanical energy as heat and to decelerate the swinging artificial leg. In addition, during late Swing Extension, the flexion variable damper 2631 can output a relatively high damping value such that the flexion spring 2633 compresses and stores elastic energy for use during Stance Flexion. Here a small amount of energy is stored in preparation for early stance (power P1). After the knee has reached full extension, the foot once again is placed on the ground, and the next walking cycle begins.

In summary, the artificial knee shown in FIGS. 26A and 26B is capable of reproducing the positive power contributions P1, P2, P3 and P4 shown in FIG. 23 for level ground walking.

Stair/Slope Ascent and Descent

For stair/slope descent, a normal human knee performs negative work during stance where knee torque is in the opposite direction to knee rotational velocity. The agonist-antagonist actuator of FIGS. 26A and 26B can perform this negative work in two ways. First, the flexion variable damper 2631 can be used to dissipate mechanical energy as heat and to decelerate the rotating artificial leg. In addition, during terminal stance, the extension motor 2611 can position the extension ballscrew nut 2615 such that the extension spring 2617 compresses and stores elastic energy for use later to power Swing Extension to prepare the artificial leg for the next stance period.

For stair/slope ascent, during the swing phase the extension motor 2611 can actively control knee position to accurately locate the foot on the next stair tread or slope foothold. Once the artificial foot is securely positioned on the stair tread or ground, the motor 2611 can then deflect and store energy in the extension spring 2617. This stored elastic energy can then assist the knee wearer or humanoid robot to actively straighten the knee during the stance period, lifting the body upwards.

Finally, the agonist-antagonist actuator of FIGS. 26A and 26B allows for the "windup" phase of a catapult style control to occur at any desired time. This means much greater flexibility as to when large amounts of power can be efficiently generated and used. This flexibility is critical when designing an artificial knee that can be used for jumping. For such a movement task, energy has to be stored prior to the jump, and then the elastic energy has to be released at a precise time to facilitate a jumping action. Specifically, for the agonist-antagonist actuator of FIGS. 26A and 26B, the flexion variable damper 2631 would be controlled to output high damping to effectively lock the flexion ballscrew 2641. Following this action, the extension motor 2611 would slowly compress the extension spring 2617. Once high powers are deemed necessary about the joint output, the flexion variable damper 2631 would then be controlled to suddenly unlock to allow rapid rotation of the flexion ballscrew 2641 and the release of elastic strain energy from the extension spring 2617.

Alternative Configurations of the Agonist-Antagonist Actuator

It should be understood that the agonist-antagonist actuator described herein could be implemented in a number of different ways. For example, an active element and transmission-spring combination could be positioned on each side of the artificial joint. This configuration, shown in FIGS. 27A-B, has the advantage that when only one spring is being compressed, no off-axis bending torques are borne by the lower link seen at 2701. The lower link 2701 is attached to the upper link 2703 at a joint 2705. A crossbar strut 2707 is rigidly attached to the lower link 2701. A linear bearing is attached to each end of the crossbar strut 2707 and a ballscrew, one of which is seen at 2709, extends through the linear bearing. The ballscrew seen at 2709 extends downwardly from a drive motor 2711 through a variable damper 2713, the linear bearing, a spring 2715, and a ballscrew nut 2717 to an end cap 2719.

In the agonist-antagonist actuator implementations shown in FIGS. 24, 25 and 26, when only a single spring is being compressed, the upper and lower links experience a bending torque because the pair of active element-transmission-spring combinations are on the same side of the joint axis. It should also be understood that more than two active element-transmission-spring combinations could be employed to actuate multiple degrees of freedom. For example, in FIG. 28, four active element-transmission-spring combinations are shown to actuate a two degree of freedom joint. Still further, it should be understood that an agonist-antagonist actuation system can include active element transmission-spring combinations than span two or more joints in a poly-articular architecture. The biomechanics of poly-articular actuation is discussed in the next section.

Figure 28A:
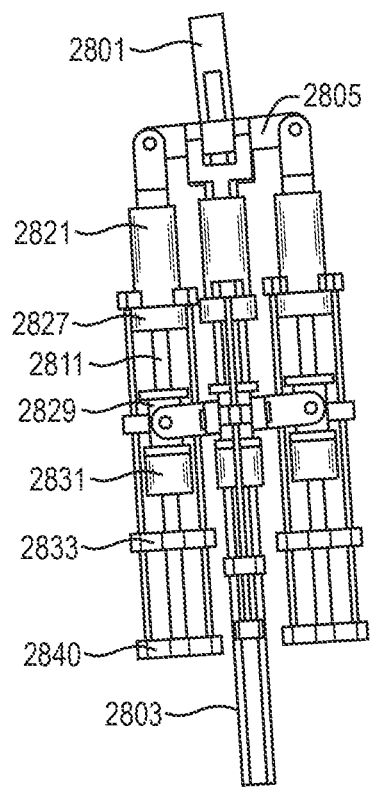
FIGS. 28A and 28B are posterior and side elevational views of an agonist antagonist actuator mechanism using motor and spring combinations.
Figure 28B:
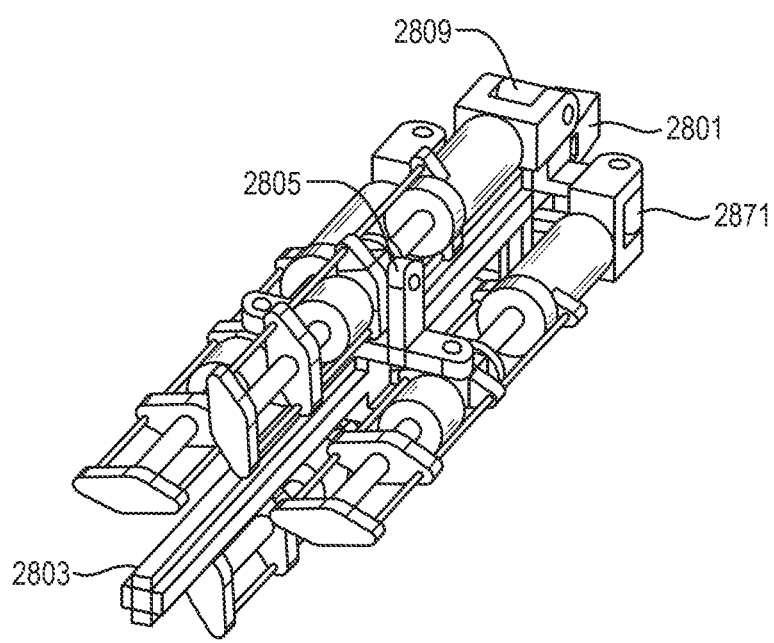

In the arrangement shown in FIG. 28, the joint attaches an upper link 2801 to a lower link 2803 for rotation about two orthogonal axes. As seen in FIG. 28B, the upper link rotates in a first degree of freedom about an axis through the crossbar 2807 that is parallel to the long dimension of a crossbar 2809, and in a second degree of freedom about an axis through the crossbar 2809 that is parallel to the crossbar 2807. Four different actuators are attached from the ends of the crossbars 2807 and 2809 and all four have a like structure illustrated by the actuator at the left in FIG. 28A. An drive motor 2821 attached to the crossbar 2805 rotates a ballscrew 2822 that passes through variable damper 2827 and a linear bearing 2829 attached to the lower link 2803. The ballscrew 2822 further extends through a series spring 2831 and a ballscrew nut 2833 to an endcap 2840. For each degree of freedom, one of the motor-spring-damper mechanisms controls the rotation of the upper link 2801 with respect to the lower link 2803 in one direction while an opposing motor-spring-camper mechanism attached to other end of the same crossbar controls the rotation in that degree of freedom in the other direction, thus providing agonist-antagonist actuator control in both degrees of freedom.

Agonist-Antagonist Actuators Spanning More than One Joint

In the foregoing description, the agonist-antagonist actuator mechanism contemplated by the present invention was described and specific examples were provided as to its use in ankle and knee actuation, and different illustrative implementations were described. For each of these implementations, the agonist-antagonist actuator spanned a single joint. In other implementations, an agonist-antagonist actuator may span more than one rotary joint. The functional purpose of polyarticular muscle architectures in the human leg is to promote the transfer of mechanical energy from proximal muscular work to distal joint power generation. See reference {10}. To capture truly biomimetic limb function, both muscle-like actuators and mono, bi, and poly-articular artificial musculoskeletal architectures are critical. Hence, it should be understood that the agonist-antagonist actuator described herein could span more than one artificial joint. For example, an active element-transmission-spring combination could act across the hip and knee of an artificial leg, or across the knee and ankle of an artificial leg.

The Biomechanics of Mono and Bi-Articular Leg Actuation

In the previous sections, an agonist-antagonist actuator was described and specific examples were provided as to its use in ankle and knee actuation. For each of these descriptions, the actuator was used as a mono-articular device, spanning only a single joint. In subsequent embodiments, we describe how mono-articular actuation strategies can be used in combination with bi-articular actuation strategies to better replicate biological limb dynamics and efficiency.

The functional purpose of bi-articular muscle architectures in the human leg is to promote the transfer of mechanical energy from proximal muscular work to distal joint power generation {10}. To better explain how bi-articular actuation effects biological limb energetics, we present a biomechanical model of the human musculoskeletal architecture in FIG. 29A {11}. By modeling the human leg, we seek to understand how leg muscles and tendons work mechanically during walking in order to motivate the design of efficient prosthetic, orthotic, and robotic limbs.

We hypothesize that a robotic leg comprising only knee and ankle variable impedance elements, including springs, clutches and variable-damping components, can capture the dominant mechanical behavior of the human knee and ankle for level-ground ambulation. As a preliminary evaluation of this hypothesis, we put forth a simple leg prosthesis model, shown in FIG. 29A, that is motivated by the human leg musculoskeletal architecture {29}. The model seen in FIG. 29A includes a drive motor 2901 at the hip, a knee joint 2903 and an ankle joint 2905. A musculo-skeletal model of human leg function in walking. The model comprises seven monoarticular series elastic clutches and four bi-articular series-elastic clutches/variable-dampers. Only a single actuator 2901 acts at the model's hip joint. In (B) and (C), model predictions for ankle and knee are compared with human gait data, respectively. Here gait data are shown for a 70 kg study participant with a 0.9 meter leg length and a walking speed of 1.2 m/s. The model of (A) agrees well with the human gait data, suggesting that muscles that span the ankle and knee primarily act as variable-impedance devices during level-ground walking. We vary quasi-passive model parameters, or spring constants, damping levels and times when series-elastic clutches are engaged, using an optimization scheme where errors between model joint behaviors and normal human joint biomechanics are minimized.

The capacity of the musculoskeletal leg model to capture human-like ankle and knee mechanics in level-ground walking is shown in FIGS. 29B and 29C, respectively. At each joint state (position and velocity), the leg model is in good agreement with experimental values of joint torque and power, suggesting that a robotic leg can produce human-like walking dynamics through the control of only knee and ankle impedance.

Mono-Articular Ankle Mechanism.

Figure 29A:
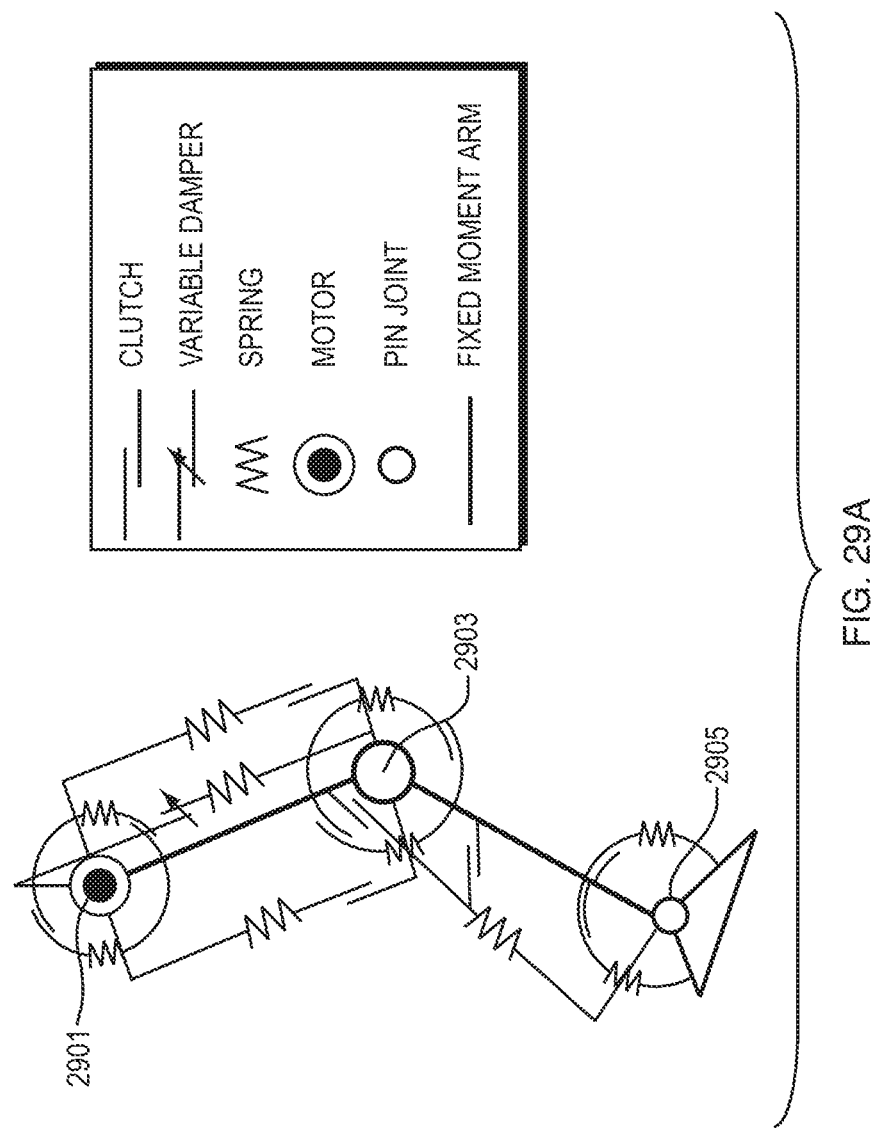
FIG. 29A shows a model of leg prosthesis employing series-elastic clutches at the hip, knee and ankle joints.
Figure 30A:
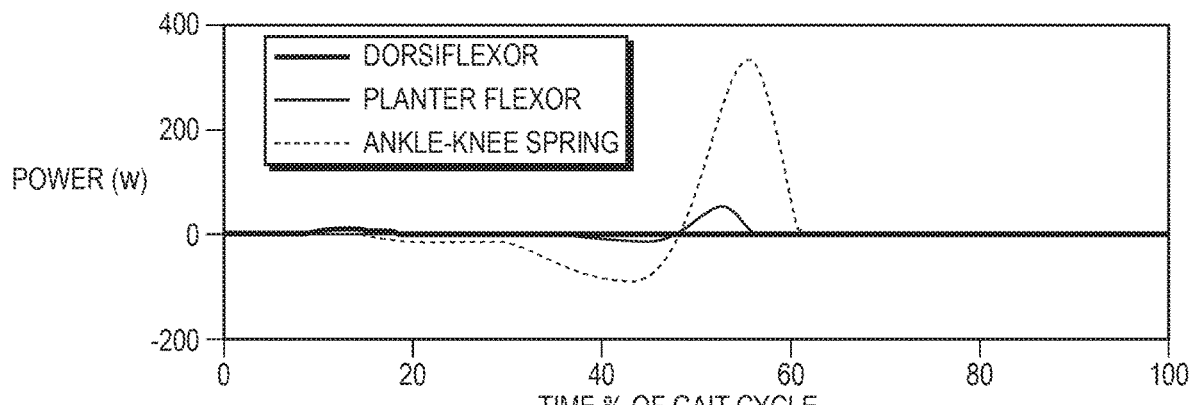
FIGS. 30A, 30B and 30C are plots of the mechanical power of each model element is versus percentage gait cycle for ankle, knee and hip, respectively.

The ankle mechanism comprises monoarticular dorsi and plantar flexion springs that can be engaged or disengaged with series elastic clutch mechanisms (see FIG. 29A). In FIG. 30A, the mechanical power for each ankle component is plotted versus percent gait cycle. At heel strike (0% cycle), the clutch for the ankle dorsiflexion spring is engaged, causing the spring to stretch and store energy during early stance plantar flexion. When the tibia begins rotating forwardly after forefoot contact, the ankle plantar flexion spring is engaged and continues to store energy throughout the controlled dorsiflexion phase, and then that stored energy is released to contribute to ankle powered plantar flexion at terminal stance. Mechanical power output for each component of the human leg model of FIG. 29A.

In (A), (B) and (C), the mechanical power of each model element is plotted versus percentage gait cycle for ankle, knee and hip, respectively. Here the gait cycle begins at heel strike (0%) and ends with the heel strike of the same leg (100%).

Mono-Articular Knee Mechanism.

Figure 30B:
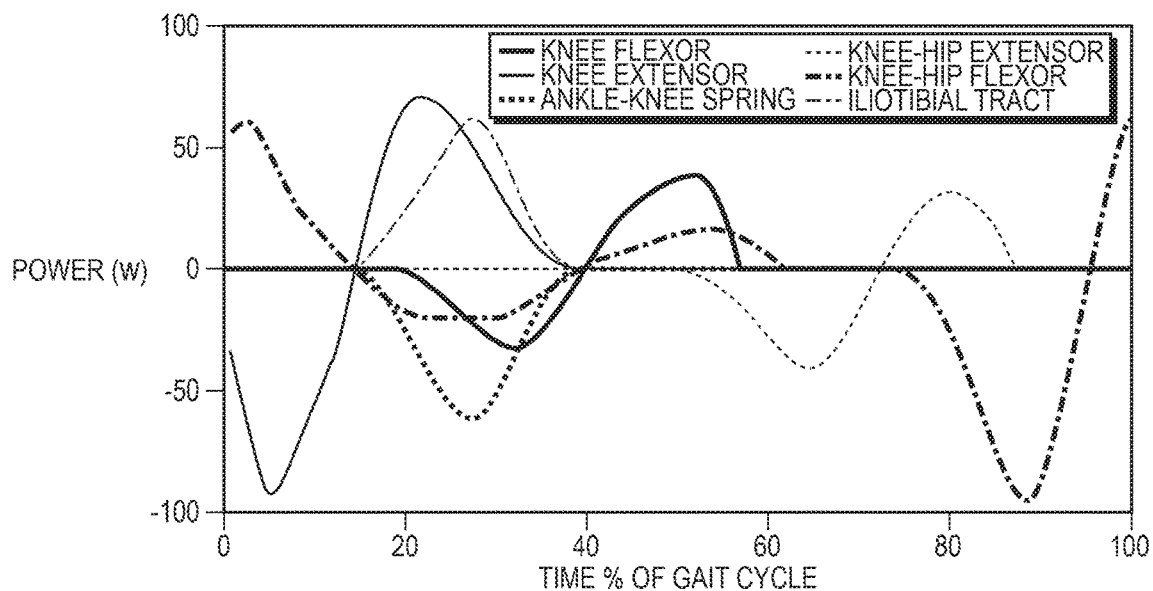
Figure 30C:
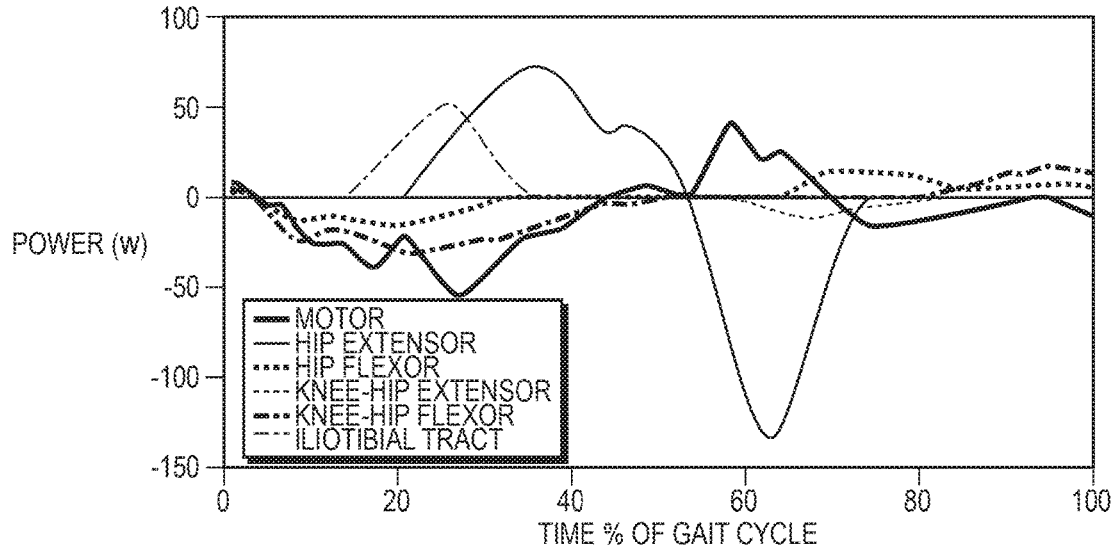

The knee mechanism comprises monoarticular flexion and extension springs that can be engaged or disengaged with series elastic clutch mechanisms (see FIG. 29A). In FIG. 30B, the mechanical power for each knee monoarticular component is plotted versus percent gait cycle. At heel strike (0% cycle), the clutch for the knee extensor spring is engaged, causing the spring to stretch during early stance knee flexion. Here the knee extensor spring inhibits the knee from buckling. As the knee extends from a flexed posture, the knee flexor spring is engaged at the point of maximum knee extension velocity, storing energy that is subsequently used during terminal stance to help lift the lower leg from the ground surface.

Ankle-Knee Bi-Articular Mechanism.

The leg model's ankle-knee biarticular mechanism comprises a spring that can be engaged or disengaged with two clutch mechanisms (see FIG. 29A). A first clutch, or the distal clutch, attaches the series spring to a point between the ankle and knee joint, and a second clutch, or the proximal clutch, attaches that same spring to a point above the knee axis. After heel strike in human walking, the knee typically undergoes a flexion period. During that phase of gait, both the proximal and distal clutches are disengaged, and the bi-articular spring does not apply a force to the prosthesis skeleton. However, as the knee begins to extend (~10% cycle), the proximal clutch engages, and the bi-articular spring stretches. When the knee is fully extended, the distal clutch changes from a disengaged state to an engaged state, and the proximal clutch disengages. Engaging the distal clutch mechanically grounds the bi-articular spring below the knee rotational axis, changing the ankle-knee mechanism from a bi-articular to a mono-articular device. As a consequence of this action, all the energy stored in the bi-articular spring is used to power ankle plantar flexion during terminal stance. Thus, in summary, the ankle-knee mechanism allows energy from hip muscular/actuator work to be transferred to the ankle for late stance powered plantar flexion.

Knee-Hip Bi-Articular Mechanism.

The leg model's knee-hip bi-articular mechanisms comprise a spring that can be engaged or disengaged with either a clutch or variable-damper mechanism (see FIG. 29A). There are three knee-hip bi-articular mechanisms. The clutch of the knee-hip flexor is engaged during swing phase knee extension and begins storing energy its series spring. As a result of this control action, the lower leg is decelerated smoothly prior to reaching full knee extension. In addition, elastic energy is stored in the knee-hip flexor spring that is later released during the early stance period. The knee-hip flexor also undergoes an energy storage/release sequence that begins during stance knee extension. The stored energy is then released to power rapid knee flexion movements at terminal stance to lift the foot and lower leg from the ground surface. The clutch of the knee-hip extensor is engaged during terminal stance, storing energy that is later released to enhance knee extension. Finally, the iliotibial tract series-elastic variable-damper applies an extensor knee torque to offset the knee flexor torque applied by the ankle-knee bi-articular mechanism. During stance knee extension, the ankle-knee bi-articular spring is elongated, exerting a torque about the knee. At the same time the iliotibial tract series spring is elongated thereby applying an extensor torque at the knee. Thus, through the action of the iliotibial tract mechanism, the effect of the ankle-knee bi-articular mechanism on net knee torque is minimized.

In the human leg, the functional purpose of bi-articular muscle is to promote the transfer of mechanical energy from proximal muscular work to distal joint power generation {10}. Using the biomimetic architecture shown in FIG. 29A, the robotic leg can achieve ankle powered plantar flexion without the requirement of powering a large motor located at the ankle joint. Approximately ten joules of network are transferred to the ankle from the knee and hip in the modeling results shown in FIGS. 29B-C and 30A-C.

In subsequent embodiments, we motivate the design of prosthetic, orthotic and robotic leg structures using the leg model of FIG. 29A.

Mono and Bi-Articular Actuation for a Transtibial Prosthetic Leg System

The prosthetic leg model of FIG. 29A suggests that leg prostheses could produce human-like joint mechanics during level-ground ambulation if a musculoskeletal leg architecture and a variable-impedance control paradigm were exploited. However, the proposed biomimetic leg prosthesis does not eliminate the need for knee and ankle actuators, but the model does suggest that non-conservative joint actuator work need not be performed during normal, steady state walking. For some situations, positive joint actuator work is required. For example, for uphill locomotory function, some positive actuator work would be necessary, especially at the knee. Furthermore, ankle and knee torque control would be necessary to reject large whole-body force disturbances that threaten balance. Although joint actuation is still necessary, the proposed biomimetic design will increase the time between battery recharges or power supply refueling, and will reduce robotic limb noise production during level-ground walking.

Figure 31C:
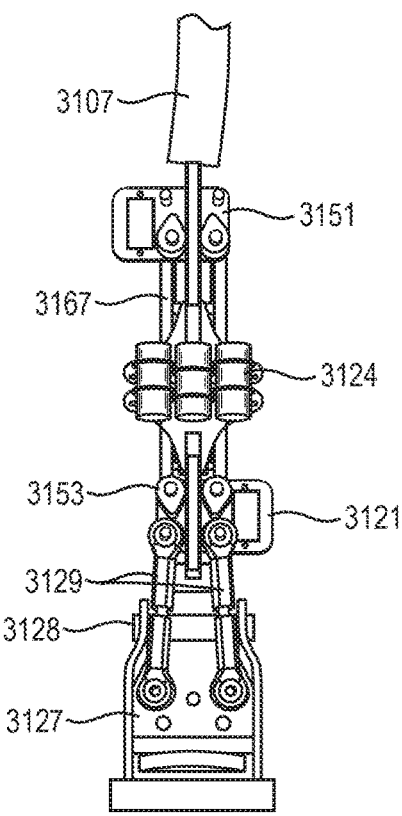
FIGS. 31C and 31D show elevational and schematic views respectively of the bi-articular ankle knee mechanism of FIG. 31A.
Figure 31D:
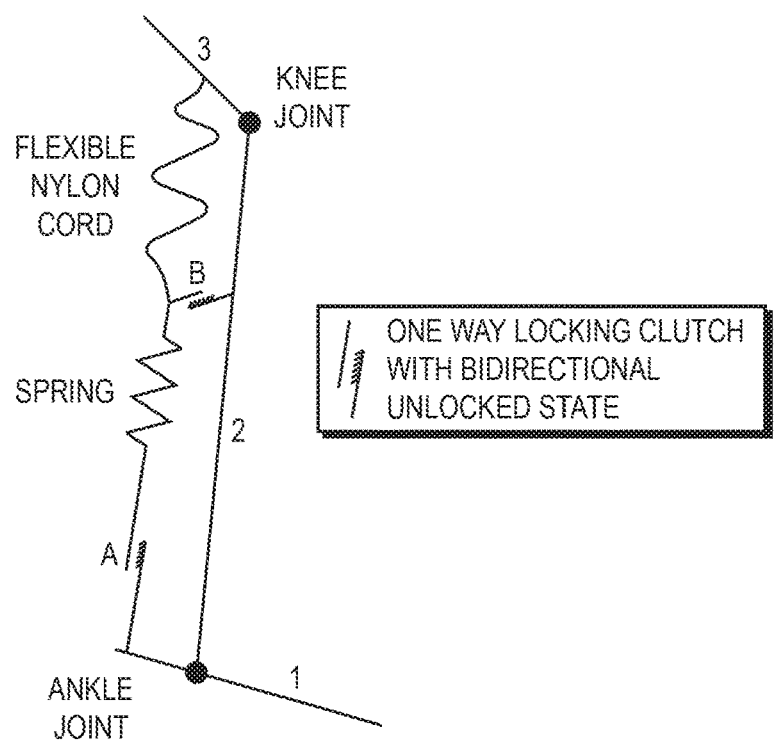

In FIGS. 31A-D, the design of the proposed transtibial ankle-foot system with mono and bi-articular mechanisms is shown. In FIG. 31A, the major components of the transtibial system are shown, including the mono-articular ankle mechanism at 3103, the bi-articular ankle-knee mechanism at 3105, and a flexible nylon cord at 3107. FIG. 31B shows the monoarticular ankle mechanism in more detail. This mechanism comprising two motors 3113, mechanical transmissions and series dorsiflexion springs at 3117, and series plantar flexion springs at 3119. FIG. 31C shows the bi-articular mechanism (3105 in FIG. 31A) and FIG. 31D shows a schematic of the bi-articular mechanism, including two uni-directional clutches seen at 3121 and 3151 and a series spring at 3124. The limb architecture largely reflects the leg model shown in FIG. 29A, except the monoarticular knee mechanism has been excluded as this basic musculoskeletal structure is still intact in transtibial amputees.

The ankle mechanism 3103 seen in FIG. 31B comprises two agonist-antagonist, series-elastic actuators acting across the ankle joint. The foot-ankle design is similar to that described earlier in FIGS. 25A-B. Each actuator has a small electric motor 3113 in series with one of the die springs 3117 or 3119. Each series spring is a nonlinear hardening spring where spring stiffness increases with increasing spring compression. A non-back driveable leadscrew 3131 is employed to covert rotary motor movement into linear movement of a leadscrew nut 3132. A slider mechanism is seen at 3134 and a guide rod at 3135. By re-positioning the leadscrew nut 3132, each motor 3113 can independently vary the position of the ankle joint at which the series spring 3117 or 3119 becomes engaged. Such an ankle spring equilibrium control is important for many prosthesis functions, including slope and stair ascent and descent. The mono-articular ankle mechanism can also change ankle spring stiffness. During the swing phase each motor can simultaneously compress each nonlinear spring using a co-contraction control. Since spring stiffness increases with increasing deflection, the more the motor system compresses the springs, the stiffer the ankle joint becomes. Since the mechanical transmission is non-backdriveable, once a desired ankle stiffness has been achieved, the motors can be turned off to save electrical power. The foot-ankle design is similar to that described earlier in FIGS. 25A-B.

In FIGS. 31C and 31D, the bi-articular ankle-knee mechanism and schematic are shown, respectively. The mechanism comprises two uni-directional clutches seen at 3151 and 3121 and a spring at 3124. Each clutch is formed by two opposing cams (see 3153) that press against a shaft that directly connects to the spring. At the bottom of FIG. 31C, a foot assembly is seen at 3127 and the ankle axis is at 3128. The ankle joint connection is seen at 3129. In an engaged state, the cam configuration only allows for shaft movement in one direction. As can be seen in FIG. 31D, if both uni-directional clutches A and B are in the disengaged state, with each cam pair rotated outwardly with a small cam motor, the ankle and knee can freely rotate without the biarticular spring exerting a force. When the ankle dorsi and plantar flexes in this disengaged state, the lower floating cam-clutch assembly 3121 translates on the linear guide rail 3167. Furthermore, when the knee flexes and extends, the entire spring assembly translates on the linear guide rail 3167. In distinction, when both clutches are in their engaged state, both ankle dorsiflexion and knee extension cause the bi-articular spring 3124 to stretch and store energy. Since the flexible nylon cord 3107 can resist tension but not compression, once the knee has reached full extension during the stance phase, knee flexion throughout terminal stance is not restricted by the bi-articular assembly, and all the stored energy in the bi-articular spring augments ankle powered plantar flexion.

Sensors for Active Ankle-Foot Prosthesis

For the active transtibial prosthesis to function properly, there are various sensors required to measure the state of the various system components and the intent of the amputee user. The additional sensors required to enable general prosthesis operation and control are:

4) position sensors located at the knee and ankle axes to measure joint angles (rotary potentiometers), and on each motor shaft to measure total displacement and velocity of each motor (a shaft encoder);

5) an inertial measurement unit (IMU) to determine the absolute position of the prosthesis in space;

6) a displacement sensor on each spring in order to measure the amount of force borne by a spring and the torque borne by the ankle joint; and 7) electromyographic (EMG) sensors to determine residual limb muscle activity.

Series spring displacement sensors can be used to determine the torque borne by the ankle joint because joint torque can be calculated from the agonist-antagonist spring output forces.

Control for Active Ankle-Foot Prosthesis

Local Prosthesis Control.

A critical advantage of the human-like musculoskeletal prosthesis is that it allows the amputee user to directly control ankle powered plantar flexion. Because of the bi-articular ankle-knee mechanism, the extent of midstance knee extension defines how much energy is transferred to the prosthetic ankle for powering ankle plantar flexion at terminal stance. Since transtibial amputees generally have direct control over their knee, the biomimetic transtibial prosthesis allows for direct control over ankle power output.

The point in the gait cycle where the prosthesis series spring elements are engaged will largely be defined by joint state (position and velocity) and foot-ground interaction forces. The spring equilibrium angle for the ankle mono-articular mechanism will be equal to the ankle angle at first heel strike. Here heel strike will be detected using ankle torque sensing. For level ground ambulation, the heel strike ankle angle will be kept largely invariant with walking speed, but will be modulated from step to step for slope and stair ambulation.

The uni-directional clutch devices in the bi-articular mechanism will be controlled in a speed invariant manner. After heel strike in walking, the knee typically undergoes a flexion period. During that phase of gait, both bi-articular clutches will be disengaged, and therefore the bi-articular spring will not apply a force to the prosthesis skeleton. However, as the knee begins to extend (~10% cycle), both clutches will be engaged, causing the bi-articular spring to stretch. Once the prosthesis enters the swing phase as detected by zero ankle torque, the bi-articular clutches will be disengaged so as to allow unrestricted knee and ankle movement throughout the swing phase.

Electromyographic (EMG) Control of Prosthetic Ankle Stiffness.

The residual anatomy will allow amputees to voluntarily control joint stiffness via activation of the muscles in the residual limb. When walking on a rigid ground surface, the amputee user can select a low ankle stiffness, whereas when walking on a compliant terrain, the amputee can exploit a relatively high ankle stiffness.

Within the human body, such voluntary changes in joint stiffness are modulated by muscular co-activation. When antagonist muscles are simultaneously recruited, the net torque produced about the joint is related to the difference between the forces generated by the activated muscles, while the joint stiffness is related to their sum. Thus, activity from residual muscles is a natural control source for specifying the desired level of ankle stiffness. Since EMG provides a measure of muscular effort, it can be used in a "natural" manner to control stiffness of a joint. For a transtibial amputee, the muscles of the anterior and posterior compartment of the leg form the natural location from which to derive stiffness control signals.

A joint stiffness control signal is derived from the sum of the plantar flexion and dorsiflexion EMG amplitudes. The stiffness control signal will be related to stiffness via a straightline relationship with a zero-level control signal signifying the minimum available stiffness level and the maximum-level control signal signifying the maximum available stiffness level. Thus, limited muscle effort results in a low ankle stiffness while high muscular effort results in a high ankle stiffness. Using this control strategy, stiffness can be volitionally controlled by the amputee in a natural manner.

Although the device of FIGS. 31A-31D was described as a transtibial prosthesis, the mechanism could also be used as an orthosis or exoskeleton. The mechanism would be useful as an orthosis for an individual that suffers from an ankle pathology but generally has normal knee and hip function. For such an application, the mechanism would be placed in parallel with the human leg to augment ankle mechanics as a permanent assistive device.

Mono and Bi-Articular Actuation for an Artificial Ankle and Knee System

Description

A proposed artificial ankle and knee system is shown in FIGS. 32A-D. The mechanism could be employed for a transfemoral prosthesis, orthosis, leg exoskeleton, or robotic leg. The mono-articular ankle-foot 3103 and knee 3201 designs are identical to the structures described in FIG. 31B and FIG. 26, respectively. However, the ankle-knee biarticular mechanism 3210 is different from that proposed in FIGS. 31C and 31D. The biarticular device of FIG. 31 has to be attached above the knee axis. In distinction, the biarticular device 3210 of FIGS. 32A-32D attaches adjacent to the knee axis.

Figure 32A:
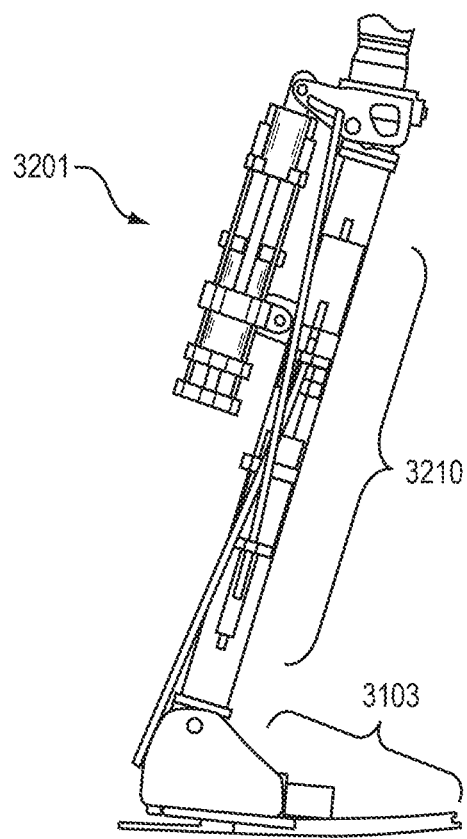
FIGS. 32A and 32B shows the major components of an artificial ankle and knee system.
Figure 32B:
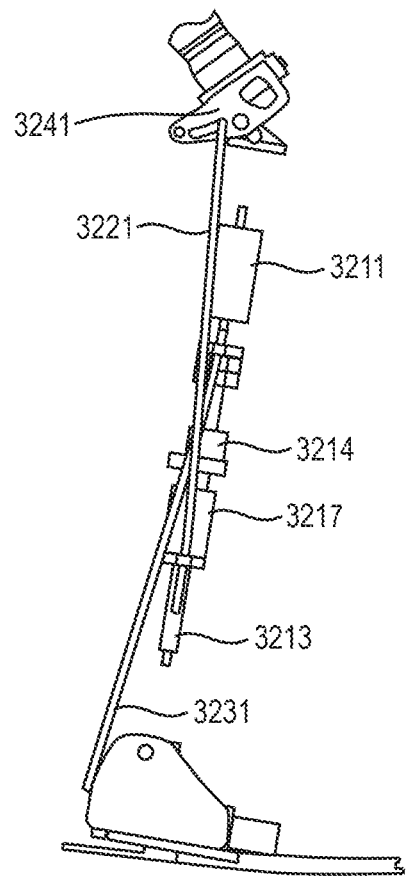
Figure 32C:
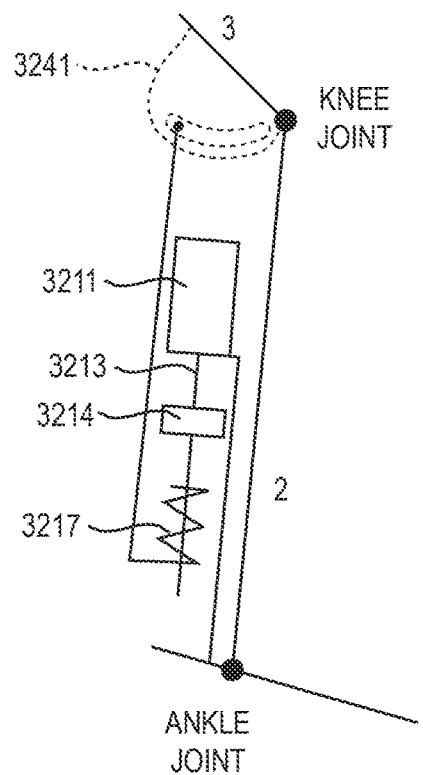
FIG. 32C is a schematic diagram of the artificial ankle and knee system seen in FIGS. 32A and 32B.
Figure 32D:
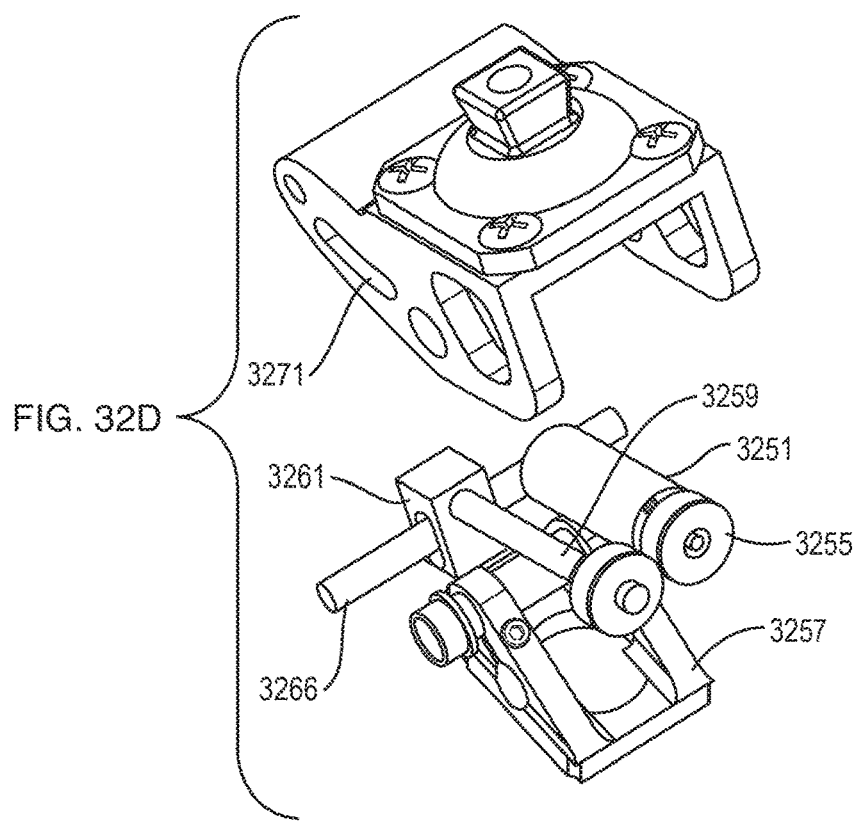
FIG. 32D shows the knee's variable moment arm (VMA) device (seen at the top of FIGS. 32A and 32B) in more detail.

The bi-articular ankle-knee mechanism of FIGS. 32A-32D comprises a motor 3211, non-backdriveable mechanical transmission 3213, screw nut 3214, series spring 3217, a knee bi-articular connection 3221, an ankle bi-articular connection 3231, and a knee variable moment arm (VMA) device 3241 (seen in more detail in FIG. 32D).

During level-ground walking, we describe how the ankle-knee bi-articular mechanism would be controlled for the swing, early stance flexion, mid-stance extension, and pre-swing phases of gait.

During the swing phase and early stance knee flexion, the screw nut 3214 is moved away from the series spring 3217 so that ankle and knee joint movements do not cause the spring to compress. However, when stance knee extension begins (18% gait cycle), the lead screw nut 3214 is moved by the motor 3211 until it engages the series spring 3217. As a consequence of this control action, both knee extension and ankle dorsiflexion contributes to spring compression.

Once the knee has reached full extension, the VMA device 3241 then minimizes the moment arm that the knee bi-articular connection makes with the knee axis of rotation. Because the knee moment arm is minimized, most of the strain energy stored in the bi-articular spring contributes to ankle powered plantar flexion at terminal stance. Generally, the knee moment arm 3241 can be controlled to effectively modulate the amount of energy release that occurs through the knee joint.

The VMA device comprises a small motor 3251 plus gear train 3255, non-backdriveable lead screw 3259, lead screw nut 3261, and variable moment arm pin 3266. A shin tube mount is seen at 3257. When the motor 3251 rotates, the lead screw nut 3261 moves the variable moment arm pin 3266 across the variable moment arm slot 3271. The pin is attached to the knee bi-articular connection. Thus, the VMA motor can actively control the perpendicular distance, or moment arm, between the knee bi-articular connection and the knee axis.

SUMMARY

Several agonist-antagonist actuator variations comprising a plurality of active element transmission-spring combinations acting in parallel have described. These actuator embodiments combine active and passive elements in order to achieve high performance with minimal mass. In addition, the use of agonist-antagonist actuators as mono and poly-articular linear elements has been described. The combination of biologically-inspired musculoskeletal architectures and agonist-antagonist actuation strategies as described above provide novel, low mass, efficient and quiet biomimetic artificial limbs. These artificial limb structures may be used to advantage to provide improved orthotic and prosthetic devices and legged robotic mechanisms.

While a preferred embodiment is disclosed, many other implementations will occur to one of ordinary skill in the art and are all within the scope of the invention. Each of the various embodiments described above may be combined with other described embodiments in order to provide multiple features. Furthermore, while the foregoing describes a number of separate embodiments of the apparatus and method of the present invention, what has been described herein is merely illustrative of the Appl. of the principles of the present invention. Other arrangements, methods, modifications, and substitutions by one of ordinary skill in the art are therefore also considered to be within the scope of the present invention, which is not to be limited except by the claims that follow.

What is claimed is:

1. A system for controlling an ankle prosthesis, orthosis or exoskeleton device, the system comprising:
    a) a first member;
    b) a second member rotatably coupled with the first member to form an ankle joint;
    c) an actuator operatively coupled to the ankle joint for control of at least one of an ankle joint torque and an ankle joint stiffness;
    d) a sensor configured to measure electromyographic (EMG) signals to determine residual limb muscle activity; and
    e) a controller configured to monitor the EMG signals from the sensor and identify at least one of a user desired ankle torque and a user desired ankle stiffness based on the monitored EMG signals, the controller communicatively linked to the actuator and configured to control the actuator to adjust at least one of the ankle joint torque and the ankle joint stiffness based on the monitored EMG signals wherein an ankle stiffness control signal is derived from a sum of EMG amplitudes from at least one plantar flexion muscle and at least one dorsiflexion muscle.

2. The system of claim 1, wherein the ankle stiffness control signal is related to stiffness via a linear relationship with a zero-level control signal signifying a minimum available stiffness level and a maximum-level control signal signifying a maximum available stiffness level.

3. The system of claim 2, wherein an ankle torque control signal is derived from a difference of EMG amplitudes from at least one plantar flexion muscle and at least one dorsiflexion muscle.

* * * * *